United States Patent
Roux et al.

(10) Patent No.: US 6,730,695 B2
(45) Date of Patent: May 4, 2004

(54) 1,3-DIHYDRO-2H-INDOL-2-ONE DERIVATIVES AND THEIR USE AS LIGANDS FOR $V_{1B}$ AND $V_{1A}$ ARGININE-VASOPRESSIN RECEPTORS

(75) Inventors: Richard Roux, Vailhauques (FR); Claudine Serradeil-Le Gal, Escalquens (FR); Bernard Tonnerre, Vailhauques (FR); Jean Wagnon, Montpellier (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/182,048

(22) PCT Filed: Jan. 24, 2001

(86) PCT No.: PCT/FR01/00226
§ 371 (c)(1),
(2), (4) Date: Jul. 24, 2002

(87) PCT Pub. No.: WO01/55130
PCT Pub. Date: Aug. 2, 2001

(65) Prior Publication Data
US 2003/0114683 A1 Jun. 19, 2003

(30) Foreign Application Priority Data
Jan. 25, 2000 (FR) .............................. 00 00957

(51) Int. Cl.[7] ................... A61K 31/404; C07D 209/04; C07D 403/04
(52) U.S. Cl. ...................................... 514/414; 548/466
(58) Field of Search .................. 514/414; 548/466

(56) References Cited

U.S. PATENT DOCUMENTS

| | | |
|---|---|---|
| 5,338,755 A | 8/1994 | Wagnon et al. |
| 5,594,023 A | 1/1997 | Wagnon et al. |
| 5,773,612 A | 6/1998 | Wagnon et al. |

FOREIGN PATENT DOCUMENTS

| | | |
|---|---|---|
| WO | WO 95/18105 | 7/1995 |

*Primary Examiner*—Joseph McKane
*Assistant Examiner*—Golam M M Shameem
(74) *Attorney, Agent, or Firm*—Paul E. Dupont; Michael D. Alexander

(57) ABSTRACT

The invention relates to compounds of formula:

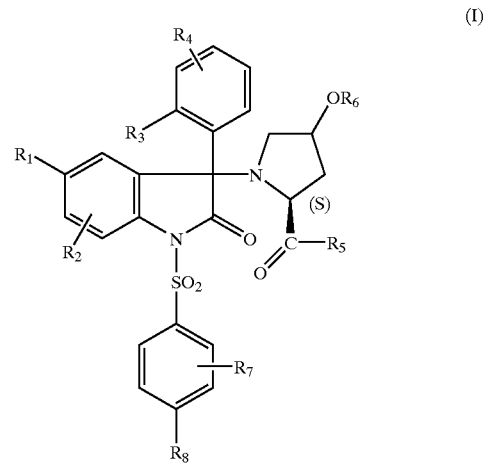

as well as the possible salts thereof with mineral or organic acids, and the solvates and/or hydrates thereof, which have affinity for and selectivity towards the $V_{1b}$ receptors or towards both the $V_{1b}$ and $V_{1a}$ receptors of arginine-vasopressin.

The invention also relates to the process for preparing them, to the intermediate compounds of formula (II) that are useful for preparing them, to pharmaceutical compositions containing them and to their use for the preparation of medicinal products.

13 Claims, No Drawings

1,3-DIHYDRO-2H-INDOL-2-ONE DERIVATIVES AND THEIR USE AS LIGANDS FOR $V_{1B}$ AND $V_{1A}$ ARGININE-VASOPRESSIN RECEPTORS

The present invention relates to novel 1,3-dihydro-2H-indol-2-one derivatives, to a process for preparing them and to pharmaceutical compositions containing them.

The compounds according to the present invention have affinity for and selectivity towards the $V_{1b}$ receptors or towards both the $V_{1b}$ and $V_{1a}$ receptors of arginine-vasopressin (AVP).

AVP is a hormone which is known for its antidiuretic effect and its effect in regulating arterial pressure. It stimulates several types of receptor: $V_1$ ($V_{1a}$, $V_{1b}$), $V_2$. These receptors are located in particular in the liver, the vessels (coronary, renal and cerebral), the platelets, the kidneys, the uterus, the adrenal glands, the pancreas, the central nervous system and the pituitary gland. AVP thus exerts cardiovascular, hepatic, pancreatic, antidiuretic and platelet-aggregating effects and effects on the central and peripheral nervous system, and on the uterine sphere.

The location of the various receptors is described in: S. Jard et al., Vasopressin and oxytocin receptors: an overview, in Progress in Endocrinology. H. Imura and K. Shizurne ed., Experta Medica, Amsterdam, 1988, 1183–1188, as well as in the following articles: J. Lab. Clin. Med., 1989, 114,(6), 617–632 and Pharmacol. Rev., 1991, 43(1), 73–108.

More particularly, the AVP $V_{1a}$ receptors are located in many peripheral organs and in the brain. They have been cloned in rats and man and they regulate most of the known effects of AVP: platelet aggregation; uterine contractions; the contraction of blood vessels; secretion of aldosterone, cortisol, CRF (corticotropin-releasing factor) and adrenocorticotrophic hormone (ACTH); hepatic glycogenolysis, cell proliferation and the main central effects of AVP (hypothermia, memory, etc.).

The $V_{1b}$ receptors were initially identified in the adenohypophysis of various animal species (rats, pigs, bovines, sheep, etc.) including man (S. Jard et al., Mol. Pharmacol., 1986, 30, 171–177; Y. Arsenijevic et al., J. Endocrinol., 1994, 141, 383–391; J. Schwartz et al., Endocrinology, 1991, 129(2), 1107–1109; Y. De Keyser et al., FEBS Letters, 1994, 356, 215–220) in which they stimulate the release of adrenocorticotrophic hormone via AVP and potentiate the effects of CRF on the release of ACTH (G. E. Gillies et al., Nature, 1982, 299, 355). In the hypothalamus, the $V_{1b}$ receptors also induce a direct release of CRF (Neuroendocrinology, 1994, 60, 503–508) and are, in these various respects, involved in stress situations.

These $V_{1b}$ receptors have been cloned in rats, man and mice (Y. De Keyser, FEBS Letters, 1994, 356, 215–220; T. Sugimoto et al., J. Biol. Chem. 1994, 269(43), 27088–27092; M. Saito et al., Biochem. Biophys. Res. Commun., 1995, 212(3), 751–757; S. J. Lolait et al., Neurobiology, 1996, 92, 6783–6787; M. A. Ventura et al., Journal of Molecular Endocrinology, 1999, 22, 251–260) and various studies (in situ hybridization, PCR [polymerase chain reaction], etc.) reveal the ubiquitous presence of these receptors in various central tissues (brain, hypothalamus and adenohypophysis in particular) and peripheral tissues (kidney, pancreas, adrenals, heart, lungs, intestine, stomach, liver, mesentery, bladder, thymus, spleen, uterus, retina, thyroid, etc.) and in certain tumours (hypophyseal, pulmonary, etc.) suggesting a broad biological and/or pathological role for these receptors and a potential involvement in various diseases.

By way of example, in rats, studies have shown that AVP regulates the endocrine pancreas, via the $V_{1b}$ receptors, by stimulating the secretion of insulin and glucagon (B. Lee et al., Am. J. Physiol. 269 (Endocrinol. Metab. 32): E1095–E1100, 1995) or the production of catecholamines in the medullo-adrenal which is the site of a local synthesis of AVP (E. Grazzini et al., Endocrinology, 1996, 137(a), 3906–3914). Thus, in the latter tissue, AVP is thought to have a crucial role, via these receptors, in certain types of adrenal pheochromocytomas which secrete AVP and thereby induce a sustained production of catecholamines which are the cause of hypertension and which are resistant to angiotensin II-receptor antagonists and to conversion enzyme inhibitors. The adrenal cortex is also rich in $V_{1a}$ receptors involved in the production of glucocorticoids and mineralocorticoids (aldosterone and cortisol). Via these receptors, AVP (in the circulation or synthesized locally) can induce a production of aldosterone with an efficacy which is comparable to that of angiotensin II (G. Guillon et al., Endocrinology, 1995, 136(3), 1285–1295). Cortisol is a powerful regulator of the production of ACTH, the stress hormone.

Recent studies have also shown that the adrenal glands are capable of directly releasing CRF and/or ACTH via activation of the $V_{1b}$ and/or $V_{1a}$ receptors borne by the medullary cells (G. Mazzocchi et al., Peptides, 1997, 18(2), 191–195; E. Grazzini et al., J. Clin. Endocrinol. Metab., 1999, 84(6), 2195–2203).

The $V_{1b}$ receptors are also considered as a label for ACTH-secreting tumours such as certain pituitary tumours, certain bronchial carcinomas (SCLC [small lung cell cancers]), pancreatic, adrenal and thyroid carcinomas, inducing Cushing's, syndrome in certain cases (J. Bertherat et al., Eur. J. Endocrinol., 1996, 135, 173; G. A. Wittert et al., Lancet, 1990, 335, 991–994; G. Dickstein et al., J. Clin. Endocrinol. Metab., 1996, 81(8), 2934–2941). As regards the Via receptors, they are a more specific label for small cell lung cancers (SCLC) (P. J. Woll et al., Biochem. Biophys. Res. Commun., 1989, 164(1), 66–73). Thus, the compounds according to the present invention are obvious diagnostic tools and offer a novel therapeutic approach in the proliferation and detection of these tumours, even at an early stage (radiolabelling; SPECT [single photon emission computed tomography]; PET scan [positron emission tomography scanner]).

The abundant presence of the $V_{1b}$ receptor messenger in the stomach and intestine suggests an involvement of AVP via this receptor on the release of gastrointestinal hormones such as cholecystokinin, gastrin or secretin (T. Sugimoto et al., Molecular cloning and functional expression of $V_{1b}$ receptor gene, in Neurohypophysis: Recent Progress of Vasopressin and Oxytocin Research; T. Saito, K. Kurokawa and S. Yoshida ed., Elvesier Science, 1995, 409–413).

1,3-Dihydro-2H-indol-2-one derivatives have been described in certain patent applications as arginine-vasopressin receptor ligands and/or oxytocin receptor ligands: mention may be made of patent applications WO 93/15051, EP-A-0 636 608. EP-A-0 636 609, WO 95/18105, WO 97/15556 and WO 98/25901.

No non-peptide compound with affinity for and selectivity towards the $V_{1b}$ receptors or simultaneously for and towards both the $V_{1b}$ and $V_{1a}$ receptors of arginine-vasopressin is known to date.

Novel 1,3-dihydro-2H-indol-2-one derivatives have now been found which have affinity for and selectivity towards the $V_{1b}$ receptors or for and towards both the $V_{1b}$ and $V_{1a}$ receptors of arginine-vasopressin.

These compounds may be used for the preparation of medicinal products that are useful in the treatment or prevention of any pathology in which arginine-vasopressin and/or the $V_{1b}$ receptors or both the $V_{1b}$ receptors and the $V_{1a}$ receptors are involved, in particular in the treatment or prevention of complaints of the cardiovascular system, for example hypertension; of the central nervous system, for example stress, anxiety, depression, compulsive obsessive disorder and panic attacks; of the renal system; of the gastric system as well as in the treatment of small cell lung cancers; of obesity; of type II diabetes; of insulin resistance; of hypertriglyceridemia; of atherosclerosis; of Cushing's syndrome; of any pathology following stress and chronic stress states.

Thus, according to one of its aspects, one subject of the present invention is compounds of formula:

(I)

in which:
- $R_1$ represents a halogen atom; a $(C_1-C_4)$alkyl; a $(C_1-C_4)$alkoxy; a trifluoromethyl radical; a trifluoromethoxy radical;
- $R_2$ represents a hydrogen atom; a halogen atom; a $(C_1-C_4)$alkyl; a $(C_1-C_4)$alkoxy; a trifluoromethyl radical;
- or $R_2$ is in position -6- of the indol-2-one ring and $R_1$ and $R_2$ together represent a divalent trimethylene radical;
- $R_3$ represents a halogen atom; a hydroxyl; a $(C_1-C_2)$alkyl; a $(C_1-C_2)$alkoxy; a trifluoromethoxy radical;
- $R_4$ represents a hydrogen atom; a halogen atom; a $(C_1-C_2)$alkyl; a $(C_1-C_2)$alkoxy;
- or $R_4$ is in position -3- of the phenyl and $R_3$ and $R_4$ together represent a methylenedioxy radical;
- $R_5$ represents an ethylamino group; a dimethylamino group; an azetidin-1-yl radical; a $(C_1-C_2)$alkoxy;
- $R_6$ represents a hydrogen atom; a $(C_1-C_4)$alkyl; a group $-(CH_2)n-CO-R_9$; a group $-CO-(CH_2)n-NR_{11}$;
- $R_7$ represents a $(C_1-C_4)$alkoxy;
- $R_8$ represents a $(C_1-C_4)$alkoxy;
- $R_9$ represents a hydroxyl; a $(C_1-C_4)$alkoxy; a group $-NR_{12}R_{13}$;
- $R_{10}$ and $R_{11}$ each independently represent a $(C_1-C_4)$alkyl;
- or $R_{10}$ and $R_{11}$, together with the nitrogen atom to which they are attached, constitute a heterocyclic radical chosen from: azetidin-1-yl, pyrrolidin-1-yl, piperid-1-yl, piperazin-1-yl, morpholin-4-yl or thiomorpholin-4-yl;
- $R_{12}$ represents a hydrogen or a $(C_1-C_4)$alkyl;
- $R_{13}$ represents a $(C_1-C_4)$alkyl; a $-C(CH_3)_2CH_2OH$ group; a $-C(CH_3)(CH_2OH)_2$ group; a $-C(CH_2OH)_3$ group;
- or $R_{12}$ and $R_{13}$, together with the nitrogen atom to which they are attached, constitute a heterocyclic radical chosen from: azetidin-1-yl, pyrrolidin-1-yl, piperid-1-yl, piperazin-1-yl, morpholin-4-yl or thiomorpholin-4-yl;
- n is 1 or 2;

as well as the solvates and/or hydrates thereof and the possible salts thereof with mineral or organic acids.

The term "halogen atom" means a chlorine, bromine, fluorine or iodine atom.

The terms "alkyl" and "alkoxy", respectively, mean a linear or branched alkyl radical or alkoxy radical, respectively.

The compounds of formula (I) comprise at least 3 asymmetric carbon atoms, the carbon atom bearing the substituent $COR_5$ has the (S) configuration, and the carbon atom bearing the substituent $OR_6$ has either the (R) configuration or the (S) configuration. The optically pure isomers of the compounds of formula (I) and the mixtures thereof in all proportions form part of the invention.

The salts are generally prepared with pharmaceutically acceptable acids, but the salts of other acids which are useful for purifying or isolating the compounds of formula (I) also form part of the invention. The pharmaceutically acceptable salts of the compounds of formula (I) are, for example, the hydrochloride, hydrobromide, sulphate, hydrogen sulphate, dihydrogen phosphate, methanesulphonate, benzenesulphonate, naphthalenesulphonate, paratoluenesulphonate, maleate, fumarate, succinate, citrate, acetate, gluconate or oxalate.

According to the present invention, the compounds of formula (I) that are preferred are those in which:
- $R_1$ represents a halogen atom; a $(C_1-C_4)$alkyl; a trifluoromethyl radical; a trifluoromethoxy radical;
- $R_2$ represents a hydrogen atom; a halogen atom; a $(C_1-C_4)$alkyl; a $(C_1-C_4)$alkoxy; a trifluoromethyl radical;
- or $R_2$ is in position -6- of the indol-2-one ring and $R_1$ and $R_2$ together represent a divalent trimethylene radical;
- $R_3$ represents a halogen atom; a hydroxyl; a $(C_1-C_2)$alkoxy;
- $R_4$ represents a hydrogen atom; a halogen atom; a $(C_1-C_2)$alkyl; a $(C_1-C_2)$alkoxy;
- or $R_4$ is in position -3- of the phenyl and $R_3$ and $R_4$ together represent a methylenedioxy radical;
- $R_5$ represents an ethylamino group; a dimethylamino group; an azetidin-1-yl group; a $(C_1-C_2)$alkoxy;
- $R_6$ represents a hydrogen atom; a $(C_1-C_4)$alkyl;
- $R_7$ represents a $(C_1-C_4)$alkoxy;
- $R_8$ represents a $(C_1-C_4)$alkoxy;

as well as the solvates and/or hydrates thereof and the possible salts thereof with mineral or organic acids.

According to the present invention, the compounds of formula (I) in which $R_1$ represents a chlorine atom, a methyl radical or a trifluoromethoxy radical are preferred.

According to the present invention, the compounds of formula (I) in which $R_2$ represents a hydrogen atom or is in position -6- of the indol-2-one and represents a chlorine atom, a methyl radical, a methoxy radical or a trifluoromethyl radical are preferred.

According to the present invention, the compounds of formula (I) in which $R_3$ represents a chlorine atom, a fluorine atom, a methoxy radical, an ethoxy radical or a trifluoromethoxy radical are preferred.

According to the present invention, the compounds of formula (I) in which $R_4$ represents a hydrogen atom or is in position -3- or -4- of the phenyl and represents a fluorine atom or a methoxy radical; or $R_4$ is in position -3- of the phenyl and, together with $R_3$, represent a methylenedioxy radical, are preferred.

According to the present invention, the compounds of formula (I) in which $R_5$ represents a dimethylamino group, an azetidin-1-yl radical or a methoxy radical are preferred.

According to the present invention, the compounds of formula (I) in which $R_6$ represents a halogen atom, a methyl radical, an ethyl radical, a tert-butoxycarbonylmethyl radical, a carboxymethyl radical, a [[2-hydroxy-1-(hydroxymethyl)-1-methylethyl]amino]carbonylmethyl radical, a (1-piperazinyl)carbonylmethyl radical, a (4-morpholinyl)carbonylmethyl radical or a 3-(4-morpholinyl)propanoyl radical are preferred.

According to the present invention, the compounds of formula (I) in which $R_7$ is in position -2- or -3- of the phenyl and represents a methoxy radical are preferred.

According to the present invention, the compounds of formula (I) in which $R_8$ represents a methoxy radical are preferred.

According to the present invention, the compounds of formula (I) in the form of optically pure isomers are preferred.

Particularly preferred are the optically pure isomers of the compounds of formula:

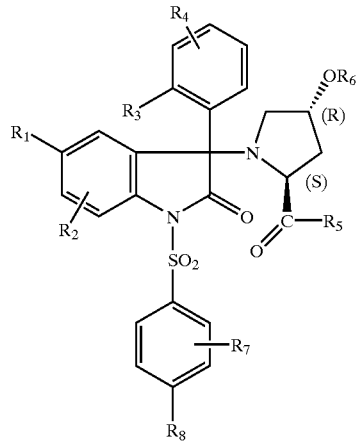

(Ia)

in which $R_1$, $R_2$, $R_3$, $R_4$, $R_5$, $R_6$, $R_7$ and $R_8$ are as defined for a compound of formula (I), the carbon atom bearing substituent $OR_6$ has the (R) configuration and the carbon atom in position 3 of the indol-2-one has either the (R) configuration or the (S) configuration.

The laevorotatory isomer of the compounds of formula (Ia) is more particularly preferred.

Most particularly preferred are the compounds of formula (Ia), laevorotatory isomer, in which:

$R_1$ represents a chlorine atom, a methyl radical or a trifluoromethoxy radical;

$R_2$ represents a hydrogen atom or is in position -6- of the indol-2-one and represents a chlorine atom, a methyl radical, a methoxy radical or a trifluoromethyl radical;

$R_3$ represents a chlorine atom, a fluorine atom, a methoxy radical or an ethoxy radical;

$R_4$ represents a hydrogen atom or is in position -3- or -4- of the phenyl and represents a fluorine atom or a methoxy radical;

or $R_4$ is in position -3- of the phenyl and, together with $R_3$, represent a methylenedioxy radical;

$R_5$ represents a dimethylamino radical or a methoxy radical;

$R_6$ represents a hydrogen atom; a methyl radical; an ethyl radical; a Lert-butyloxycarbonylmethyl radical; a carboxymethyl radical; a [[2-hydroxy-1-(hydroxymethyl)-1-methylethyl]amino]carbonylmethyl radical; a (1-piperazinyl)carbonylmethyl radical; a (4-morpholinyl)carbonylmethyl radical; a 3-(4-morpholinyl)propanoyl radical;

$R_7$ is in position -2- of the phenyl and represents a methoxy radical;

$R_8$ represents a methoxy radical;

as well as the salts thereof with mineral or organic acids, and the solvates and/or hydrates thereof.

The following compounds:

(2S,4R)-1-[5-Chloro-1-[(2,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide, laevorotatory isomer;

(2S,4R)-1-[5-Chloro-1-[(2,4-dimethoxyphenyl)sulphonyl]-3-(2-methoxyphenyl)-2-oxo-2,3-dihydro-1H-indol-3-yl]-4-methoxy-N,N-dimethyl-2-pyrrolidinecarboxamide, laevorotatory isomer;

(2S,4R)-1-[5-Chloro-3-(2-chlorophenyl)-1-[(2,4-dimethoxyphenyl)sulphonyl]-2-oxo-2,3-dihydro-1H-indol-3-yl]-4-hydroxy-N,N-dimethyl-2-pyrrolidinecarboxamide, laevorotatory isomer;

(2S,4R)-1-[5-Chloro-3-(2-chlorophenyl)-1-[(2,4-dimethoxyphenyl)sulphonyl]-6-methoxy-2-oxo-2,3-dihydro-1H-indol-3-yl]-4-methoxy-N,N-dimethyl-2-pyrrolidinecarboxamide, laevorotatory isomer;

(2S,4R)-1-[5-Chloro-1-[(3,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide, laevorotatory isomer;

Methyl (2S,4R)-1-[5-chloro-3-(2-methoxyphenyl)-1-[(3,4-dimethoxyphenyl)sulphonyl]-2-oxo-2,3-dihydro-1H-indol-3-yl]-4-hydroxy-2-pyrrolidine-carboxylate, laevorotatory isomer;

(2S,4R)-1-[5-Methyl-1-[(2,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide, laevorotatory isomer;

(2S,4R)-1-[5-Chloro-1-[(2,4-dimethoxyphenyl)sulphonyl]-3-(2-methoxyphenyl)-2-oxo-2,3-dihydro-1H-indol-3-yl]-2-(azetidin-1-ylcarbonyl)-4-hydroxypyrrolidinecarboxamide, laevorotatory isomer;

(2S,4R)-1-[5-Trifluoromethoxy-1-[(2,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide, laevorotatory isomer;

(2S,4R)-1-[5-Chloro-1-[(2,4-dimethoxyphenyl)sulphonyl]-3-(2-methoxyphenyl)-6-methyl-2-oxo-2,3-dihydro-1H-indol-3-yl]-4-hydroxy-N,N-dimethyl-2-pyrrolidinecarboxamide, laevorotatory isomer;

(2S,4R)-1-[3-(2-Chlorophenyl)-1-[(2,4-dimethoxyphenyl)sulphonyl]-5,6-dimethyl-2-oxo-2,3-dihydro-1H-indol-3-yl]-4-hydroxy-N,N-dimethyl-2-pyrrolidinecarboxamide, laevorotatory isomer;

(2S,4R)-1-[5-Chloro-1-[(2,4-dimethoxyphenyl)sulphonyl]-3-(2,3-dimethoxyphenyl)-2-oxo-2,3- dihydro-1H-indol-3-yl]-4-methoxy-N,N-dimethyl-2-pyrrolidinecarboxamide, laevorotatory isomer;

(2S,4R)-1-[5-Chloro-1-[(2,4-dimethoxyphenyl)sulphonyl]-3-(2-methoxyphenyl)-6-trifluoromethyl-2-oxo-2,3-dihydro-1H-indol-3-yl]-4-methoxy-N,N-dimethyl-2-pyrrolidinecarboxamide, laevorotatory isomer;

(2S,4R)-1-[6-Chloro-1-[(2,4-dimethoxyphenyl)sulphonyl]-3-(2-methoxyphenyl)-5-methyl-2-oxo-2,3-dihydro-1H-indol-3-yl]-4-methoxy-N,N-dimethyl-2-pyrrolidinecarboxamide, laevorotatory isomer;

(2S,4R)-1-[5-Chloro-1-[(2,4-dimethoxyphenyl)sulphonyl]-3-(2-methoxyphenyl)-2-oxo-2,3-dihydro-1H-indol-3-yl]-4-ethoxy-N,N-dimethyl-2-pyrrolidinecarboxamide, laevorotatory isomer;

(2S,4R)-1-[5-Chloro-1-[(2,4-dimethoxyphenyl)sulphonyl]-3-(2,3-dimethoxyphenyl)-2-oxo-2,3-dihydro-1H-indol-3-yl]-4-hydroxy-N,N-dimethyl-2-pyrrolidinecarboxamide, laevorotatory isomer;

(2S,4R)-1-[5,6-Dichloro-3-(2-chlorophenyl)-1-[(2,4-dimethoxyphenyl)sulphonyl]-2-oxo-2,3-dihydro-1H-indol-3-yl]-4-hydroxy-N,N-dimethyl-2-pyrrolidinecarboxamide, laevorotatory isomer;

Methyl(2S,4R)-1-[5-chloro-1-[(2,4-dimethoxyphenyl)sulphonyl]-3-(2-methoxyphenyl)-2-oxo-2,3-dihydro-1H-indol-3-yl]-4-methoxy-2-pyrrolidinecarboxylate, laevorotatory isomer;

Methyl(2S,4R)-1-[5-chloro-1-[(2,4-dimethoxyphenyl)sulphonyl]-3-(2-methoxyphenyl)-6-methyl-2-oxo-2,3-dihydro-1H-indol-3-yl]-4-methoxy-2-pyrrolidinecarboxylate, laevorotatory isomer;

(2S,4R)-1-[5-Chloro-1-[(2,4-dimethoxyphenyl)sulphonyl]-3-(2-ethoxyphenyl)-2-oxo-2,3-dihydro-1H-indol-3-yl]-4-hydroxy-N,N-dimethyl-2-pyrrolidinecarboxamide, laevorotatory isomer;

(2S,4R)-1-[5-Chloro-1-[(2,4-dimethoxyphenyl)sulphonyl]-3-(2,3-difluorophenyl)-2-oxo-2,3-dihydro-1H-indol-3-yl]-4-hydroxy-N,N-dimethyl-2-pyrrolidinecarboxamide, laevorotatory isomer;

(2S,4R)-1-[5-Chloro-1-[(2,4-dimethoxyphenyl)sulphonyl]-3-(2,4-dimethoxyphenyl)-2-oxo-2,3-dihydro-1H-indol-3-yl]-4-hydroxy-N,N-dimethyl-2-pyrrolidinecarboxamide, laevorotatory isomer;

(2S,4R)-1-[5-Chloro-1-[(2,4-dimethoxyphenyl)sulphonyl]-3-(1,3-benzodioxol-4-yl)-2-oxo-2,3-dihydro-1H-indol-3-yl]-4-hydroxy-N,N-dimethyl-2-pyrrolidinecarboxamide, laevorotatory isomer;

(2S,4R)-1-[5,6-Dichloro-1-[(2,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide, laevorotatory isomer;

tert-Butyl 2-[[(3R,5S)-1-[5-chloro-1-[(2,4-dimethoxyphenyl)sulphonyl]-3-(2-methoxyphenyl)-2-oxo-2,3-dihydro-1H-indol-3-yl]-5-[(dimethylamino)carbonyl]-3-pyrrolidinyl]oxy]acetate, laevorotatory isomer;

2-[[(3R,5S)-1-[5-Chloro-1-[(2,4-dimethoxyphenyl)sulphonyl]-3-(2-methoxyphenyl)-2-oxo-2,3-dihydro-1H-indol-3-yl]-5-[(dimethylamino)carbonyl]-3-pyrrolidinyl]oxy]acetic acid, laevorotatory isomer;

(2S,4R)-1-[5-Chloro-1-[(2,4-dimethoxyphenyl)sulphonyl]-3-(2-methoxyphenyl)-2-oxo-2,3-dihydro-1H-indol-3-yl]-4-[2-[[2-hydroxy-1-(hydroxymethyl)-1-methylethyl]amino]-2-oxoethoxy]-N,N-dimethyl-2-pyrrolidinecarboxamide, laevorotatory isomer;

(2S,4R)-1-[5-Chloro-1-[(2,4-dimethoxyphenyl)sulphonyl]-3-(2-methoxyphenyl)-2-oxo-2,3-dihydro-1H-indol-3-yl]-N,N-dimethyl-4-[2-oxo-2-(1-piperazinyl)ethoxy]-2-pyrrolidinecarboxamide, laevorotatory isomer;

(2S,4R)-1-[[(2,4-Dimethoxyphenyl)sulphonyl]-3-(2-methoxyphenyl)-2-oxo-2,3-dihydro-1H-indol-3-yl]-N,N-dimethyl-4-[2-oxo-2-(4-morpholinyl)ethoxy]-2-pyrrolidinecarboxamide, laevorotatory isomer;

(3R,5S)-1-[5-Chloro-1-[(2,4-dimethoxyphenyl)sulphonyl]-3-(2-methoxyphenyl)-2-oxo-2,3-dihydro-1H-indol-3-yl]-5-[(dimethylamino)carbonyl]-3-pyrrolidinyl 3-(4-morpholinyl)propanoate, laevorotatory isomer;

as well as the possible salts thereof with mineral or organic acids, and the solvates and/or hydrates thereof are more particularly preferred.

According to another of its aspects, a subject of the present invention is a process for preparing compounds of formula (I), possible salts thereof with mineral or organic acids, and solvates and/or hydrates thereof, characterized in that:

a compound of formula:

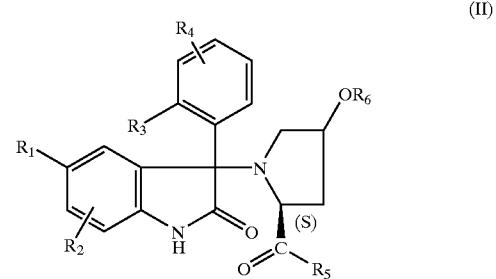

(II)

in which $R_1$, $R_2$, $R_3$, $R_4$, $R_5$ and $R_6$ are as defined for a compound of formula (I), is reacted, in the presence of a base, with a halide of formula:

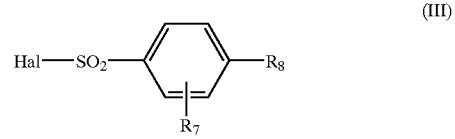

(III)

in which $R_7$ and $R_8$ are as defined for a compound of formula (I) and Hal represents a halogen atom.

The compound of formula (I) is optionally converted into a salt thereof with mineral or organic acids.

The reaction is carried out in the presence of a strong base, for instance a metal hydride such as sodium hydride or an alkali metal alkoxide such as potassium tert-butoxide, in an anhydrous solvent such as N,N-dimethylformamide or tetrahydrofuran and at a temperature of between −70° C. and +60° C. The reaction is preferably carried out using a compound of formula (III) in which Hal=Cl.

A compound of formula (I) in which $R_6$ represents a ($C_1$–$C_4$)alkyl may also be prepared by reacting a compound of formula (I) in which $R_6$ represents hydrogen with a ($C_1$–$C_4$)alkyl halide, in the presence of a base such as a metal hydride, in an inert solvent such as N,N-dimethylformamide or tetrahydrofuran according to the conventional methods.

A compound of formula (I) in which $R_6$ represents a group —$(CH_2)n$-CO—$R_9$ in which $R_9$ represents a hydroxyl is preferably prepared by hydrolysing a compound of formula (I) in which $R_6$ represents a group —$(CH_2)n$-CO—$R_9$ in which $R_9$ represents a tert-butyloxy, in acidic medium, using a strong acid such as trifluoroacetic acid or hydrochloric acid in a solvent such as dichloromethane or dioxane and at a temperature of between 0° C. and room temperature.

A compound of formula (I) in which $R_6$ represents a group —$(CH_2)n$-CO—$R_9$ in which $R_9$ represents a group —$NR_{12}R_{13}$ is preferably prepared by reacting a compound of formula (I) in which $R_9$ represents a hydroxyl with an amine of formula H—$NR_{12}R_{13}$ according to the conventional methods of peptide coupling.

The compounds of formula (I) thus obtained may be subsequently separated from the reaction medium and purified according to the conventional methods, for example by crystallization or chromatography.

The compounds of formula (I) thus obtained are isolated in free base or salt form, according to the conventional techniques.

When the compounds of formula (I) are obtained in free base form, the salification is carried out by treatment with the selected acid in an organic solvent. By treating the free base, dissolved, for example, in an ether such as diethyl ether or in an alcohol such as 2-propanol or in acetone or in dichloromethane, or in ethyl acetate or in acetonitrile, with a solution of the selected acid in one of the abovementioned solvents, the corresponding salt is obtained, which is isolated according to the conventional techniques.

Thus, the hydrochloride, hydrobromide, sulphate, trifluoroacetate, hydrogen sulphate, dihydrogen phosphate, methanesulphonate, oxalate, maleate, succinate, fumarate, 2-naphthalenesulphonate, benzenesulphonate, paratoluenesulphonate, gluconate, citrate or acetate is prepared, for example.

At the end of the reaction, the compounds of formula (I) may be isolated in the form of a salt thereof, for example the hydrochloride or oxalate; in this case, if necessary, the free base may be prepared by neutralizing the said salt with a mineral or organic base, such as sodium hydroxide or triethylamine or with an alkali metal carbonate or bicarbonate, such as sodium or potassium carbonate or bicarbonate.

The compounds of formula (II) are prepared by reacting a 3-halo-1,3-dihydro-2H-indol-2-one compound of formula:

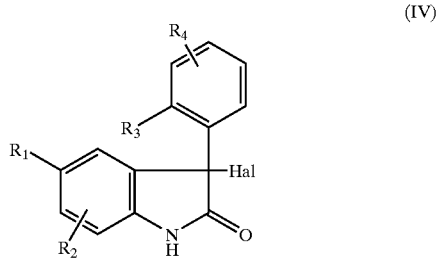

(IV)

in which $R_1$, $R_2$, $R_3$ and $R_4$ are as defined for a compound of formula (I) and Hal represents a halogen atom, preferably chlorine or bromine, with a compound of formula:

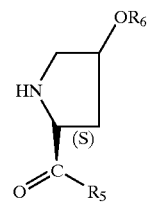

(V)

in which $R_5$ and $R_6$ are as defined for a compound of formula (I). The reaction is carried out in the presence of a base such as diisopropylethylamine or triethylamine, in an inert solvent such as dichloromethane or tetrahydrofuran or a mixture of these solvents and at a temperature of between room temperature and the reflux temperature of the solvent.

The compounds of formula (III) are known or prepared by known methods such as those disclosed in EP-B-0 469 984 and WO 95/18105. For example, the compounds of formula (III) may be prepared by halogenating the corresponding benzenesulphonic acids or salts thereof, for example the sodium or potassium salts thereof. The reaction is carried out in the presence of a halogenating agent such as phosphorus oxychloride, thionyl chloride, phosphorus trichloride, phosphorus tribromide or phosphorus pentachloride, without solvent or in an inert solvent such as a halogenated hydrocarbon or N,N-dimethylformamide and at a temperature of between −10° C. and 200° C.

2,4-Dimethoxybenzenesulphonyl chloride is prepared according to J. Am. Chem. Soc., 1952, 74, 2008. 3,4-Dimethoxybenzenesulphonyl chloride is commercially available or is prepared according to J. Med. Chem., 1977, 20(10), 1235–1239.

The compounds of formula (IV) are known and are prepared according to known methods such as those disclosed in WO 95/18105.

For example, a compound of formula:

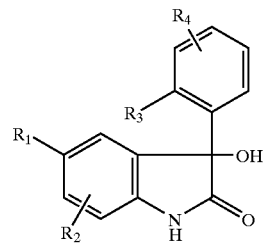

(VI)

in which $R_1$, $R_2$, $R_3$ and $R_4$ are as defined for a compound of formula (I), is converted into a compound of formula (IV) in which Hal=Cl by the action of thionyl chloride in the presence of a base such as pyridine, in an inert solvent such as dichloromethane and at a temperature of between 0° C. and room temperature.

According to another example for preparing the compounds of formula (IV), a compound of formula:

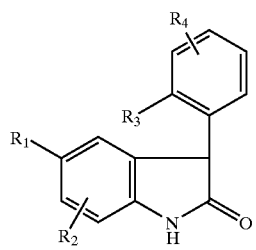

in which $R_1$, $R_2$, $R_3$ and $R_4$ are as defined for a compound of formula (I), is converted into a compound of formula (IV) by means of a halogenating agent such as bromine, according to the process disclosed in Farm. Zh.(Kiev), 1976, 5, 30–33.

The compounds of formula (VI) are known and are prepared according to known methods such as those disclosed in WO 95/18105.

For example, a compound of formula (VI) is prepared by reacting a 1H-indole-2,3-dione derivative of formula:

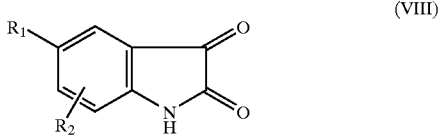

in which $R_1$ and $R_2$ are as defined for a compound of formula (I), with an organomagnesium derivative of formula:

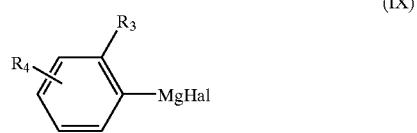

in which $R_3$ and $R_4$ are as defined for a compound of formula (I) and Hal represents a halogen atom, preferably bromine or iodine, in an inert solvent such as tetrahydrofuran or diethyl ether.

It is also possible to prepare a compound of formula (VI) in which $R_3$ is as defined for a compound of formula (I) and $R_4$, which is other than hydrogen, is in position -3- or -6- of the phenyl, by reacting a compound of formula:

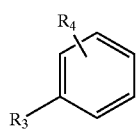

in which $R_3$ is as defined for a compound of formula (I) and $R_4$ is in position -2- or -5- of the phenyl, with a lithium derivative such as n-butyllithium, and the lithiated intermediate thus obtained is then reacted with a compound of formula (VIII). The reaction is carried out in a solvent such as diethyl ether, tetrahydrofuran or hexane or a mixture of these solvents, at a temperature of between −70° C. and room temperature.

The 1H-indole-2,3-dione derivatives (VIII) are commercially available or are prepared according to the methods disclosed in Tetrahedron Letters, 1998, 39, 7679–7682; Tetrahedron Letters, 1994, 35, 7303–7306; J. Org. Chem., 1977, 42(8), 1344–1348; J. Org. Chem., 1952, 17, 149–156; J. Am. Chem. Soc., 1946, 68, 2697–2703; Organic Syntheses, 1925, V, 71–74 and Advances in Heterocyclic Chemistry, A. R. Katritzky and A. J. Boulton, Academic Press, New York, 1975, 18, 2–58.

The organomagnesium derivatives (1x) are prepared according to the conventional methods that are well known to those skilled in the art.

The compounds of formula (XVII) are known or prepared according to known methods.

A compound of formula (VI) may also be prepared by air-oxidation of a compound of formula (VII) in the presence of a base such as sodium hydride and in the presence of dimethyl disulphide.

In particular, the compounds of formula (VI) in which $R_3=(C_1-C_2)$alkoxy and $R_4=H$, or $R_3=R_4=(C_1-C_2)$alkoxy with $R_4$ in position -3 or -6 of the phenyl, $R_2$ is other than a halogen atom and $R_1$ is as defined for a compound of formula (I), may be prepared by following the process described in Scheme 1.

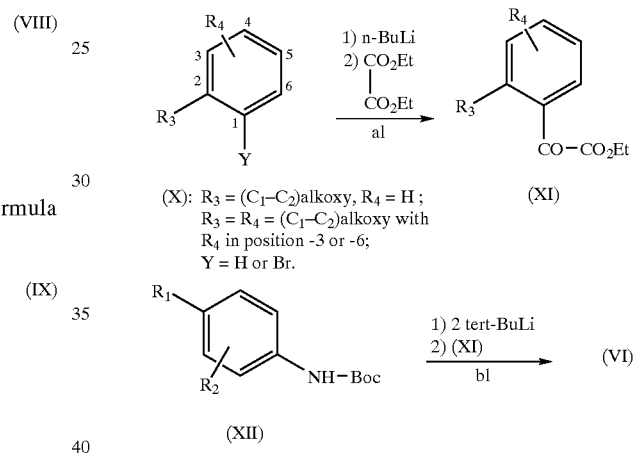

In step a1 of Scheme 1, a compound of formula (X) is first reacted with a lithium derivative such as n-butyllithium, in the absence or presence of a base such as N,N,N',N'-tetramethylenediamine, and the lithiated intermediate thus obtained is then reacted with diethyl oxalate to give the compound of formula (XI). The reaction is carried out in an inert solvent such as diethyl ether, tetrahydrofuran or hexane or a mixture of these solvents and at a temperature of between −70° C. and room temperature.

In step b1, a compound of formula (XII) is first reacted with two equivalents of a lithium derivative such as tert-butyllithium, and the lithiated intermediate thus obtained is then reacted with the compound of formula (XI) to give the expected compound of formula (VI). The reaction is carried out in an inert solvent such as diethyl ether, tetrahydrofuran or pentane or a mixture of these solvents and at a temperature of between −70° C. and room temperature.

The compounds of formula (X) are commercially available or synthesized conventionally.

The compounds of formula (XII) are prepared by reacting the corresponding aniline derivatives with di-tert-butyl dicarbonate according to the conventional methods.

The compounds of formula (VII) are known and are prepared according to known methods such as those disclosed in WO 95/18105 or in J. Org. Chem., 1968, 33, 1640–1643.

The compounds of formula (V) in which $R_5$ represents a $(C_1-C_2)$alkoxy and $R_6$<H are commercially available.

The compounds of formula (V) in which $R_5$ represents a $(C_1-C_2)$alkoxy and $R_6=(C_1-C_4)$alkyl are known or are prepared according to known methods such as those disclosed in J. Med. Chem., 1988, 31, 875–885 starting with (2S,4R)- or (2S,4S)-4-hydroxy-pyrrolidine-2-carboxylic acid protected on the nitrogen atom of the pyrrolidine.

The compounds of formula (V) in which $R_5$ is an ethylamino or dimethylamino group or an azetidin-1-yl radical and $R_6$=H or $(C_1-C_4)$alkyl are prepared according to Scheme 2 below in which Pr represents an N-protecting group, in particular benzyloxycarbonyl or tert-butoxycarbonyl.

In step a2 of Scheme 2, the nitrogen atom of the 4(R)- or 4(S)-hydroxy-(S)-proline is protected according to the conventional methods to obtain a compound of formula (XIII).

The acid (XIII) is reacted in step b2 with ethylamine, dimethylamine or azetidine according to the conventional methods of peptide coupling to give the compound (XIV), which is deprotected, according to the known methods, to give a compound of formula (V) in which $R_6$=H.

In step d2, the compound (XIV) may be reacted with a $(C_1-C_4)$alkyl halide, in the presence of a base such as a metal hydride or an alkali metal carbonate or alkaline-earth metal carbonate such as $K_2CO_3$ or $Cs_2CO_3$, in an inert solvent such as tetrahydrofuran or N,N-dimethylformamide and at a temperature of between 0° C. and the reflux temperature of the solvent, to give a compound (XV).

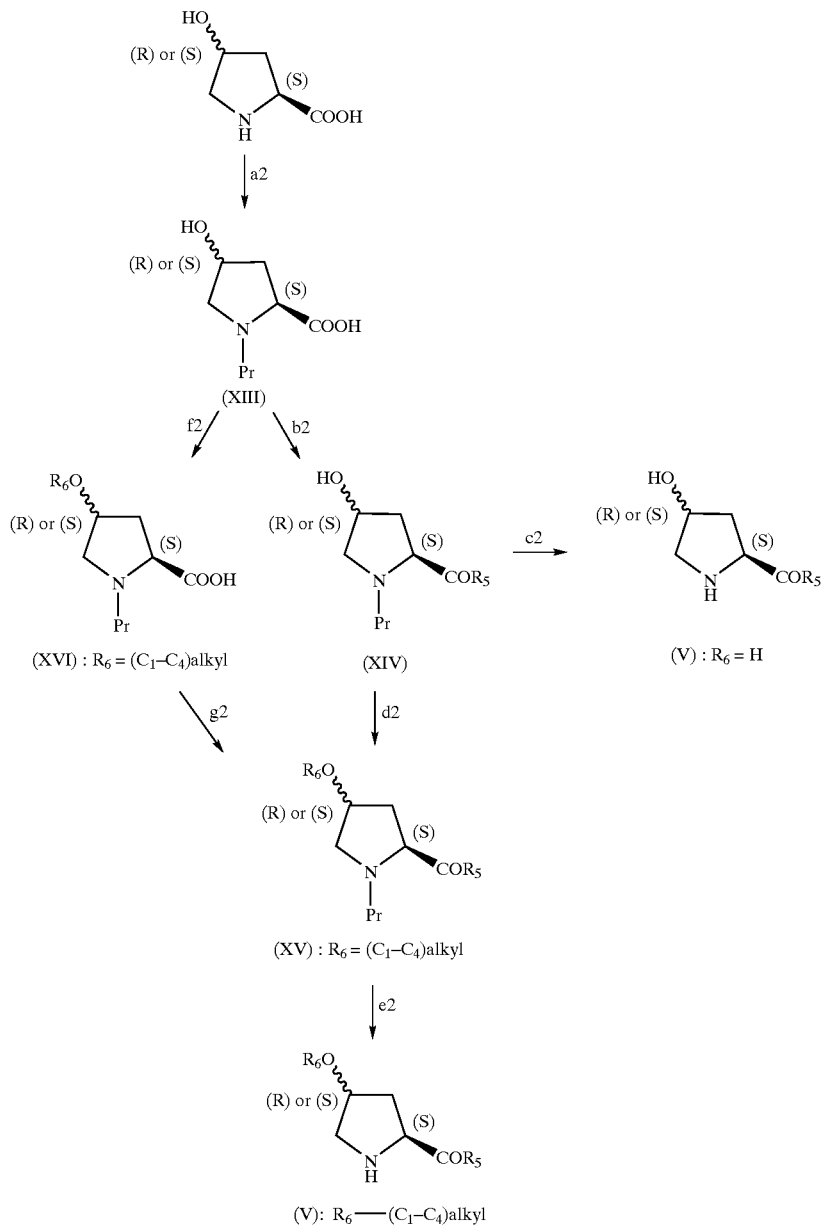

It is also possible to carry out the reaction of a compound (XIV) with a ($C_1$–$C_4$)alkyl halide under conditions of phase-transfer catalysis, in the presence of a base such as an alkali metal hydroxide, for example sodium hydroxide, and of a phase-transfer catalyst such as a substituted quaternary ammonium salt, for example tetrabutylammonium hydrogen sulphate, in an inert solvent such as dichloromethane or benzene as a mixture with water.

Deprotection of the N-protecting group of compound (XV) gives, in step e2, the compounds of formula (V) in which $R_6$=($C_1$–$C_4$)alkyl.

Alternatively, in step f2, the hydroxyl of compound (XIII) is alkylated by reaction with a ($C_1$–$C_4$)alkyl halide under the conditions of step d2, and the acid (XVI) thus obtained is reacted in step g2 with ethylamine, dimethylamine or azetidine according to the conventional methods of peptide coupling to give compound (XV).

(2S,4R)- and (2S,4S)-4-hydroxypyrrolidine-2-carboxylic acid are commercially available.

The compounds of formula (V) in which $R_5$ represents an ethylamino group, a dimethylamino group, an azetidin-1-yl radical or a ($C_1$–$C_2$)alkoxy and $R_6$=—($CH_2$)n-CO—$R_9$ in which n is 1 or 2 and $R_9$ represents a ($C_1$–$C_4$)alkoxy are prepared according to Scheme 3 below in which Pr represents an N-protecting group, in particular benzyloxycarbonyl or tert-butoxycarbonyl.

Scheme 3

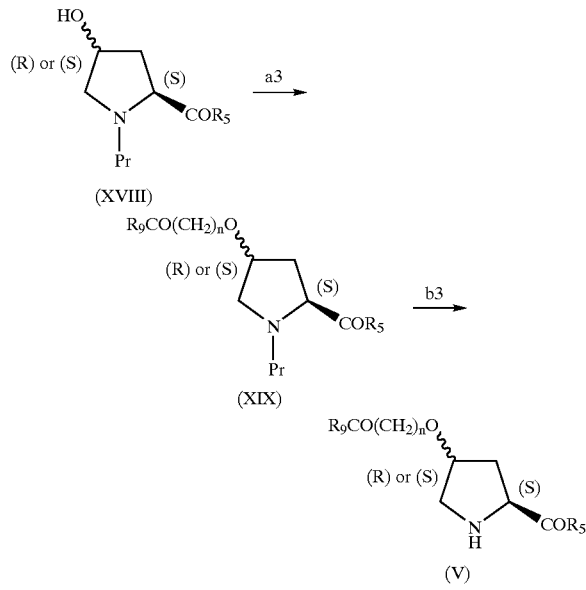

In step a3 of Scheme 3, a compound of formula (XVIII), prepared as described above, is reacted with a compound of formula Hal-($CH_2$)n-$COR_9$ in which Hal represents a halogen atom, preferably chlorine or bromine, n is 1 or 2 and $R_9$ represents a ($C_1$–$C_4$)alkoxy. The reaction is carried out under the conditions described above in step d2 of Scheme 2, to give a compound (XIX).

Deprotection of the N-protecting group of compound (XIX) gives, in step b3, the expected compounds (V).

The compounds of formula (V) in which $R_5$ is as defined for a compound of formula (I) and $R_6$=—($CH_2$)n-CO—$R_9$ in which n is 1 or 2 and $R_9$ represents a hydroxyl are prepared by acidic hydrolysis of a compound of formula (XIX) in which $R_9$ represents a tert-butoxy and Pr represents a benzyloxycarbonyl. The reaction is carried out using a strong acid such as trifluoroacetic acid or hydrochloric acid in a solvent such as dichloromethane or dioxane and at a temperature of between 0° C. and room temperature. Deprotection of the N-protecting group according to the conventional methods gives the expected compounds (V).

The compounds of formula (V) in which $R_5$ is as defined for a compound of formula (I) and $R_6$=—($CH_2$)n-CO—$R_9$ in which n is 1 or 2 and $R_9$ represents a group —$NR_{12}R_{13}$ are prepared by reacting a corresponding compound in which $R_9$ represents a hydroxyl and protected on the nitrogen atom of the pyrrolidine, with an amine $HNR_{12}R_{13}$ according to the conventional methods of peptide coupling.

Deprotection of the N-protecting group according to the conventional methods gives the expected compounds (V).

The compounds of formula (V) in which $R_5$ represents an ethylamino group, a dimethylamino group, an azetidin-1-yl radical or a ($C_1$–$C_2$)alkoxy and $R_6$=—CO—($CH_2$)n-$NR_{10}R_{11}$ in which n is 1 or 2 and $R_{10}$ and $R_{11}$ are as defined for a compound of formula (I) are prepared according to Scheme 4 below in which Pr represents an N-protecting group, in particular benzyloxycarbonyl or tert-butoxycarbonyl.

Scheme 4

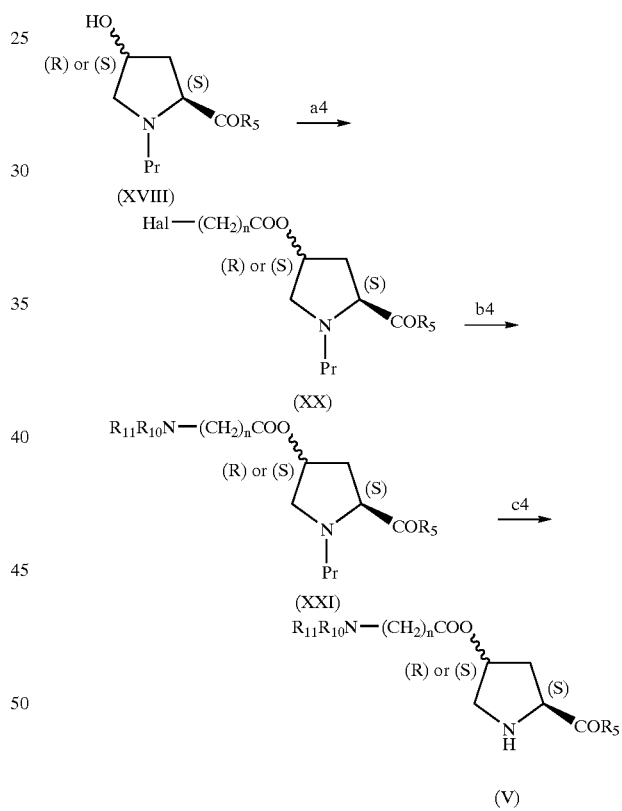

In step a4 of Scheme 4, a compound of formula (XVIII) is reacted with a compound of formula Hal-CO—($CH_2$)n-Hal' in which Hal and Hal' each independently represent a halogen atom, preferably chlorine or bromine, and n is 1 or 2. The reaction is carried out in the presence of a base such as triethylamine or diisopropylethylamine, in a solvent such as dichloromethane or tetrahydrofuran and at a temperature of between 0° C. and the reflux temperature of the solvent.

In step b4, the reaction of the compound of the formula (XX) thus obtained with a compound of formula $HNR_{10}R_{11}$ gives a compound of formula (XXI). The reaction is carried out in the presence of a base such as triethylamine or N,N-diisopropylethylamine, or using an excess of the compound $HNR_{10}R_{11}$, in a solvent such as dichloromethane or tetrahydrofuran and at a temperature of between 0° C. and the reflux temperature of the solvent.

Deprotection of the N-protecting group of compound (XXI) gives, in step c4, the expected compound of formula (V).

In particular, a compound of formula (V) in which $R_6=-CO-(CH_2)n-NR_{10}R_{11}$ in which n is 2 can also be prepared according to Scheme 5 below in which Pr represents an N-protecting group, in particular benzyloxycarbonyl or tert-butoxycarbonyl.

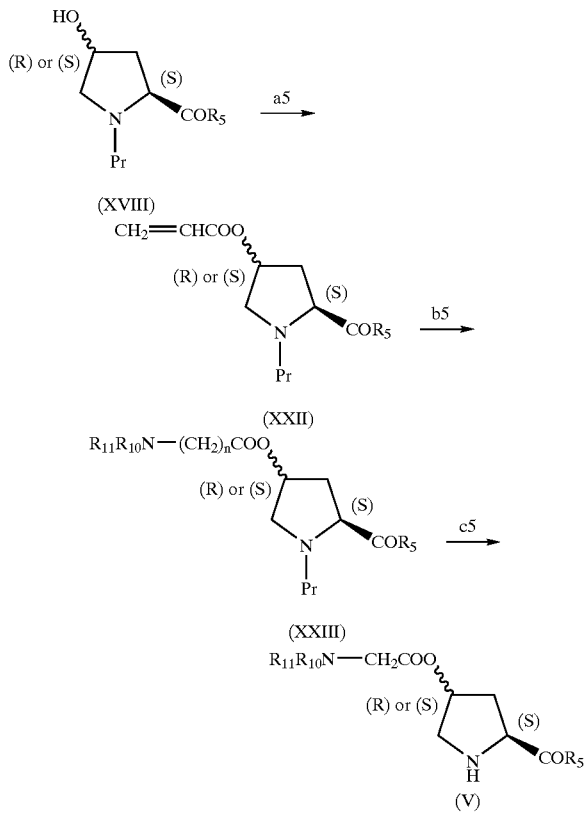

In step a5 of Scheme 5, a compound of formula (XVIII) is reacted with acryloyl chloride, under the conditions described above in step a4 of Scheme 4, to give the compound of formula (XXII).

In step b5, the reaction of compound (XXII) with a compound of formula $HNR_{10}R_{11}$ gives a compound of formula (XXIII). The reaction is carried out in the presence of ferric chloride, in a solvent such as dichloromethane and at a temperature of between room temperature and the reflux temperature of the solvent.

Deprotection of the N-protecting group of compound (XXIII) gives, in step c5, the expected compound of formula (V).

When it is desired to prepare an optically pure compound of formula (I), an optically pure compound of formula (II) is preferably reacted with a compound of formula (III) according to the process of the invention.

The optically pure compounds of formula (II) are prepared by reacting the racemic compound of formula (IV) with an optically pure compound of formula (V), followed by separation of the mixture of diastereoisomers according to the conventional methods, for example by crystallization or chromatography.

Alternatively, the mixture of diastereoisomers of the compound of formula (II) can be reacted with the compound of formula (III) and the mixture of diastereoisomers of the compound of formula (I) thus obtained can be separated.

During any of the steps for preparing the compounds of formula (I) or the intermediate compounds of formula (II), (IV), (V) or (VI), it may be necessary and/or desirable to protect the reactive or sensitive functional groups, such as the amine, hydroxyl or carboxyl groups, present on any of the molecules concerned. This protection may be carried out using conventional protecting groups, such as those described in Protective Groups in Organic Chemistry, J. F. W. McOmie, published by Plenum Press, 1973, in Protective Groups in Organic Synthesis, T. W. Greene and P. G. M. Wuts, published by John Wiley & Sons, 1991 or in Protecting Groups, Kocienski P. J., 1994, Georg Thieme Verlag. The removal of the protecting groups may be carried out in a suitable subsequent step using the methods known to those skilled in the art which do not affect the rest of the molecule concerned.

The N-protecting groups optionally used are the conventional N-protecting groups that are well known to those skilled in the art, such as, for example, the tert-butoxycarbonyl, fluorenylmethoxycarbonyl, benzyl, benzhydrylidene or benzyloxycarbonyl group.

The compounds of formula (II) are novel and form part of the invention.

Thus, according to another of its aspects, a subject of the invention is compounds of formula:

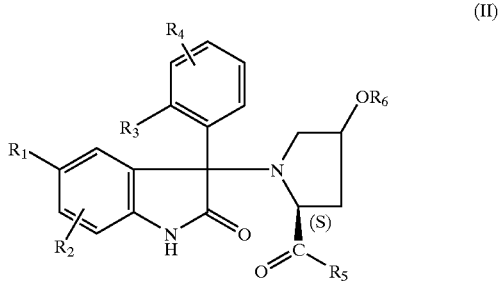

in which:

$R_1$ represents a halogen atom; a $(C_1-C_4)$alkyl; a $(C_1-C_4)$alkoxy; a trifluoromethyl radical; a trifluoromethoxy radical;

$R_2$ represents a hydrogen atom; a halogen atom; a $(C_1-C_4)$alkyl; a $(C_1-C_4)$alkoxy; a trifluoromethyl radical;

or $R_2$ is in position -6- of the indol-2-one ring and $R_1$ and $R_2$ together represent a divalent trimethylene radical;

$R_3$ represents a halogen atom; a hydroxyl; a $(C_1-C_2)$alkyl; a $(C_1-C_2)$alkoxy; a trifluoromethoxy radical;

$R_4$ represents a hydrogen atom; a halogen atom; a $(C_1-C_2)$alkyl; a $(C_1-C_2)$alkoxy;

or $R_4$ is in position -3- of the phenyl and $R_3$ and $R_4$ together represent a methylenedioxy radical;

$R_5$ represents an ethylamino group; a dimethylamino group; an azetidin-1-yl radical; a $(C_1-C_2)$alkoxy;

$R_6$ represents a hydrogen atom; a $(C_1-C_4)$alkyl; a group $-(CH_2)n-CO-R_9$; a group $-CO-(CH_2)n-NR_1OR_{11}$;

$R_9$ represents a hydroxyl; a $(C_1-C_4)$alkoxy; a group $-NR_{12}R_{13}$;

$R_{10}$ and $R_{11}$ each independently represent a $(C_1-C_4)$alkyl;

or $R_{10}$ and $R_{11}$, together with the nitrogen atom to which they are attached, constitute a heterocyclic radical chosen from: azetidin-1-yl, pyrrolidin-1-yl, piperid-1-yl, piperazin-1-yl, morpholin-4-yl or thiomorpholin-4-yl;

$R_{12}$ represents a hydrogen or a $(C_1-C_4)$alkyl;

$R_{13}$ represents a $(C_1-C_4)$alkyl; a —$C(CH_3)_2CH_2OH$ group; a —$C(CH_3)(CH_2OH)_2$ group; a —$C(CH_2OH)_3$ group;

or $R_{12}$ or $R_{13}$, together with the nitrogen atom to which they are attached, constitute a heterocyclic radical chosen from: azetidin-1-yl, pyrrolidin-1-yl, piperid-1-yl, piperazin-1-yl, morpholin-4-yl or thiomorpholin-4-yl;

n is 1 or 2;

as well as the salts thereof with mineral or organic acids, in the form of optically pure isomers or in the form of a mixture of diastereoisomers.

The salts of compounds of formula (II) comprise those with mineral or organic acids which allow a suitable separation or crystallization of the compounds of formula (II) such as the hydrochloride, hydrobromide, oxalate, maleate, succinate, fumarate, citrate or acetate.

The compounds of formula (I) above also comprise those in which one or more hydrogen or carbon atoms have been replaced with their radioactive isotope, for example tritium or carbon-14. Such labelled compounds are useful in metabolic or pharmacokinetic research studies, in biochemical assays as receptor ligands.

The compounds according to the invention have undergone biochemical studies.

The affinity of the compounds of formula (I) according to the invention for the arginine-vasopressin $V_{1b}$ receptors was determined in vitro using the method disclosed by Y. De Keyser et al., Febs Letters, 1994, 356, 215–220. This method consists in studying in vitro the displacement of tritiated arginine-vasopressin ($[^3H]$-AVP) from the $V_{1b}$ receptors present on rat or human adenohypophyseal or cell membrane preparations bearing the $V_{1b}$ receptors. The concentrations of the compounds according to the invention which inhibit 50% ($IC_{50}$) of the binding of the tritiated arginine-vasopressin are low and range from $10^{-6}$ to $10^{-9}$ M, more particularly from $10^{-7}$ to $10^{-9}$ M.

The affinity of the compounds of formula (I) according to the invention for the arginine-vasopressin $V_{1a}$ receptors was determined in vitro using the method disclosed by M. Thibonnier et al., J. Biol. Chem., 1994, 269, 3304–3310. This method consists in studying in vitro the displacement of tritiated arginine-vasopressin ($[^3H]$-AVP) from the $V_{1a}$ receptors present on rat or human cell or membrane preparations bearing the $V_{1a}$ receptors. Among the compounds of formula (I), some also have affinity for the arginine-vasopressin $V_{1a}$ receptors with $IC_{50}$ values which range from 10–6 to $10^{-9}$ M, more particularly from $10^{-7}$ to $10^{-8}$ M.

The affinity of the compounds of formula (I) according to the invention for the vasopressin $V_2$ receptors was also studied (method disclosed by M. Birnbaumer et al., Nature (Lond.), 1992, 357, 333–335). The compounds studied have little or no affinity for the $V_2$ receptors.

Compounds of the present invention are especially active principles of pharmaceutical compositions, the toxicity of which is compatible with their use as medicinal products.

According to another of its aspects, the present invention relates to the use of the compounds of formula (I), or a pharmaceutically acceptable salt, solvate and/or hydrate thereof, for the preparation of medicinal products intended for treating any pathology in which arginine-vasopressin and/or its $V_{1b}$ receptors or both its $V_{1b}$ receptors and its Via receptors are involved.

According to another of its aspects, the present invention relates to the use of compounds of formula (I), or a pharmaceutically acceptable salt, solvate and/or hydrate thereof, for the preparation of medicinal products intended for treating pathologies of the cardiovascular system, of the central nervous system, of the renal system or of the gastric system, as well as small cell lung cancers, obesity, type II diabetes, insulin resistance, hypertriglyceridaemia, of atherosclerosis, Cushing's syndrome, all stress-related pathologies and chronic stress states.

Thus, the compounds according to the invention may be used, in man or animals, in the treatment or prevention of various vasopressin-dependent complaints such as cardio-vascular complaints, for instance hypertension, pulmonary hypertension, cardiac insufficiency, myocardial infarction or coronary vasospasm, in particular in smokers, Raynaud's disease, unstable angina and PTCA (percutaneous transluminal coronary angioplasty), cardiac ischaemia, haemostasis disorders; complaints of the central nervous system such as migraine, cerebral vasospasm, cerebral haemorrhage, cerebral oedema, depression, anxiety, stress, obsessive-compulsive disorder, panic attacks, psychotic states and memory disorders, for example; complaints of the renal system such as renal vasospasm, renal cortex necrosis, nephrogenic diabetes insipidus; complaints of the gastric system such as gastric vasospasm, cirrhosis of the liver, ulcers, vomiting pathology, for example nausea including nausea caused by chemotherapy and travel sickness; diabetic nephropathy. The compounds according to the invention may also be used in the treatment of disorders of sexual behaviour; in women, the compounds according to the invention may be used to treat dysmenorrhoea or premature labour. The compounds according to the invention may also be used in the treatment of small cell lung cancers; hyponatremic encephalopathies; pulmonary syndrome, Meniere's disease; glaucoma, cataracts; obesity; type II diabetes; atherosclerosis; Cushing's syndrome; insulin resistance; hypertriglyceridaemia; in post-operative treatment, in particular after abdominal surgery.

The compounds according to the invention may also be used in the treatment or prevention of all stress-related pathologies such as fatigue and its syndromes, ACTH-dependent disorders, cardiac disorders, pain, changes in gastric emptying, faecal excretion (colitis, irritable bowel syndrome, Crohn's disease), acid secretion, hyperglycaemia, immunosuppression, inflammatory processes (rheumatoid arthritis and osteoarthritis), multiple infections, cancers, asthma, psoriasis, allergies and various neuropsychiatric disorders such as anorexia nervosa, bulimia, mood disorders, depression, anxiety, sleeping disorders, panic attacks, phobias, obsession, pain-perception disorders (fibromyalgia), neurodegenerative diseases (Alzheimer's disease, Parkinson's disease, Huntington's disease), dependency on a substance, haemorrhagic stress, muscular spasms and hypoglycaemia. The compounds according to the invention may also be used in the treatment or prevention of chronic stress states such as immunodepression, fertility disorders and dysfunctions of the hypothalamo-hypophyso-adrenal axis.

The compounds according to the invention may also be used as psychostimulants, bringing about an increase in consciousness and in emotional reactivity towards the environment and facilitating adaptation thereto.

The compounds of formula (I) above, or a pharmaceutically acceptable salt, solvate and/or hydrate thereof, may be used at daily doses of from 0.01 to 100 mg per kilo of body weight of the mammal to be treated, preferably at daily doses of from 0.1 to 50 mg/kg. In man, the dose may preferably range from 0.1 to 4000 mg per day, more particularly from 0.5 to 1000 mg depending on the age of the individual to be treated or the type of treatment: prophylactic or curative.

For their use as medicinal products, the compounds of formula (I) are generally administered in dosage units. The said dosage units are preferably formulated in pharmaceutical compositions in which the active principle is mixed with one or more pharmaceutical excipients.

Thus, according to another of its aspects, the present invention relates to pharmaceutical compositions containing, as active principle, a compound of formula (I), or a pharmaceutically acceptable salt, solvate and/or hydrate thereof.

In the pharmaceutical compositions of the present invention for oral, sublingual, inhaled, subcutaneous, intramuscular, intravenous, transdermal, local or rectal administration, the active principles may be administered in unit administration forms, mixed with conventional pharmaceutical supports, to animals and humans. The appropriate unit administration forms comprise oral forms such as tablets, gel capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

When a solid composition is prepared in the form of tablets or gel capsules, a mixture of pharmaceutical excipients which may be composed of diluents such as, for example, lactose, microcrystalline cellulose, starch, dicalcium phosphate, binders such as, for example, polyvinylpyrrolidone or hydroxypropylmethylcellulose, disintegrating agents such as crosslinked polyvinylpyrrolidone or crosslinked carboxymethylcellulose, flow agents such as silica, talc, lubricants such as magnesium stearate, stearic acid, glyceryl tribehenate or sodium stearyl fumarate is added to the active principle, which may or may not be micronized.

Wetting agents or surfactants such as sodium lauryl sulphate, polysorbate 80 and poloxamer 188 may be added to the formulation.

The tablets may be prepared by various techniques, direct tableting, dry granulation, wet granulation, or hot-melt.

The tablets may be plain or sugar-coated (for example coated with sucrose) or coated with various polymers or other suitable materials.

The tablets may have an immediate, delayed or sustained release by producing polymer matrices or by using specific polymers in the film coating.

The gel capsules may be hard or soft, and film-coated or otherwise, so as to have immediate, sustained or delayed activity (for example via an enteric form).

They may contain not only a solid formulation formulated as above for the tablets but also liquid or semi-solid formulations.

A preparation in the form of a syrup or elixir may contain the active principle together with a sweetener, preferably a calorie-free sweetener, methylparaben and propylparaben as antiseptic, as well as a flavouring and a suitable colorant.

The water-dispersible powders or granules may contain the active principle as a mixture with dispersants, wetting agents or suspending agents, such as polyvinylpyrrolidone, as well as with sweeteners or flavour enhancers.

For rectal administration, use is made of suppositories which are prepared with binders that melt at the rectal temperature, for example cocoa butter or polyethylene glycols.

Aqueous suspensions, isotonic saline solutions or sterile injectable solutions which contain pharmacologically compatible dispersants and/or solubilizing agents, for example propylene glycol, are used for parenteral, intranasal or intraocular administration.

Thus, to prepare an aqueous solution for intravenous injection, a co-solvent such as, for example, an alcohol such as ethanol or a glycol such as polyethylene glycol or propylene glycol, and a hydrophilic surfactant such as polysorbate 80 or poloxamer 188 may be used. To prepare an oily solution for intramuscular injection, the active principle may be dissolved with a triglyceride or a glycerol ester.

Creams, ointments, gels, eye drops and sprays may be used for local administration.

Patches in multilayer form or in a form with a reservoir in which the active principle may be in alcoholic solution, and sprays may be used for transdermal administration.

An aerosol containing, for example, sorbitan trioleate or oleic acid as well as trichlorofluoromethane, dichlorofluoromethane, dichlorotetrafluoroethane, freon substitutes or any other biologically compatible propellent gas is used for administration by inhalation; a system containing the active principle alone or combined with an excipient, in powder form, may also be used.

The active principle may also be in the form of a complex with a cyclodextrin, for example $\alpha,\beta,\gamma$-cyclodextrin or 2-hydroxypropyl-$\beta$-cyclodextrin.

The active principle may also be formulated in the form of microcapsules or microspheres, optionally with one or more supports or additives.

Among the sustained-release forms that are useful in the case of chronic treatments, it is possible to use implants. These may be prepared in the form of an oily suspension or in the form of a suspension of microspheres in an isotonic medium.

In each dosage unit, the active principle of formula (I) is present in the amounts tailored to the daily doses envisaged. In general, each dosage unit is appropriately tailored according to the dosage and the type of administration planned, for example tablets, gel capsules and the like, sachets, ampules, syrups and the like, and drops, such that such a dosage unit contains from 0.1 to 1000 mg of active principle, preferably from 0.5 to 250 mg which is to be administered one to four times a day.

Although these dosages are examples of average situations, there may be particular cases in which higher or lower dosages are appropriate, and such dosages also form part of the invention. According to the usual practice, the dosage which is appropriate for each patient is determined by the doctor according to the mode of administration, age, weight and response of the said patient.

The compositions of the present invention may contain, along with the compounds of formula (I), or a pharmaceutically acceptable salt, solvate and/or hydrate thereof, other active principles which may be useful in the treatment of the disorders or diseases mentioned above.

Thus, a subject of the present invention is also pharmaceutical compositions containing several active principles in combination, one of which is a compound according to the invention.

Thus, according to the present invention, pharmaceutical compositions containing a compound according to the invention combined with a compound acting on the CRF receptors may be prepared.

The compounds according to the invention may also be used to prepare compositions for veterinary use.

The Preparations and Examples which follow illustrate the invention without, however, limiting it.

The following abbreviations are used in the Preparations and in the Examples:

ether: Diethyl ether
iso-ether: Diisopropyl ether
DMF: N,N-Dimethylformamide
THF: Tetrahydrofuran
DCM: Dichloromethane
EtOAc: Ethyl acetate
DIPEA: Diisopropylethylamine
TFA: Trifluoroacetic acid
Boc: tert-Butoxycarbonyl
Cbz: Benzyloxycarbonyl
BOP: Benzotriazol-1-yloxytris(dimethylamino) phosphonium hexafluorophosphate
DCC: 1,3-Dicyclohexylcarbodiimide
HOBT: 1-Hydroxybenzotriazole hydrate
PS-Trisamine: Tris(2-aminoethyl)amine polystyrene 1% crosslinked with divinylbenzene, containing 3.62 millimol of amine function per gram of resin, sold by Argonaut Technologie.
m.p.: Melting point
RT: Room temperature
b.p.: Boiling point
HPLC: High performance liquid chromatography The proton magnetic resonance ($^1$H NMR) spectra are recorded at 200 MHz in DMSO-$d_6$, using the peak for DMSO-$d_6$ as reference. The chemical shifts δ are expressed in parts per million (ppm). The signals observed are expressed as follows: s: singlet; bs: broad singlet; d: doublet; dd: doubled doublet; t: triplate; q: quartet; m: unresolved peak; mt: multiplet.

The mass spectra indicate the value MH$^+$.

Preparations
Preparation of the Compounds of Formula (IV)
Preparation 1.1
3,5-Dichloro-3-(2-methoxyphenyl)-1,3-dihydro-2H-indol-2-one
(IV): $R_1$=Cl; $R_2$=H; $R_3$=OCH$_3$; $R_4$=H; Hal=Cl
A) 5-Chloro-3-hydroxy-3-(2-methoxyphenyl)-1,3-dihydro-2H-indol-2-one This compound is prepared according to the procedure disclosed in WO 95/18105. A solution of 2-methoxyphenylmagnesium bromide is prepared from 16 g of magnesium in 35 ml of ether and from a solution of 124 g of 1-bromo-2-methoxybenzene in 175 ml of ether. This solution is added dropwise, under an argon atmosphere, to a mixture of 30 g of 5-chloro-1H-indole-2,3-dione in 250 ml of THF, cooled beforehand in a bath of ice, and the mixture is then left stirring while allowing the temperature to return to RT. After stirring for one hour at RT, the reaction mixture is poured slowly into saturated NH$_4$Cl solution and the THF is evaporated off under vacuum. The precipitate formed is spin-filtered off and washed with iso-ether. 42 g of the expected product are obtained and are used in the next step without further purification.

B) 3,5-Dichloro-3-(2-methoxyphenyl)-1,3-dihydro-2H-indol-2-one

This compound is prepared according to the procedure disclosed in WO 95/18105. A mixture of 12.71 g of the compound obtained in the preceding step in 105 ml of DCM is cooled to 0° C. and 5.3 ml of pyridine are added, followed by 4.9 ml of thionyl chloride. After stirring for 30 minutes, water is added to the reaction mixture and the DCM is evaporated off under vacuum. The precipitate formed is spin-filtered off, washed three times with water and then three times with iso-ether and dried. 13.66 g of the expected product are obtained and are used without further purification.

Preparation 1.2
3-Bromo-5-chloro-3-(2-chlorophenyl)-1,3-dihydro-2H-indol-2-one
(IV): $R_1$=Cl; $R_2$=H; $R_3$=Cl; $R_4$=H; Hal=Br This compound is prepared according to the procedures disclosed in WO 95/18105 in steps A), B) and C) of Preparation 2.

Preparation 1.3
3-Chloro-5-methyl-3-(2-methoxyphenyl)-1,3-dihydro-2H-indol-2-one
(IV): $R_1$=CH$_3$; $R_2$=H; $R_3$=OCH$_3$; $R_4$=H; Hal=Cl
A) 5-Methyl-3-hydroxy-3-(2-methoxyphenyl)-1,3-dihydro-2H-indol-2-one A solution of 2-methoxyphenylmagnesium bromide is prepared from 6.8 g of magnesium in 15 ml of THF and from a solution of 52.5 g of 1-bromo-2-methoxybenzene in 75 ml of THF. This solution is added dropwise at RT, under an argon atmosphere, to a mixture of 8.9 g of 5-methyl-1H-indole-2,3-dione in 80 ml of THF and is then refluxed for 3 hours. After cooling to RT, saturated NH$_4$Cl solution is added to the reaction mixture, the resulting mixture is extracted three times with EtOAc and the combined organic phases are washed twice with water and with saturated NaCl solution, dried over Na$_2$SO$_4$ and the solvent is partially concentrated. The precipitate formed is spin-filtered off to give 9 g of the expected product.

B) 3-Chloro-5-methyl-3-(2-methoxyphenyl)-1,3-dihydro-2H-indol-2-one

A mixture of 2 g of the compound obtained in the preceding step in 15 ml of DCM is cooled to 0° C. and 0.82 ml of pyridine is added, followed by 0.76 ml of thionyl chloride. After stirring for 20 minutes, water is added to the reaction medium and the DCM is evaporated off under vacuum. The aqueous phase is extracted with EtOAc and the organic phase is washed with water, with saturated NaCl solution and dried over Na$_2$SO$_4$, and the solvent is evaporated off under vacuum. 1.5 g of the expected product are obtained after crystallization from a DCM/iso-ether mixture.

Preparation 1.4
3-Chloro-3-(2-methoxyphenyl)-5-trifluoromethoxy-1,3-dihydro-2H-indol-2-one
(IV): $R_1$=OCF$_3$; $R_2$=H; $R_3$=OCH$_3$; $R_4$=H; Hal=Cl
A) 3-Hydroxy-3-(2-methoxyphenyl)-5-trifluoromethoxy-1,3-dihydro-2H-indol-2-one A solution of 2-methoxyphenylmagnesium bromide is prepared from 1.9 g of magnesium in 4 ml of ether and from a solution of 14.54 g of 1-bromo-2-methoxybenzene in 21 ml of ether. This solution is added dropwise, under an argon atmosphere, to a mixture of 5 g of 5-trifluoromethoxy-1H-indole-2,3-dione in 26 ml of THF, cooled beforehand in an ice bath, and then heated at the reflux point of the ether for 1 hour 30 minutes and allowed to cool to RT. The reaction mixture is poured slowly into saturated NH$_4$Cl solution and extracted with EtOAc, the organic phase is washed with 5% K$_2$CO$_3$ solution, with water and with saturated NaCl solution and dried over Na$_2$SO$_4$, and the solvent is evaporated off under vacuum. 2.8 g of the expected product are obtained.

B) 3-Chloro-3-(2-methoxyphenyl)-5-trifluoromethoxy-1,3-dihydro-2H-indol-2-one

A mixture of 2 g of the compound obtained in the preceding step in 20 ml of DCM is cooled to 0° C., 0.7 g of pyridine is added, followed by 1.05 g of thionyl chloride and the mixture is stirred for 15 minutes. The reaction mixture is concentrated to a volume of 10 ml and this solution is used in this form in Preparations 3.9 and 3.10.

Preparation 1.5

3,5-Dichloro-3-(2-methoxyphenyl)-6-methyl-1,3-dihydro-2H-indol-2-one (IV): $R_1$=Cl; $R_{2=6}$-$CH_3$; $R_3$=$OCH_3$; $R_4$=H; Hal=Cl A) Ethyl 2-(2-methoxyphenyl)-2-oxoacetate A solution of 27 g of 1-bromo-2-methoxybenzene in 270 ml of ether is cooled to −70° C., under an argon atmosphere, 90 ml of a 1.6 M solution of n-butyllithium in pentane are added dropwise and the mixture is then stirred for 45 minutes. 78 ml of diethyl oxalate are added rapidly and the mixture is stirred while allowing the temperature to return to RT. After stirring for 1 hour at RT, saturated $NH_4Cl$ solution is added to the reaction mixture, the phases are separated by settling, the aqueous phase is extracted with ether, the combined organic phases are washed with water, with saturated NaCl solution and dried over $Na_2SO_4$, and the solvents are evaporated off under vacuum. The excess diethyl oxalate is removed by distillation under vacuum (b.p.=87° C. at 2000 Pa). The resulting product is chromatographed on silica gel eluting with a DCM/hexane mixture (50/50; v/v) and then with DCM. The product obtained is purified by distillation under vacuum. 13 g of the expected product are obtained; b.p.=110° C. at 3 Pa.

B) 5-Chloro-3-hydroxy-3-(2-methoxyphenyl)-6-methyl-1,3-dihydro-2H-indol-2-one a) Tert-Butyl 4-chloro-3-methylphenyl-carbamate A mixture of 10 g of 4-chloro-3-methylaniline and 15.26 g of di-tert-butyl dicarbonate in 50 ml of dioxane is stirred for 24 hours at RT. The reaction mixture is concentrated under vacuum and the residue is chromatographed on silica gel, eluting with a gradient of DCM/hexane mixture of from (50/50; v/v) to (70/30; v/v). 5.6 g of the expected product are obtained and are used without further purification.

b) A solution of 5 g of tert-butyl 4-chloro-3-methylphenylcarbamate in 45 ml of ether is cooled to −70° C., under an argon atmosphere, 30 ml of a 1.5 M solution of tert-butyllithium in pentane are added dropwise, the mixture is stirred for 1 hour while allowing the temperature to rise to −10° C., and is stirred for 1 hour 45 minutes at −10° C. The reaction mixture is cooled to −70° C., a solution of 5 g of the compound obtained in step A in 25 ml of THF is added dropwise and the mixture is stirred for 1 hour while allowing the temperature to rise to −30° C., and is then stirred overnight while allowing the temperature to return to RT. Saturated $Na_4Cl$ solution is added to the reaction mixture, the THF is evaporated off, the resulting aqueous phase is extracted three times with EtOAc, the organic phase is washed with water, with saturated NaCl solution and dried over $Na_2SO_4$, the solvent is partially evaporated off and the crystalline product is spin-filtered off. 2.6 g of the expected product are obtained; m.p.=254–256° C.

C) 3,5-Dichloro-3-(2-methoxyphenyl)-6-methyl-1,3-dihydro-2H-indol-2-one

A mixture of 1.25 g of the compound obtained in step B in 20 ml of DCM is cooled to 0° C., 0.51 ml of pyridine is added, followed by 0.47 ml of thionyl chloride, and, after allowing the temperature to return to RT, the mixture is stirred for 1 hour. Water and DCM are added to the reaction mixture and, after separation of the phases by settling, the organic phase is washed four times with water, dried over $Na_2SO_4$ and concentrated under vacuum to a volume of 20 ml, and this solution is used in this form in Preparations 3.11 and 3.12 or 3.31.

Preparation 1.6

3-Chloro-3-(2-chlorophenyl)-5,6-dimethyl-1,3-dihydro-2H-indol-2-one (IV): $R_1$=$CH_3$; $R_2$=6-$CH_3$; $R_3$=Cl; $R_4$=H; Hal=Cl A) N-(3,4-Dimethylphenyl)-D,L-2-chloromandel-amide A mixture of 50 g of 3,4-dimethylaniline and 76.5 g of D,L-2-chloromandelic acid in 250 ml of 1,2-dichlorobenzene is heated at 227° C. for 7 hours, while removing the water formed with the aid of Dean-Stark apparatus. The reaction mixture is concentrated under vacuum to half its volume and is left to crystallize at RT. The crystalline product formed is spin-filtered and washed with iso-ether. 89.42 g of the expected product are obtained, a sample of which is recrystallized from a DCM/iso-ether mixture; m.p.=172–173° C.

B) 3-(2-Chlorophenyl)-5,6-dimethyl-1,3-dihydroindol-2-one 100 ml of 95% sulphuric acid are cooled to −10° C., 12 ml of fuming sulphuric acid (65% oleum) are added dropwise over 30 minutes and the mixture is stirred while allowing the temperature to rise to +10° C. The mixture is cooled again to 0° C., 23.8 g of the compound obtained in the preceding stage are added portionwise over 10 minutes and the resulting mixture is stirred while allowing the temperature to rise, the temperature stabilizing at 29° C. After stirring for 2 hours at RT, the reaction mixture is poured onto ice and the precipitate formed is spin-filtered off. The precipitate is dissolved in 1000 ml of DCM and 200 ml of THF, the pH is brought to 2 by adding solid $K_2CO_3$, this mixture is filtered and the filtrate is concentrated under vacuum. The residue is chromatographed on silica gel, eluting with a gradient of DCM/EtOAc/THF mixture of from (90/10/5; v/v/v) to (80/20/5; v/v/v). 7.72 g of the expected product are obtained; m.p.=231° C.

C) 3-(2-Chlorophenyl)-3-hydroxy-5,6-dimethyl-1,3-dihydroindol-2-one 0.65 g of 60% sodium hydride in oil is added at RT, under an argon atmosphere, to a solution of 4 g of the compound obtained in the preceding step in 70 ml of THF. After the evolution of gas has ceased, 1.7 ml of dimethyl disulphide are added and a stream of air is bubbled into the reaction mixture for 4 hours at RT. The reaction mixture is poured into water, the THF is concentrated under vacuum, the aqueous phase is extracted with EtOAc, the organic phase is washed with water, with saturated NaCl solution and dried over $Na_2SO_4$, the solvent is partially concentrated under vacuum and the crystalline product formed is spin-filtered off. 3.3 g of the expected product are obtained; m.p.=251–253° C.

D) 3-Chloro-3-(2-chlorophenyl)-5,6-dimethyl-1,3-dihydro-2H-indol-2-one

A suspension of 1 g of the compound obtained in the preceding step in 7 ml of DCM is cooled to 0° C., 0.4 ml of pyridine is added, followed by 0.37 ml of thionyl chloride, and the mixture is stirred for 30 minutes. The reaction mixture is diluted by adding 30 ml of DCM, the organic phase is washed with 20 ml of water and dried over $Na_2SO_4$, and the solvent is partially concentrated under vacuum at a temperature below 40° C. This solution is used in this form in Preparations 3.13 and 3.14.

Preparation 1.7
3,5-Dichloro-3-(2,3-dimethoxyphenyl)-1,3-dihydro-2H-indol-2-one (IV): $R_1$=Cl; $R_2$=H; $R_3$=OCH$_3$; $R_4$=3-OCH$_3$; Hal=Cl A) Ethyl 2-(2,3-dimethoxyphenyl)-2-oxoacetate A mixture of 27.6 g of 1,2-dimethoxybenzene in 160 ml of ether is cooled to −40° C., 250 ml of 1.6 M solution of n-butyllithium in hexane are added dropwise and the mixture is then stirred for 24 hours while allowing the temperature to return to RT. The reaction mixture is cooled to −20° C., 136 ml of diethyl oxalate are added quickly and the mixture is stirred while allowing the temperature to return to RT. After stirring for 30 minutes at RT, the reaction mixture is poured into saturated NH$_4$Cl solution, the phases are separated by settling, the aqueous phase is extracted with ether, the combined organic phases are washed twice with water and dried over Na$_2$SO$_4$, and the solvents are evaporated off under vacuum. The excess diethyl oxalate is removed by distillation under vacuum (b.p.=90° C. at 2400 Pa). The resulting crude product is chromatographed on silica gel, eluting with a heptane/iso-ether mixture (90/10; v/v). 25 g of the expected product are obtained and are used in the next step without further purification.

B) 5-Chloro-3-hydroxy-3-(2,3-dimethoxyphenyl)-1,3-dihydro-2H-indol-2-one a) tert-Butyl 4-chlorophenylcarbamate A mixture of 12.7 g of 4-chloroaniline and 22 g of di-tert-butyl dicarbonate in 60 ml of dioxane is stirred at RT for 24 hours. The reaction mixture is concentrated under vacuum, the residue is taken up in pentane and the precipitate formed is spin-filtered off and dried. 22.5 g of the expected product are obtained.

b) A mixture of 11.4 g of tert-butyl 4-chlorophenylcarbamate in 100 ml of ether is cooled to −40° C., under an atmosphere of dry nitrogen, 80 ml of a 1.5 M solution of tert-butyllithium in pentane are added dropwise and the mixture is stirred at −20° C. for 3 hours. The reaction mixture is cooled to −40° C., a solution of 14 g of the compound obtained in step A in 50 ml of THF is added over one hour and the mixture is stirred for 4 days at RT. The reaction mixture is poured into saturated NH$_4$Cl solution and the precipitate formed is spin-filtered off and dried. 10.2 g of the expected product are obtained and are used in the next step without further purification.

C) 3,5-Dichloro-3-(2,3-dimethoxyphenyl)-1,3-dihydro-2H-indol-2-one 0.8 ml of pyridine and then 1.2 ml of thionyl chloride are added, at RT, to a mixture of 2 g of the compound obtained in step B in 50 ml of DCM, and the mixture is stirred until dissolution is complete. The reaction mixture is washed with 1N HCl solution and then twice with water and dried over Na$_2$SO$_4$, and the solvent is evaporated off under vacuum. The residue is chromatographed on silica gel, eluting with a DCM/EtOAc mixture (95/5; v/v). 1.2 g of the expected product are obtained and are used without further purification.

Preparation 1.8
3,5-Dichloro-3-(2-methoxyphenyl)-6-trifluoromethyl-1,3-dihydro-2H-indol-2-one (IV): $R_1$=Cl; $R_2$=6-CF$_3$; $R_3$=OCH$_3$; $R_4$=H; Hal=Cl A) 5-Chloro-3-hydroxy-3-(2-methoxyphenyl)-6-trifluoromethyl-1,3-dihydro-2H-indol-2-one a) tert-Butyl 4-chloro-3-trifluoromethyl-phenylcarbamate This compound is prepared according to the procedure described in step B a) of Preparation 1.5, from 4-chloro-3-trifluoromethylaniline and di-tert-butyl dicarbonate in dioxane. The expected product is obtained in the form of an oil which solidifies; m.p.=90° C.

b) A solution of 4 g of tert-butyl 4-chloro-3-trifluoromethylphenylcarbamate in 30 ml of ether is cooled to −70° C., under an argon atmosphere, 22 ml of a 1.5 M solution of tert-butyllithium in pentane are added dropwise and the mixture is stirred for 1 hour while allowing the temperature to rise to −10° C. and is stirred for 2 hours 30 minutes at −10° C. The reaction mixture is cooled to −70° C., a solution of 3.05 g of the compound obtained in step A of Preparation 1.5 in 15 ml of THF is added dropwise and the mixture is stirred for 1 hour while allowing the temperature to rise to −30° C. and then for 16 hours while allowing the temperature to return to RT. Saturated NH$_4$Cl solution is added to the reaction mixture, the ether and THF are evaporated off, the resulting aqueous phase is extracted with EtOAc, the organic phase is washed with water, with saturated NaCl solution and dried over Na$_2$SO$_4$, and the solvent is evaporated off under vacuum. The residue is chromatographed on silica gel, eluting with DCM and then with a DCM/EtOAc mixture (90/10; v/v). 1.48 g of the expected product are obtained after crystallization from an iso-ether/hexane mixture; m.p.=230–231° C.

B) 3,5-Dichloro-3-(2-methoxyphenyl)-6-trifluoromethyl-1,3-dihydro-2H-indol-2-one A suspension of 1.3 g of the compound obtained in step A in 8 ml of DCM is cooled to 0° C., 0.43 ml of pyridine and then 0.4 ml of thionyl chloride are added and the mixture is stirred for 15 minutes. The reaction mixture is washed three times with water, the organic phase is dried over Na$_2$SO$_4$ and the solvent is partially evaporated off under vacuum down to a volume of 10 ml. This solution is used in this form in Preparations 3.17 and 3.18.

Preparation 1.9
3,5-Dichloro-3-(2-chlorophenyl)-6-methoxy-1,3-dihydro-2H-indol-2-one (IV): $R_1$=Cl; $R_2$=6-OCH$_3$; $R_3$=Cl; $R_4$=H; Hal=Cl A) 4-Chloro-3-methoxyaniline A mixture of 36 g of 2-chloro-5-nitroanisole and Raney® nickel in 150 ml of MeOH and 200 ml of THF is hydrogenated in Par apparatus for 4 hours, at 35° C. and at a pressure of 1.3 bar. The catalyst is filtered off on Celite® and the filtrate is concentrated under vacuum. 28 g of the expected product are obtained, and are used without further purification.

B) N-(4-Chloro-3-methoxyphenyl)-D,L-2-chloromandelamide

A mixture of 28 g of the compound obtained in the preceding step and 33.13 g of D,L-2-chloromandelic acid in 128 ml of 1,2-dichlorobenzene is heated at 230° C. for 4 hours, while removing the water formed with the aid of Dean-Stark apparatus. The reaction mixture is partially concentrated under vacuum and left to crystallize. The crystalline product formed is spin-filtered off and washed with iso-ether. 40 g of the expected product are obtained.

C) 5-Chloro-3-(2-chlorophenyl)-6-methoxy-1,3-dihydro-2H-indol-2-one 40 g of the compound obtained in the preceding step are added rapidly to 550 g of polyphosphoric acid, the mixture is then heated at 60° C. for 8 hours and is left stirring overnight while allowing the temperature to return to RT. Ice-water is added to the reaction mixture and the precipitate formed is spin-filtered off and washed with water. The precipitate is taken up in EtOAc and, after slurrying, the white product obtained is spin-filtered off and washed with iso-ether. 17.2 g of the expected product are obtained; m.p.=243–247° C.

D) 5-Chloro-3-(2-chlorophenyl)-3-hydroxy-6-methoxy-1,3-dihydro-2H-indol-2-one 2.56 g of 60% sodium hydride in oil are added at RT, under an argon atmosphere, to a solution of 17.2 g of the compound obtained in the preceding step in 220 ml of THF. After the evolution of gas has ceased, 6.85 g of dimethyl disulphide are added, air is bubbled into the reaction mixture and the mixture is stirred at RT for 72 hours. Water is added to the reaction mixture, the THF is evaporated off under vacuum, the remaining aqueous phase is extracted with EtOAc, the organic phase is washed with water, with saturated NaCl solution and dried over $Na_2SO_4$, and the solvent is evaporated off under vacuum. The product obtained is dissolved in DCM, the solvent is partially concentrated, the product is allowed to crystallize and the crystalline product formed is spin-filtered off. 6 g of the expected product are obtained; m.p.=237–240° C.

E) 3,5-Dichloro-3-(2-chlorophenyl)-6-methoxy-1,3-dihydro-2H-indol-2-one

A suspension of 1.5 g of the compound obtained in the preceding step in 20 ml of DCM is cooled in an ice bath, 0.375 ml of pyridine and then 0.33 ml of thionyl chloride are added and the mixture is stirred for 30 minutes. At the end of the reaction, a suspension of the expected product which has precipitated in the DCM is obtained and this suspension is used directly in Preparations 3.19 and 3.20.

Preparation 1.10

3,6-Dichloro-3-(2-methoxyphenyl)-5-methyl-1,3-dihydro-2H-indol-2-one (IV): $R_1=CH_3$; $R_2=6$-Cl; $R_3=OCH_3$; $R_4=H$; Hal=Cl A) 6-Chloro-5-methyl-3-methylthio-1,3-dihydro-2H-indol-2-one and 4-chloro-5-methyl-3-methylthio-1,3-dihydro-2H-indol-2-one 8.5 ml of chlorine are introduced into 320 ml of DCM cooled to −70° C., followed by addition, over 20 minutes and at −70° C., of a solution of 24 ml of ethyl methylthioacetate in 60 ml of DCM, and the mixture is stirred for 15 minutes at −70° C. A solution of 52.64 g of 3-chloro-4-methylaniline in 100 ml of DCM is then added, at −70° C. and over 30 minutes, and is stirred for 1 hour 45 minutes at −70° C. Finally, 41.3 ml of triethylamine are added, at −70° C., and the mixture is stirred for 1 hour while allowing the temperature to return to RT. The reaction mixture is washed twice with 250 ml of water, the organic phase is dried over $MgSO_4$ and the solvent is evaporated off under vacuum. The residue is taken up in a mixture of 600 ml of ether and 130 ml of 2N HCl, and is stirred for 72 hours at RT. An insoluble product is filtered off, the phases of the filtrate are allowed to separate by settling, the organic phase is washed twice with water and dried over $MgSO_4$, and the solvent is evaporated off under vacuum. The residue is chromatographed on silica gel, eluting with DCM and then with a DCM/EtOAc mixture (85/15; v/v). The mixture obtained is re-chromatographed on silica gel, eluting with DCM and then with a DCM/EtOAc mixture (95/5; v/v). The two isomers are separated.

1.16 g of the less polar isomer, which is 6-chloro-5-methyl-3-methylthio-1,3-dihydro-2H-indol-2-one, are obtained, 0.72 g of the more polar isomer, which is 4-chloro-5-methyl-3-methylthio-1,3-dihydro-2H-indol-2-one, is obtained.

E) 6-Chloro-5-methyl-1H-indole-2,3-dione

A mixture of 1.16 g of 6-chloro-5-methyl-3-methylthio-1,3-dihydro-2H-indol-2-one obtained in the preceding step and 0.681 g of N-chlorosuccinimide in 100 ml of carbon tetrachloride is refluxed for 1 hour. The reaction mixture is concentrated under vacuum and the residue is taken up in a mixture of 80 ml of THF and 20 ml of water and then refluxed for 16 hours. The THF is evaporated off under vacuum, the remaining aqueous phase is extracted with EtOAc, the organic phase is washed with water, with saturated NaCl solution and dried over $Na_2SO_4$, and the solvent is evaporated off under vacuum. The residue is chromatographed on silica gel, eluting with DCM and then with a gradient of DCM/EtOAc mixture down to (85/15; v/v). 0.793 g of the expected product is obtained; m.p.=264° C.

C) 6-Chloro-3-hydroxy-3-(2-methoxyphenyl)-5-methyl-1,3-dihydro-2H-indol-2-one

A solution of 2-methoxyphenylmagnesium bromide is prepared from 0.687 g of magnesium in 1.5 ml of ether and from a solution of 5.35 g of 1-bromo-2-methoxybenzene in 7.55 ml of ether. This solution is added dropwise, under an argon atmosphere, to a mixture of 1.4 g of the compound obtained in the preceding step in 14 ml of THF cooled beforehand in an ice bath, and the mixture is then stirred while allowing the temperature to return to RT. After stirring for 1 hour at RT, the reaction mixture is poured slowly into saturated $NH_4Cl$ solution, the THF is evaporated off under vacuum, the aqueous phase is extracted with EtOAc, the organic phase is washed with water, with saturated NaCl solution and dried over $Na_2SO_4$ and the EtOAc is evaporated off under vacuum. The residue is chromatographed on silica gel, eluting with DCM and then with a DCM/MeOH mixture (98/2; v/v). 1.6 g of the expected product are obtained after crystallization from a THF/MeOH mixture; m.p.=266° C.

D) 3,6-Dichloro-3-(2-methoxyphenyl)-5-methyl-1,3-dihydro-2H-indol-2-one

A suspension of 2.5 g of the compound obtained in the preceding step in 15 ml of DCM is cooled in an ice bath, 1 ml of pyridine and then 1.09 ml of thionyl chloride are added and the mixture is stirred for 2 hours. The reaction mixture is partially concentrated under vacuum down to a volume of 10 ml and this solution is used in this form in Preparations 3.21 and 3.22.

Preparation 1.11

3-Bromo-5,6-dichloro-3-(2-chlorophenyl)-1,3-dihydro-2H-indol-2-one (IV): $R_1=Cl$; $R_2=6$-Cl; $R_3=Cl$; $R_4=H$; Hal=Br This compound is prepared according to the procedures disclosed in WO 95/18105 in steps A), B) and C) of Preparation 72.

Preparation 1.12

3,5-Dichloro-3-(2-ethoxyphenyl)-1,3-dihydro-2H-indol-2-one (IV): $R_1=Cl$; $R_2=H$; $R_3=OCH_2CH_3$; $R_4=H$, Hal=Cl A) 1-Bromo-2-ethoxybenzene A mixture of 17.5 g of 2-bromophenol, 66 ml of diethyl sulphate and 170 ml of 10% NaOH solution is refluxed for 2 hours. After cooling the reaction mixture to RT, it is extracted with EtOAc, the organic phase is washed with 2N NaOH solution and dried over $Na_2SO_4$, and the solvent is evaporated off under vacuum. 19.6 g of the expected product are obtained.

B) 5-Chloro-3-(2-ethoxyphenyl)-3-hydroxy-1,3-dihydro-2H-indol-2-one

A solution of 2-ethoxyphenylmagnesium bromide is prepared from 2.2 g of magnesium in 10 ml of ether and from a solution of 16.5 g of the compound obtained in the preceding step in 40 ml of ether. This solution is added dropwise and under a nitrogen atmosphere to a mixture of 5 g of 5-chloro-1H-indole-2,3-dione in 20 ml of THF, while keeping the temperature of the reaction medium below 35°

C. After stirring for 2 hours at RT, the reaction mixture is poured into 200 ml of 2N HCl, the mixture is extracted with EtOAc, the organic phase is dried over $Na_2SO_4$ and the solvents are evaporated off under vacuum. The residue is taken up in hot iso-ether and left to crystallize. The crystalline product formed is spin-filtered off, washed with iso-ether and dried. 5.7 g of the expected product are obtained; m.p.=251° C.

C) 3,5-Dichloro-3-(2-ethoxyphenyl)-1,3-dihydro-2H-indol-2-one 1 ml of thionyl chloride is added, at RT, to a mixture of 3 g of the compounds obtained in the preceding step and 2 ml of pyridine in 50 ml of DCM, and the mixture is stirred for 1 hour at RT. The reaction mixture is chromatographed on silica gel, eluting with DCM. 2.4 g of the expected product are obtained after crystallization from iso-ether; m.p.=198° C.

Preparation 1.13
3,5-Dichloro-3-(2-trifluoromexothyphenyl)-1,3-dihydro-2H-indol-2-one (IV): $R_1$=Cl; $R_2$=H; $R_3$=$OCF_3$; $R_4$=H, Hal=Cl A) 5-Chloro-3-hydroxy-3-(2-trifluoromethoxyphenyl)-1,3-dihydro-2H-indol-2-one A solution of 25 g of 1-bromo-2-trifluoromethoxybenzene in 130 ml of ether is added dropwise to a mixture of 2.8 g of magnesium in 20 ml of ether, and once the refluxing has started it is maintained. At the end of the addition the mixture is refluxed for 1 hour. A mixture of 7.5 g of 5-chloro-1H-indole-2,3-dione in 100 ml of THF is then added, at a temperature below 40° C., followed by refluxing for 1 hour. After cooling to RT, the reaction mixture is poured into an ice/concentrated HCl mixture, the resulting mixture is extracted with EtOAc, the organic phase is washed with water, with 1N NaOH solution and dried over $Na_2SO_4$, and the solvent is evaporated under vacuum. 6.5 g of the expected product are obtained after crystallization from a DCM/iso-ether mixture (20/80; v/v); m.p.=214° C.

B) 3,5-Dichloro-3-(2-trifluoromethoxyphenyl)-1,3-dihydro-2H-indol-2-one 0.7 ml of thionyl chloride is added, at a temperature below 20° C., to a mixture of 2.7 g of the compound obtained in the preceding step and 1 ml of pyridine in 20 ml of DCM, and the mixture is stirred for 1 hour. The reaction mixture is washed twice with water, the organic phase is dried over Na2SO4 and the solvent is evaporated off under vacuum. 1.8 g of the expected product are obtained after crystallization from iso-ether; m.p.=185° C.

Preparation 1.14
3,5-Dichloro-3-(2,3-difluorophenyl)-1,3-dihydro-2H-indol-2-one (IV): $R_1$=Cl; $R_2$=H; $R_3$=F; $R_4$=3-F; Hal=Cl A) 5-Chloro-3-(2,3-difluorophenyl)-3-hydroxy-1,3-dihydro-2H-indol-2-one A solution of 5.6 g of 1,2-difluorobenzene in 50 ml of ether is cooled to −10° C., 31 ml of a 1.6 M solution of n-butyllithium in hexane are added dropwise and the mixture is stirred at −10° C. for 2 hours. The reaction mixture is cooled to −50° C., a solution of 4 g of 5-chloro-1H-indole-2,3-dione in 40 ml of THF is added and the resulting mixture is stirred for 12 hours, while allowing the temperature to return to RT. The reaction mixture is poured into a concentrated HCl/ice/water mixture, the resulting mixture is extracted with EtOAc, the organic phase is washed with 1N NaOH solution, with water and dried over $Na_2SO_4$, and the solvent is evaporated off under vacuum. 2.8 g of the expected product are obtained after crystallization from iso-ether; m.p.=248° C.

B) 3,5-Dichloro-3-(2,3-difluorophenyl)-1,3-dihydro-2H-indol-2-one 0.9 ml of thionyl chloride is added to a mixture of 2.8 g of the compound obtained in the preceding step and 1 ml of pyridine in 30 ml of DCM, and the mixture is stirred for 1 hour at RT. The reaction mixture is washed twice with water and dried over $Na_2SO_4$, and the solvent is evaporated off under vacuum. The residue is chromatographed on silica gel, eluting with DCM. 0.9 g of the expected product is obtained.

Preparation 1.15
3,5-Dichloro-3-(2,4-dimethoxyphenyl)-1,3-dihydro-2H-indol-2-one (IV): $R_1$=Cl; $R_2$=H; $R_3$=$OCH_3$; $R_4$=4-$OCH_3$; Hal=Cl A) 5-Chloro-3-hydroxy-3-(2,4-dimethoxyphenyl)-1,3-dihydro-2H-indol-2-one A solution of 2,4-dimethoxyphenylmagnesium bromide is prepared from 2.2 g of magnesium in 10 ml of THF and from a solution of 18 g of 1-bromo-2,4-dimethoxybenzene in 40 ml of THF. This solution is added dropwise to a mixture of 5 g of 5-chloro-1H-indole-2,3-dione in 50 ml of THF at a temperature of 30° C., and the mixture is then refluxed for 2 hours. The reaction mixture is cooled to RT and poured into saturated $NH_4Cl$ solution, this mixture is extracted with EtOAc, the organic phase is washed with water and dried over $Na_2SO_4$, and the solvent is evaporated off under vacuum. 7.2 g of the expected product are obtained after crystallization from hot iso-ether.

B) 3,5-Dichloro-3-(2,4-dimethoxyphenyl)-1,3-dihydro-2H-indol-2-one

A mixture of 2.5 g of the compound obtained in the preceding step and 0.6 ml of pyridine in 20 ml of DCM is cooled to a temperature below 10° C., 0.6 ml of thionyl chloride is added dropwise and the mixture is stirred for 15 minutes. The reaction mixture is washed twice with water and dried over $Na_2SO_4$, and the solvent is evaporated off under vacuum. The expected product is obtained, and is used in this form in Preparations 3.38 and 3.39.

Preparation 1.16
3,5-Dichloro-3-(1,3-benzodioxol-4-yl)-1,3-dihydro-2H-indol-2-one (IV): $R_1$=Cl; $R_2$=H; $R_3$+$R_4$ 2,3-O—$CH_2$—O—; Hal=Cl A) 4-Bromo-1,3-benzodioxol This compound is prepared according to the process disclosed in Tetrahedron Lett., 1995, 36, 6413–6414.

B) 5-Chloro-3-(1,3-benzodioxol-4-yl)-3-hydroxy-1,3-dihydro-2H-indol-2-one

A solution of 1,3-benzodioxol-4-ylmagnesium bromide is prepared from 0.85 g of magnesium in 10 ml of THF and from a solution of 6.7 g of the compound obtained in the preceding step in 40 ml of THF. This solution is added dropwise and at a temperature below 40° C. to a mixture of 3 g of 5-chloro-1H-indole-2,3-dione in 50 ml of THF and the resulting mixture is then stirred for 1 hour. The reaction mixture is poured into saturated $NH_4Cl$ solution, the resulting mixture is extracted with EtOAc, the organic phase is washed with water and dried over $Na_2SO_4$, and the solvent is evaporated off under vacuum. 1.12 g of the expected product are obtained after crystallization from DCM; m.p.=271° C.

C) 3,5-Dichloro-3-(1,3-benzodioxol-4-yl)-1,3-dihydro-2H-indol-2-one 0.3 ml of thionyl chloride is added, at a temperature below 25° C., to a mixture of 1.1 g of the compound obtained in the preceding step and 0.4 ml of pyridine in 20 ml of DCM, and the mixture is stirred for 30 minutes. The reaction mixture is washed twice with water, the organic phase is dried over $Na_2SO_4$ and the solvent is evaporated off under vacuum.

0.62 g of the expected product is obtained after crystallization from DCM; m.p.=241° C.

Preparation 1.17

3,5,6-Trichloro-3-(2-methoxyphenyl)-1,3-dihydro-2H-indol-2-one (IV): $R_1$=Cl; $R_2$=6-Cl; $R_3$=OCH$_3$; $R_4$=H; Hal=Cl A) 5,6-Dichloro-1H-indole-2,3-dione This compound is prepared according to the procedure disclosed in J. Am. Chem. Soc., 1946, 68, 2697–2703 or according to the procedure disclosed in J. Org. Chem., 1952, 17, 149–156.

B) 5,6-Dichloro-3-hydroxy-3-(2-methxyphenyl)-1,3-dihydro-2H-indol-2-one 5.57 g of 1-bromo-2-methoxybenzene are added dropwise to a suspension of 0.72 g of magnesium in 15 ml of ether containing a few crystals of iodine, and the refluxing is maintained once it has started. At the end of the addition, the mixture is refluxed for 2 hours. A suspension of 2.7 g of 5,6-dichloro-1H-indole-2,3-dione in 30 ml of THF is then added and this mixture is refluxed for 30 minutes. After cooling to RT, the reaction mixture is poured into a water/ice/concentrated HCl mixture, the resulting mixture is extracted with EtOAc, the organic phase is dried over Na$_2$SO$_4$ and the solvent is evaporated off under vacuum. The residue is slurried in hot iso-ether and the precipitate formed is spin-filtered off and washed with ether. 3 g of the expected product are obtained.

C) 3,5,6-Trichloro-3-(2-methoxyphenyl)-1,3-dihydro-2H-indol-2-one

A suspension of 1.5 g of the compound obtained in the preceding step in 30 ml of DCM is cooled in an ice bath, and 0.56 ml of pyridine is added, followed by 0.5 ml of thionyl chloride. After stirring for 1 hour at RT, the reaction mixture is diluted by addition of DCM, the organic phase is washed with water to neutral pH and dried over Na$_2$SO$_4$, and the solvent is evaporated off under vacuum. 1.5 g of the expected product are obtained in the form of a foam which is used in this form.

Preparation of the compounds of formula (V).

Preparation 2.1 a)

(2S,4R)-4-Hydroxy-N,N-dimethyl-2-pyrrolidinecarboxamide Hydrochloride (V), HCl: $R_5$=N(CH$_3$)$_2$; $R_6$=H A) (2S,4R)-1-(tert-Butoxycarbonyl)-4-hydroxy-N,N-dimethyl-2-pyrrolidinecarboxamide A mixture of 11.2 g of (2S,4R)-1-(tert-butoxycarbonyl)-4-hydroxy-2-pyrrolidinecarboxylic acid in 50 ml of DCM is cooled to 0° C., 8.45 ml of DIPEA and then 21.2 g of BOP are added and the resulting mixture is stirred for 10 minutes. Dimethylamine gas is then added by sparging and the mixture is stirred for 3 hours at RT. The reaction mixture is partially concentrated under vacuum to a volume of 20 ml and an insoluble material is filtered off. The filtrate is chromatographed on silica gel, eluting with a DCM/MeOH mixture (94/6; v/v) and the product obtained is re-chromatographed on alumina, eluting with a DCM/MeOH mixture (96/4; v/v). 11.1 g of the expected product are obtained.

B) (2S,4R)-4-Hydroxy-N,N-dimethyl-2-pyrrolidinecarboxamide Hydrochloride

A mixture of 6.9 g of the compound obtained in the preceding step in 69 ml of a 4N solution of HCl in ether is stirred for 2 hours at RT. The reaction mixture is concentrated under vacuum, the residue is taken up in ether and the solvent is evaporated off under vacuum, this operation being repeated several times. 4 g of the expected product are obtained.

Preparation 2.1 b)

(2S,4R)-4-Hydroxy-N,N-dimethyl-2-pyrrolidinecarboxamide Trifluoroacetate (V), CF$_3$COOH: $R_5$=N(CH$_3$)$_2$; $R_6$=H A solution of 2.1 g of the compound obtained in step A of Preparation 2.1 a) in 5 ml of DCM is cooled to 0° C., 10 ml of trifluoroacetic acid are added and this mixture is stirred for 2 hours at RT. The reaction mixture is concentrated under vacuum, the residue is taken up in DCM and the solvent is evaporated off under vacuum, this operation being repeated several times. The expected product is obtained, and is used directly in Preparations 3.1 and 3.2.

Preparation 2.2

(2S,4R)-2-(Azetidin-1-ylcarbonyl)-4-hydroxypyrrolidine (V):

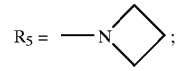

$R_6$=H.

A) (2S,4R)-1-(Benzyloxycarbonyl)-2-(azetidin-1-ylcarbonyl)-4-hydroxypyrrolidine

A solution of 5 g of (2S,4R)-(benzyloxycarbonyl)-4-hydroxy-2-pyrrolidinecarboxylic acid in 50 ml of DCM and 10 ml of DMF is prepared, 2.7 g of HOBT and then 4.15 g of DCC are added and the resulting mixture is stirred for 10 minutes at RT. The reaction mixture is cooled to 0° C., 2 g of azetidine are added and this mixture is stirred for 12 hours, while allowing the temperature to return to RT. The precipitate formed is filtered off, the filtrate is washed twice with saturated Na$_2$CO$_3$ solution, the organic phase is dried over Na$_2$SO$_4$ and the solvent is evaporated off under vacuum. The oil obtained is chromatographed on silica gel, eluting with a DCM/MeOH mixture (95/5; v/v). 2.1 g of the expected product are obtained.

B) (2S,4R)-2-(Azetidin-1-ylcarbonyl)-4-hydroxypyrrolidine 1.8 g of the compound obtained in the preceding step and 0.58 g of 10% palladium-on-charcoal in 80 ml of EtOH is hydrogenated overnight at RT and at atmospheric pressure. The catalyst is filtered off on Celite® and the filtrate is concentrated under vacuum. 0.9 g of the expected product is obtained.

Preparation 2.3

(2S,4R)-4-Methoxy-N,N-dimethyl-2-pyrrolidinecarboxamide Hydrochloride (V), HCl: $R_5$=N(CH$_3$)$_2$; $R_6$=CH$_3$ A) (2S,4R)-1-(tert-Butoxycarbonyl)-4-methoxy-N,N-dimethyl-2-pyrrolidinecarboxamide A solution of 6.5 g of the compound obtained in step A of Preparation 2.1 a) in 70 ml of THF is cooled to 0° C., 1.2 g of 60% sodium hydride in oil are added portionwise and the mixture is stirred for 30 minutes at 0° C. A solution of 2.35 ml of methyl iodide in 10 ml of THF is then added dropwise and the mixture is stirred for 2 hours, while allowing the temperature to return to RT. 5 drops of water are added and the reaction mixture is neutralized by addition of concentrated HCl and is concentrated under vacuum. The residual water is removed azeotropically by addition of benzene and the resulting mixture is concentrated under vacuum. The residue is chromatographed on silica gel, eluting with a DCM/MeOH mixture (96/4; v/v). 6.1 g of the expected product are obtained.

B) (2S,4R)-4-Methoxy-N,N-dimethyl-2-pyrrolidinecarboxamide hydrochloride

A mixture of 6.1 g of the compound obtained in the preceding step and 65 ml of a 4N solution of HCl in ether is stirred for 2 hours. The reaction mixture is concentrated under vacuum, the residue is taken up in DCM and the solvent is evaporated off under vacuum, this operation being repeated several times. 4.45 g of the expected product are obtained.

Preparation 2.4

(2S,4R)-4-Ethoxy-N,N-dimethyl-2-pyrrolidinecarboxamide Trifluoroacetate (V), $CF_3COOH$: $R_5=N(CH_3)_2$; $R_6=\!\!-\!\!CH_2CH_3$ A) (2S,4R)-1-(tert-Butoxycarbonyl)-4-ethoxy-2-pyrrolidinecarboxylic Acid 1.72 g of 60% sodium hydride in oil are added, under a nitrogen atmosphere, to a solution of 5 g of (2S,4R)-1-(tert-butoxycarbonyl)-4-hydroxy-2-pyrrolidinecarboxylic acid in 100 ml of THF, and the mixture is stirred for 45 minutes at RT. 3.27 g of ethyl iodide are then added, the mixture is refluxed for 3 hours and stirred for 18 hours while allowing the temperature to return to RT. The reaction mixture is concentrated under vacuum, the residue is taken up in 5% $KHSO_4$ solution and extracted with EtOAc, the organic phase is dried over $Na_2SO_4$ and the solvent is evaporated off under vacuum. 4.5 g of the expected product are obtained in the form of an oil.

B) (2S,4R)-1-(tert-Butoxycarbonyl)-4-ethoxy-N,N-dimethyl-2-pyrrolidinecarboxamide 3.5 g of triethylamine and then 7.6 g of BOP are added to a solution of 4.5 g of the compound obtained in the preceding step in 100 ml of DCM, and this mixture is stirred for 15 minutes at RT. Dimethylamine gas is then added by sparging and the mixture is stirred for 3 hours at RT. The reaction mixture is concentrated under vacuum, the residue is extracted with EtOAc, the organic phase is washed with 5% $Na_2CO_3$ solution, with 5% $KHSO_4$ solution and dried over $Na_2SO_4$, and the solvent is evaporated off under vacuum. The residue is chromatographed on silica gel, eluting with a DCM/MeOH mixture (95/5; v/v). 2 g of the expected product are obtained in the form of an oil.

C) (2S,4R)-4-Ethoxy-N,N-dimethyl-2-pyrrolidinecarboxamide Trifluoroacetate

A solution of 2 g of the compound obtained in the preceding step in 10 ml of DCM is cooled to 0° C., 10 ml of trifluoroacetic acid are added and the mixture is stirred for 2 hours at RT. The reaction mixture is concentrated under vacuum, the residue is taken up in DCM and the solvent is evaporated off under vacuum, this operation being repeated several times. 2 g of the expected product are obtained.

Preparation 2.5

(2S,4S)-4-Hydroxy-N,N-dimethyl-2-pyrrolidine-carboxamide Hydrochloride (V), HCl: $R_5=N(CH_3)_2$; $R_6=H$ A) (2S,4S)-1-(tert-Butoxycarbonyl)-4-hydroxy-2-pyrrolidinecarboxylic Acid 13.2 g of di-tert-butyl dicarbonate are added to a mixture of 4 g of (2S,4S)-4-hydroxypyrrolidine-2-carboxylic acid in 50 ml of a 10% solution of triethylamine in methanol, and the mixture is then refluxed for 45 minutes. The reaction mixture is concentrated under vacuum, the residue is taken up in 40 ml of water and acidified to pH=2 by addition of concentrated HCl solution, the resulting mixture is extracted with EtOAc, the organic phase is dried over $Na_2SO_4$ and the solvent is evaporated off under vacuum. 7.5 g of the expected product are obtained.

B) (2S,4S)-1-(tert-Butoxycarbonyl)-4-hydroxy-N,N-dimethyl-2-pyrrolidinecarboxamide A mixture of 7.5 g of the compound obtained in the preceding step in 100 ml of DCM is cooled to 4° C., 5.7 ml of DIPEA and then 14.4 g of BOP are added and this mixture is stirred for 30 minutes at 4° C. Dimethylamine gas is then added by sparging for 10 minutes and the mixture is stirred for 3 hours at RT. The reaction mixture is concentrated under vacuum, the residue is extracted with EtOAc, the organic phase is washed with 5% $KHSO_4$ solution, with 5% $Na_2CO_3$ solution, with saturated NaCl solution and dried over $Na_2SO_4$, and the solvent is evaporated off under vacuum. The residue is chromatographed on silica gel, eluting with a DCM/MeOH mixture (93/7; v/v). 2.4 g of the expected product are obtained.

C) (2S,4S)-4-Hydroxy-N,N-dimethyl-2-pyrrolidinecarboxamide Hydrochloride

A mixture of 2.4 g of the compound obtained in the preceding step in 15 ml of a 4N solution of HCl in dioxane is stirred for 2 hours at 4° C. The reaction mixture is concentrated under vacuum and without heating, the residue is taken up in ether and the precipitate formed is spin-filtered off. 0.9 g of the expected product is obtained.

Preparation 2.6

Tert-Butyl 2-[[(3R,5S)-5-[(dimethylamino)carbonyl]-3-pyrrolidinyl]oxy]acetate (V): $R_5=N(CH_3)_2$; $R_6=\!\!-\!\!CH_2COO\!\!-\!\!C(CH_3)_3$ A) (2S,4R)-1-(Benzyloxycarbonyl)-4-hydroxy-N,N-dimethyl-2-pyrrolidinecarboxamide A mixture of 15 g of (2S,4R)-1-(benzyloxycarbonyl)-4-hydroxy-2-pyrrolidinecarboxylic acid, 7.64 g of HOBT and 11.65 g of DCC in 250 ml of DCM is stirred for 1 hour at RT. The reaction mixture is cooled on an ice bath, dimethylamine gas is added by sparging for 10 minutes and this mixture is stirred for 3 hours at RT. An insoluble material is filtered off and the filtrate is concentrated under vacuum. The residue is taken up in saturated $Na_2CO_3$ solution and extracted with DCM, the organic phase is dried over $Na_2SO_4$ and the solvent is evaporated off under vacuum. 13 g of the expected product are obtained in the form of an oil.

B) Tert-Butyl 2-[[(3R,5S)-1-[(Benzyloxycarbonyl)-5-[(dimethylamino)carbonyl]-3-pyrrolidinyl]oxy]acetate A mixture of 5 g of the compound obtained in the preceding step and 3 g of tetrabutylammonium hydrogen sulphate in 100 ml of benzene is cooled to 0° C., 50 ml of aqueous 50% NaOH solution are added, followed by dropwise addition of 5 g of tert-butyl bromoacetate, and this mixture is stirred vigorously for 30 minutes. The reaction mixture is diluted with a benzene/DCM mixture, the phases are separated by settling, the organic phase is dried over $Na_2SO_4$ and the solvents are evaporated off under vacuum. The residue is chromatographed on silica gel, eluting with EtOAc. 6.3 g of the expected product are obtained in the form of an oil.

C) tert-Butyl 2-[[(3R,5S)-5-[(dimethylamino)carbonyl]-3-pyrrolidinyl]oxy]acetate A mixture of 6.3 g of the compound obtained in the preceding step and 0.7 g of 10% palladium-on-charcoal in 200 ml of EtOAc is hydrogenated for 3 hours, at RT and under atmospheric pressure. The catalyst is filtered off on Celite and the filtrate is concentrated to half its volume under vacuum. A solution of the expected product is obtained, which is used in Preparations 3.43 and 3.44.

Preparation 2.7

(3R,5S)-5-[(Dimethylamino)carbonyl]-3-pyrrolidine 3-(4-morpholinyl)propionate (V):$R_5$=—N($CH_3$)$_2$;

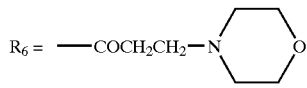

A) Benzyl(2S,4R)-4-(acryloyloxy)-2-[(dimethylamino) carbonyl]-1-pyrrolidinecarboxylate A mixture of 5 g of the compound obtained in step A of Preparation 2.6 and 2.31 g of triethylamine in 100 ml of DCM is cooled to 0° C., 1.6 ml of acryloyl chloride are added dropwise and the mixture is stirred for 2 hours at 0° C. The reaction mixture is washed with water and dried over $Na_2SO_4$, and the solvent is evaporated off under vacuum. 5.5 g of the expected product are obtained in the form of an oil B) Benzyl (2S,4R)-2-[(dimethylamino)carbonyl]-4-[[3-(4-morpholinyl)propanoyl]oxy]-1-pyrrolidinecarboxylate 0.265 g of ferric chloride and then 2.13 g of morpholine are added to a solution of 5.5 g of the compound obtained in the preceding step in 100 ml of DCM, and the mixture is stirred for 18 hours at RT. The reaction mixture is washed with saturated $Na_2SO_4$ solution, the phases are separated by settling, the organic phase is dried over $Na_2SO_4$ and the solvent is evaporated off under vacuum. The residue is chromatographed on silica gel, eluting with DCM and then with a DCM/MeOH mixture (94/6; v/v). 4.5 g of the expected product are obtained in the form of an oil.

C) (3R,5S)-5-[(Dimethylamino)carbonyl]-3-pyrrolidine 3-(4-morpholinyl)propionate A mixture of 4.2 g of the compound obtained in the preceding step and 0.45 g of 10% palladium-on-charcoal in 200 ml of EtOAc is hydrogenated for 3 hours, at RT and at atmospheric pressure. The catalyst is filtered off on Celite and the filtrate is concentrated to half its volume under vacuum. A solution of the expected product is obtained, which is used in this form in Preparation 3.45.

Preparation of the Compounds of Formula (II).

Preparations 3.1 and 3.2

(2S,4R)-1-[5-Chloro-3-(2-methoxyphenyl)-2-oxo-2,3-dihydro-1H-indol-3-yl]-4-hydroxy-N,N-dimethyl-2-pyrrolidinecarboxamide, Isomer A and Isomer B (II): $R_1$=Cl; $R_2$=H; $R_3$=$OCH_3$; $R_4$=H; $R_5$=N($CH_3$)$_2$; $R_6$=H The compound obtained in Preparation 2.1 b) is dissolved in 5 ml of DCM, 1.62 g of triethylamine are added, followed by a suspension of 2.2 g of the compound obtained in Preparation 1.1 in 2 ml of THF, and this mixture is stirred for 6 hours at RT. 3×0.8 g of triethylamine are then added over a period of 24 hours with stirring. At the end of the reaction, the formation of an abundant precipitate is observed. The precipitate formed is spin-filtered off and taken up in a mixture consisting of 5% $K_2CO_3$ solution and 100 ml of EtOAc containing 10 ml of MeOH, the organic phase is washed with 5% $K_2CO_3$ solution, with saturated NaCl solution and dried over $Na_2SO_4$, and the solvents are partially evaporated off under vacuum. The precipitate formed is spin-filtered off to give 0.875 g of isomer A. The spin-filtration mother liquors are combined and chromatographed on alumina, eluting with a gradient of a DCM/MeOH mixture of from (96/4; v/v) to (95/5; v/v). The two isomers are separated:

the less polar, isomer A: compound of Preparation 3.1, giving an additional 0.359 g; m.p.=265–268° C.

$\alpha_D^{25}$=+180° (c=0.16; chloroform);

the more polar, isomer B: compound of Preparation 3.2, which is recrystallized from a DCM/iso-ether mixture to give 0.72 g, containing 0.15 mol of iso-ether.

$\alpha_D^{25}$=−193.7° C. (c=0.16; chloroform).

Preparations 3.3 and 3.4

(2S,4R)-1-[5-Chloro-3-(2-chlorophenyl)-2-oxo-2,3-dihydro-1H-indol-3-yl]-4-hydroxy-N,N-dimethyl-2-pyrrolidinecarboxamide, Isomer A and Isomer B (II): $R_1$=Cl; $R_2$=H; $R_3$=Cl; $R_4$=H; $R_5$=N($CH_3$)$_2$; $R_6$=H 0.8 g of the compound obtained in Preparation 2.1 a) and then 3.5 ml of DIPEA are added, at RT, to a mixture of 3 g of the compound obtained in Preparation 1.2 in 50 ml of DCM, and this mixture is stirred for 12 hours at RT. The reaction mixture is concentrated under vacuum, the residue is extracted with EtOAc, the organic phase is washed with 5% $K_2CO_3$ solution, three times with water, with saturated NaCl solution and dried over $Na_2SO_4$, and the solvent is evaporated off under vacuum. The residue is chromatographed on silica gel, eluting with a DCM/MeOH mixture (95/5; v/v). The two isomers are separated:

the less polar, isomer A: compound of Preparation 3.3, which is re-chromatographed on alumina, eluting with a DCM/MeOH mixture (95/5; v/v) to give 0.182 g.

$\alpha_D^{25}$=+235.30 (c=0.15; chloroform);

the more polar, isomer B: compound of Preparation 3.4, which is re-chromatographed on alumina, eluting with a DCM/MeOH mixture (95/5; v/v). 0.68 g is obtained after crystallization from a DCM/iso-ether mixture; m.p.=266–267° C.

$\alpha_D^{25}$=−225.60 (c=0.117; chloroform).

Preparations 3.5 and 3.6

(2S,4R)-1-[5-Methyl-3-(2-methoxyphenyl)-2-oxo-2,3-dihydro-1H-indol-3-yl]-4-hydroxy-N,N-dimethyl-2-pyrrolidinecarboxamide, Isomer A and Isomer B (II): $R_1$=$CH_3$; $R_2$=H; $R_3$=$OCH_3$; $R_4$=H; $R_5$=N($CH_3$)$_2$; $R_6$=H 3.5 ml of DIPEA and then 1 g of the compound obtained in Preparation 2.1 a) are added to a mixture of 1.5 g of the compound obtained in Preparation 1.3 in 15 ml of DCM and 3 ml of THF, and this mixture is stirred for 5 hours at RT. The reaction mixture is concentrated under vacuum, the residue is extracted with EtOAc, the organic phase is washed with 5% $K_2CO_3$ solution, three times with water, with saturated NaCl solution and dried over $Na_2SO_4$, and the solvent is evaporated off under vacuum. The residue is chromatographed on silica gel, eluting with a DCM/MeOH mixture (96/4; v/v). The two isomers are separated:

the less polar, isomer A: compound of Preparation 3.5, which is crystallized from a DCM/iso-ether mixture. 0.183 g is obtained; m.p.=257–258° C.

$\alpha_D^{25}$=+151.60 (c=0.122; chloroform);

the more polar, isomer B: compound of Preparation 3.6, which is re-chromatographed on alumina, eluting with a DCM/MeOH mixture (97/3; v/v). 0.498 g is obtained, which is used without further purification.

Preparations 3.7 and 3.8
(2S,4R)-1-[5-Chloro-3-(2-methoxyphenyl)-2-oxo-2,3-dihydro-1H-indol-3-yl]-2-(azetidin-1-ylcarbonyl)-4-hydroxypyrrolidine, isomer A and isomer B
(II): $R_1$=Cl; $R_2$=H; $R_3$=OCH$_3$; $R_4$=H;

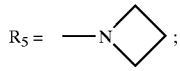

$R_6$=H.

1.82 g of the compound obtained in Preparation 1.1 and then 2 ml of DIPEA are added, at RT, to a solution of 0.9 g of the compound obtained in Preparation 2.2 in 15 ml of DCM, and this mixture is heated at 40° C. for 3 hours. The reaction mixture is concentrated under vacuum, the residue is taken up in 5% K$_2$CO$_3$ solution and extracted three times with EtOAc, the combined organic phases are washed with water, with saturated NaCl solution and dried over Na$_2$SO$_4$, and the solvent is evaporated off under vacuum. The residue is chromatographed on alumina, eluting with a DCM/MeOH mixture (96/4; v/v). The two isomers are separated:
- the less polar, isomer A: compound of Preparation 3.7, which is recrystallized from iso-ether to give 0.243 g; m.p.=270–271° C.

$\alpha_D^{25}$=+169.5° (c=0.115; chloroform);
- the more polar, isomer B: compound of Preparation 3.8, to give 0.716 g which is used without further purification.

Preparations 3.9 and 3.10
(2S,4R)-1-[3-(2-Methoxyphenyl)-5-trifluoromethoxy-2-oxo-2,3-dihydro-1H-indol-3-yl]-4-hydroxy-N,N-dimethyl-2-pyrrolidinecarboxamide, Isomer A and Isomer B
(II): $R_1$=OCF$_3$; $R_2$=H; $R_3$=OCH$_3$; $R_4$=H; $R_5$=N(CH$_3$)$_2$; $R_6$=H 4 ml of DIPEA and then 1.26 g of the compound obtained in Preparation 2.1 a) are added to the solution of the compound obtained in Preparation 1.4 in DCM, and this mixture is stirred for 4 hours at RT. The reaction mixture is concentrated under vacuum, the residue is extracted with EtOAc, the organic phase is washed with 5% K$_2$CO$_3$ solution, twice with water, with saturated NaCl solution and dried over Na$_2$SO$_4$, and the solvent is evaporated off under vacuum. The residue is chromatographed on alumina, eluting with DCM and then with a gradient of a DCM/MeOH mixture up to (95.5/4.5; v/v). The two isomers are separated:
- the less polar, isomer A: compound of Preparation 3.9, which is crystallized from iso-ether to give 0.09 g; m.p.=231–233° C.

$\alpha_D^{25}$=+152° (c=0.123; chloroform);
- the more polar, isomer B: compound of Preparation 3.10, to give 0.323 g; m.p.=219–220° C.

$\alpha_D^{25}$=−220° (c=0.11; chloroform).

Preparations 3.11 and 3.12
(2S,4R)-1-[5-Chloro-3-(2-methoxyphenyl)-6-methyl-2-oxo-2,3-dihydro-1H-indol-3-yl]-4-hydroxy-N,N-dimethyl-2-pyrrolidinecarboxamide, Isomer A and Isomer B
(II): $R_1$=Cl; $R_2$=6-CH$_3$; $R_3$=OCH$_3$; $R_4$=H; $R_5$=N(CH$_3$)$_2$; $R_6$=H The solution of the compound obtained in Preparation 1.5 in DCM is cooled to 0° C., 2.25 ml of DIPEA are added, followed by 0.83 g of the compound obtained in Preparation 2.1 a), and this mixture is stirred for 12 hours while allowing the temperature to return to RT. The reaction mixture is concentrated under vacuum, the residue is extracted with EtOAc, the organic phase is washed with 5% K$_2$CO$_3$ solution, with water, with saturated NaCl solution and dried over Na$_2$SO$_4$, and the solvent is evaporated off under vacuum. The residue is chromatographed on silica gel, eluting with a DCM/MeOH mixture (95/5; v/v). The two isomers are separated:
- the less polar, isomer A: compound of Preparation 3.11, which is crystallized from iso-ether to give 0.139 g, m.p.=260–261° C.

$\alpha_D^{25}$=+162.50 (c=0.144; chloroform);
- the more polar, isomer B: compound of Preparation 3.12, to give 0.606 g which is used without further purification.

Preparations 3.13 and 3.14
(2S,4R)-1-[3-(2-Chlorophenyl)-5,6-dimethyl-2-oxo-2,3-dihydro-1H-indol-3-yl]-4-hydroxy-N,N-dimethyl-2-pyrrolidinecarboxamide, Isomer A and Isomer B
(II): $R_1$=CH$_3$; $R_2$=6-CH$_3$; $R_3$=Cl; $R_4$=H; $R_5$=N(CH$_3$)$_2$; $R_6$=H The solution of the compound obtained in Preparation 1.6 in DCM is cooled to 0° C., 0.6 ml of DIPEA is added, followed by 0.7 g of the compound obtained in Preparation 2.1 a) and this mixture is stirred overnight while allowing the temperature to rise to RT. The reaction mixture is concentrated under vacuum, the residue is taken up in 5% K$_2$CO$_3$ solution and extracted with EtOAc, the organic phase is dried over Na$_2$SO$_4$ and the solvent is evaporated off under vacuum. The residue is chromatographed on silica gel, eluting with a DCM/MeOH mixture (95/5; v/v). The two isomers are separated:
- the less polar, isomer A: compound of Preparation 3.13.
- the more polar, isomer B: compound of Preparation 3.14, to give 0.363 g in the form of an oil which is used without further purification.

Preparations 3.15 and 3.16
(2S,4R)-1-[5-Chloro-3-(2,3-dimethoxyphenyl)-2-oxo-2,3-dihydro-1H-indol-3-yl]-4-methoxy-N,N-dimethyl-2-pyrrolidinecarboxamide, Isomer A and Isomer B
(II): $R_1$=Cl; $R_2$=H; $R_3$=OCH$_3$; $R_4$=3-OCH$_3$; $R_5$=N(CH$_3$)$_2$; $R_6$=CH$_3$ 1.71 ml of DIPEA and then 0.75 g of the compound obtained in Preparation 2.3 are added, at RT, to a solution of 1.1 g of the compound obtained in Preparation 1.7 in 20 ml of DCM, and this mixture is stirred for 3 hours at RT. The reaction mixture is concentrated under vacuum, the residue is extracted with EtOAc, the organic phase is washed with 5% K$_2$CO$_3$ solution, twice with water, with saturated NaCl solution and dried over Na$_2$SO$_4$, and the solvent is evaporated off under vacuum. The residue is chromatographed on alumina, eluting with a gradient of a DCM/MeOH mixture of from (98.5/1.5; v/v) to (98/2; v/v). The two isomers are separated:
- the less polar, isomer A: compound of Preparation 3.15, to give 0.32 g
- the more polar, isomer B: compound of Preparation 3.16, which is recrystallized from iso-ether to give 0.49 g; m.p.=235–237° C.

$\alpha_D^{25}$=−160.7° (c=0.102; chloroform).

Preparations 3.17 and 3.18
(2S,4R)-1-[5-Chloro-3-(2-methoxyphenyl)-6-trifluoromethyl-2-oxo-2,3-dihydro-1H-indol-3-yl]-4-methoxy-N,N-dimethyl-2-pyrrolidinecarboxamide, Isomer A and Isomer B
(II) $R_1$=Cl; $R_2$=6-CF$_3$; $R_3$=OCH$_3$; $R_4$=H; $R_5$=N(CH$_3$)$_2$; $R_6$=CH$_3$ 2.5 ml of DIPEA and 0.870 g of the compound obtained in Preparation 2.3 are added to the solution of the compound obtained in Preparation 1.8 in 10 ml of DCM, and the mixture is stirred for 10 hours at RT. The reaction mixture is concentrated under vacuum, the residue is extracted with EtOAc, the organic phase is washed with 5% $K_2CO_3$ solution, twice with water, with saturated NaCl solution and dried over $Na_2SO_4$, and the solvent is evaporated off under vacuum. The residue is chromatographed on alumina, eluting with a gradient of a DCM/MeOH mixture (98.5/1.5; v/v). The two isomers are separated:

the less polar, isomer A: compound of Preparation 3.17, which is crystallized from DCM to give 0.23 g; m.p.= 291–293° C.

$\alpha_D^{25}=+131.6°$ (c=0.12; chloroform);

the more polar, isomer B: compound of Preparation 3.18, which is precipitated from hexane to give 0.44 g; m.p.=138–140° C.

$\alpha_D^{25}25=157.1°$ (c=0.098; chloroform).

Preparations 3.19 and 3.20

(2S,4R)-1-[5-Chloro-3-(2-chlorophenyl)-6-methoxy-2-oxo-2,3-dihydro-1H-indol-3-yl]-4-methoxy-N,N-dimethyl-2-pyrrolidinecarboxamide, Isomer A and Isomer B (II) $R_1$=Cl; $R_2$=6-$OCH_3$; $R_3$=Cl; $R_4$=H; $R_5$=N($CH_3$)$_2$; $R_6$=$CH_3$ 1.5 g of the compound obtained in Preparation 2.3 are added, under an argon atmosphere, to the suspension of the compound obtained in Preparation 1.9 in DCM, followed by dropwise addition of a solution of 1.8 g of DIPEA in 2 ml of DCM, and the mixture is stirred for 2 hours at RT. The reaction mixture is concentrated under vacuum, the residue is taken up in 5% $K_2CO_3$ solution and extracted with EtOAc, the organic phase is washed with water, with saturated NaCl solution and dried over $Na_2SO_4$, the EtOAc is partially concentrated and the precipitate formed is left to crystallize and is spin-filtered off. An isomer is separated out:

isomer A: compound of Preparation 3.19, to give 0.581 g; m.p.=249–250° C.

$\alpha_D^{25}=+202.5°$ (c=0.12; chloroform).

The spin-filtration liquors are chromatographed on alumina, eluting with a DCM/MeOH mixture (98/2; v/v). The other isomer is separated out:

the more polar, isomer B: compound of Preparation 3.20, to give 0.519 g after crystallization from a DCM/EtOAc mixture; m.p.=243–244° C.

$\alpha_D^{25}=-221.8°$ (c=0.13; chloroform).

Preparations 3.21 and 3.22

(2S,4R)-1-[6-Chloro-3-(2-methoxyphenyl)-5-methyl-2-oxo-2,3-dihydro-1H-indol-3-yl]-4-methoxy-N,N-dimethyl-2-pyrrolidinecarboxamide, Isomer A and Isomer B (II): $R_1$=$CH_3$; $R_2$=6-Cl; $R_3$=$OCH_3$; $R_4$=H; $R_5$=N($CH_3$)$_2$; $R_6$=$CH_3$ 5.5 ml of DIPEA and then 1.85 g of the compound obtained in Preparation 2.3 are added to the solution of the compound obtained in Preparation 1.10 in DCM, and the mixture is stirred for 12 hours at RT. The reaction mixture is concentrated under vacuum, the residue is extracted with EtOAc, the organic phase is washed with 5% $K_2CO_3$ solution, twice with water, with saturated NaCl solution and dried over $Na_2SO_4$, and the solvent is evaporated off under vacuum. The residue is chromatographed on alumina, eluting with a DCM/MeOH mixture of from (99/1; v/v) to (98/2; v/v). The two isomers are separated:

the less polar, isomer A: compound of Preparation 3.21, to give 0.7 g after crystallization from iso-ether; m.p.= 264° C.

$\alpha_D^{25}=+183°$ (c=0.1; chloroform);

the more polar, isomer B: compound of Preparation 3.22, to give 1.275 g after crystallization from iso-ether; m.p.=245° C.

$\alpha_D^{25}=-195.1°$ (c=0.12; chloroform).

Preparations 3.23 and 3.24

(2S,4R)-1-[5-Chloro-3-(2-methoxyphenyl)-2-oxo-2,3-dihydro-1H-indol-3-yl]-4-ethoxy-N,N-dimethyl-2-pyrrolidinecarboxamide, Isomer A and Isomer B (II): $R_1$=Cl; $R_2$=H; $R_3$=$OCH_3$; $R_4$=H; $R_5$=N($CH_3$)$_2$; $R_6$=—$CH_2CH_3$ A mixture of 2.15 g of the compound obtained in Preparation 1.1, 2 g of the compound obtained in Preparation 2.4 and 1.4 g of triethylamine in 50 ml of THF is stirred for 48 hours at RT. The reaction mixture is concentrated under vacuum, the residue is taken up in water and extracted with DCM, the organic phase is dried over $Na_2SO_4$ and the solvent is evaporated off under vacuum. The residue is taken up in a DCM/EtOAc mixture (50/50; v/v), heated to reflux and left to stand. The precipitate formed is spin-filtered off and isolated:

isomer A: compound of Preparation 3.23, to give 1.1 g; m.p.=236° C.

$\alpha_D^{25}=+109°$ (c=0.22; chloroform).

The spin-filtration liquors are chromatographed on silica gel, eluting with an EtOAc/MeOH mixture (97/3; v/v) and the other isomer is separated out:

the more polar, isomer B: compound of Preparation 3.24, to give 1 g $\alpha_D^{25}=-164°$ (c=0.25; chloroform).

Preparations 3.25 and 3.26

(2S,4R)-1-[5-Chloro-3-(2,3-dimethoxyphenyl)-2-oxo-2,3-dihydro-1H-indol-3-yl]-4-hydroxy-N,N-dimethyl-2-pyrrolidinecarboxamide, Isomer A and Isomer B (II) $R_1$=Cl; $R_2$=H; $R_3$=$OCH_3$; $R_4$=3-$OCH_3$; $R_5$=N($CH_3$)$_2$; $R_6$=H 2.5 ml of DIPEA and then 1 g of the compound obtained in Preparation 2.1 a) are added, at RT, to a solution of 1.6 g of the compound obtained in Preparation 1.7 in 10 ml of DCM and the mixture is stirred for 48 hours at RT. The precipitate formed, corresponding to isomer A below, is spin-filtered off. The filtrate is concentrated under vacuum, the residue is extracted with EtOAc, the organic phase is washed with 5% $K_2CO_3$ solution, with water, with saturated NaCl solution and dried over $Na_2SO_4$, and the solvent is evaporated off under vacuum. The residue is chromatographed on silica gel, eluting with a gradient of a DCM/MeOH mixture of from (99/1; v/v) to (93/7; v/v). The two isomers are separated:

the less polar, isomer A: compound of Preparation 3.25, which is recrystallized with the first crop above from a DCM/iso-ether mixture; m.p.=261–263° C.

$\alpha_D^{25}=+119.3°$ (c=0.135; chloroform)

the more polar, isomer B: compound of Preparation 3.26, which is recrystallized in a DCM/iso-ether mixture to give 0.94 g; m.p.=167–169° C.

$\alpha_D^{25}=-168.6°$ (c=0.172; chloroform).

Preparations 3.27 and 3.28

(2S,4R)-1-[5,6-Dichloro-3-(2-chlorophenyl)-2-oxo-2,3-dihydro-1H-indol-3-yl]-4-hydroxy-N,N-dimethyl-2-pyrrolidinecarboxamide, Isomer A and Isomer B (II): $R_1$=Cl; $R_2$=6-Cl; $R_3$=Cl; $R_4$=H; $R_5$=N($CH_3$)$_2$; $R_6$=H 1.6 g of the compound obtained in Preparation 1.11 and then 2.13 ml of DIPEA are added, at RT, to a mixture of 0.8 g of the compound obtained in Preparation 2.1 a) in 15 ml of DCM, and the mixture is stirred for 15 minutes at RT. The reaction mixture is concentrated under vacuum, the residue is extracted with EtOAc, the organic phase is washed with 5% $K_2CO_3$ solution, with water, with saturated NaCl solution and dried over $Na_2SO_4$, and the solvent is evaporated off under vacuum. The residue is chromatographed on silica gel, eluting with a DCM/MeOH mixture (95/5; v/v). The two isomers are separated:

the less polar, isomer A: compound of Preparation 3.27, which is crystallized from iso-ether to give 0.08 g; m.p. >260° C.

$\alpha_D^{25}$=+219.4° (c=0.103; chloroform)

the more polar, isomer B: compound of Preparation 3.28, to give 0.661 g which is used without further purification.

Preparations 3.29 and 3.30

Methyl (2S,4R)-1-[5-chloro-3-(2-methoxyphenyl)-2-oxo-2,3-dihydro-1H-indol-3-yl]-4-hydroxy-2-pyrrolidinecarboxylate, Isomer A and Isomer B (II): $R_1$=Cl; $R_2$=H; $R_3$=OCH$_3$; $R_4$=H; $R_5$=OCH$_3$; $R_6$=H 4 ml of DIPEA and then 1.64 g of methyl (2S,4R)-4-hydroxy-2-pyrrolidinecarboxylate hydrochloride are added, at RT, to a mixture of 1.4 g of the compound obtained in Preparation 1.1 in 20 ml of DCM, and the mixture is stirred for 12 hours at RT. The reaction mixture is concentrated under vacuum, the residue is extracted with EtOAc, the organic phase is washed with 5% $K_2CO_3$ solution, with water, with saturated NaCl solution and dried over sodium sulphate, and the solvent is evaporated off under vacuum. The residue is chromatographed on silica gel, eluting with a DCM/MeOH mixture (97/3; v/v). The two isomers are separated:

the less polar isomer, isomer A: compound of Preparation 3.29, to give 0.3 g; m.p.=234–235° C.

$\alpha_D^{25}$=+143.3° (c=0.136; chloroform);

the more polar isomer, isomer B: compound of Preparation 3.30, which is recrystallized from a DCM/iso-ether/hexane mixture to give 1.1 g $\alpha_D^{25}$=199.1° (c=0.112; chloroform).

Preparation 3.31

Methyl (2S,4R)-1-[5-chloro-3-(2-methoxyphenyl)-6-methyl-2-oxo-2,3-dihydro-1H-indol-3-yl]-4-hydroxy-2-pyrrolidinecarboxylate, mixture of the two diastereoisomers (II): $R_1$=Cl; $R_2$=6-CH$_3$; $R_3$=OCH$_3$; $R_4$=H; $R_5$=OCH$_3$; $R_6$=H The solution of the compound obtained in Preparation 1.5 in DCM is concentrated under vacuum, the residue is taken up in a mixture of 20 ml of THF and 10 ml of DCM, 0.715 g of methyl (2S,4R)-4-hydroxy-2-pyrrolidinecarboxylate hydrochloride is added, at RT, followed by 0.8 g of triethylamine, and the mixture is stirred for 48 hours at RT. The reaction mixture is concentrated under vacuum, the residue is extracted with DCM, the organic phase is washed with water and dried over $Na_2SO_4$, and the solvent is evaporated off under vacuum. The residue is chromatographed on silica gel, eluting with a DCM/EtOAc mixture (50/50; v/v). 1.8 g of a mixture of the two diastereoisomers are obtained.

Preparation 3.32

(2S,4S)-1-[5-Chloro-3-(2-methoxyphenyl)-2-oxo-2,3-dihydro-1H-indol-3-yl]-4-hydroxy-N,N-dimethyl-2-pyrrolidinecarboxamide, mixture of the two diastereoisomers (II): $R_1$ Cl; $R_2$=H; $R_3$=OCH$_3$; $R_4$=H; $R_5$=N(CH$_3$)$_2$; $R_6$=H A mixture of 4.6 g of the compound obtained in Preparation 2.5 in 50 ml of DCM is cooled to 4° C., 2.7 g of the compound obtained in Preparation 1.1 and then 5 ml of triethylamine are added and the mixture is stirred for 48 hours at RT. The reaction mixture is concentrated under vacuum, the residue is extracted with EtOAc, the organic phase is washed with 5% $Na_2CO_3$ solution, with saturated NaCl solution and dried over $Na_2SO_4$, and the solvent is evaporated off under vacuum. The residue is chromatographed on alumina, eluting with a DCM/MeOH mixture (98/2; v/v). 1.6 g of a mixture of the two diastereoisomers are obtained.

Preparation 3.33

(2S,4R)-1-[5-Chloro-3-(2-ethoxyphenyl)-2-oxo-2,3-dihydro-1H-indol-3-yl]-4-hydroxy-N,N-dimethyl-2-pyrrolidinecarboxamide, laevorotatory isomer (II): $R_1$=Cl; $R_2$=H; $R_3$=OCH$_2$CH$_3$; $R_4$=H; $R_5$=N(CH$_3$)$_2$; $R_6$=H 1.38 g of the compound obtained in Preparation 2.1 a) and then 1.46 g of DIPEA are added to a solution of 2 g of the compound obtained in Preparation 1.12 in 20 ml of DCM, and the mixture is stirred for 12 hours at RT. The reaction mixture is concentrated under vacuum, the residue is extracted with EtOAc, the organic phase is washed with 5% $K_2CO_3$ solution and dried over $Na_2SO_4$, and the solvent is evaporated off under vacuum. The residue is chromatographed on alumina, eluting with a DCM/MeOH mixture (95/5; v/v). The two diastereoisomers are separated and the more polar compound is collected and re-chromatographed on silica gel, eluting with a DCM/EtOAc mixture (60/40; v/v) and then with DCM/MeOH (94/6; v/v). 0.726 g of the expected product is obtained.

Preparations 3.34 and 3.35

(2S,4R)-1-[5-Chloro-3-(2-trifluoromethoxyphenyl)-2-oxo-2,3-dihydro-1H-indol-3-yl]-4-hydroxy-N,N-dimethyl-2-pyrrolidinecarboxamide, Isomer A and Isomer B (II): $R_1$=Cl; $R_2$=H; $R_3$=OCF$_3$; $R_4$=H; $R_5$=N(CH$_3$)$_2$; $R_6$=H A mixture of 1.6 g of the compound obtained in Preparation 1.13, 0.8 g of the compound obtained in Preparation 2.1 a) and 1 ml of DIPEA in 20 ml of DCM is stirred for 24 hours at RT. The precipitate formed, corresponding to isomer A, which is the less polar compound on silica gel, DCM/MeOH (98/2; v/v) (compound of Preparation 3.34), is spin-filtered off. The spin-filtration liquors are placed at 0° C. for 48 hours and the precipitate formed, again corresponding to isomer A, is spin-filtered off. The spin-filtration liquors are washed with water, the organic phase is dried over $Na_2SO_4$ and the solvent is evaporated off under vacuum. The residue is chromatographed on silica gel, eluting with a DCM/MeOH mixture (98/2; v/v). The other isomer is separated out:

the more polar, isomer B: compound of Preparation 3.35, to give 0.2 g.

Preparations 3.36 and 3.37

(2S,4R)-1-[5-Chloro-3-(2,3-difluorophenyl)-2-oxo-2,3-dihydro-1H-indol-3-yl]-4-hydroxy-N,N-dimethyl-2-pyrrolidinecarboxamide, Isomer A and Isomer B (II): $R_1$=Cl; $R_2$=H; $R_3$=F; $R_4$=3-F; $R_5$=N(CH$_3$)$_2$; $R_6$=H A mixture of 0.4 g of the compound obtained in Preparation 1.14, 0.3 g of the compound obtained in Preparation 2.1 a) and 0.45 g of DIPEA in 20 ml of DCM is stirred for 2 hours at RT. The precipitate formed, corresponding to isomer A, which is the less polar compound on alumina, DCM/MeOH (98/2; v/v) (compound of Preparation 3.36), is spin-filtered off. The spin-filtration liquors are concentrated under vacuum, the residue is taken up in an EtOAc/acetone mixture, the resulting mixture is left for 12 hours under cold conditions, and the precipitate, again corresponding to isomer A, is spin-filtered off. The spin-filtration liquors are washed with water, the organic phase is dried over $Na_2SO_4$ and the solvent is evaporated off under vacuum. The residue is chromatographed on alumina, eluting with a DCM/MeOH mixture (98/2; v/v). The other isomer is separated out:
the more polar, isomer B: compound of Preparation 3.37, to give 0.1 g.
$\alpha_D^{25} = -231°$ (c=0.16; chloroform).

Preparations 3.38 and 3.39
(2S,4R)-1-[5-Chloro-3-(2,4-dimethoxyphenyl)-2-oxo-2,3-dihydro-1H-indol-3-yl]-4-hydroxy-N,N-dimethyl-2-pyrrolidinecarboxamide, Isomer A and Isomer B
(II): $R_1$=Cl; $R_2$=H; $R_3$=OCH$_3$; $R_4$=4-OCH$_3$; $R_5$=N(CH$_3$)$_2$; $R_6$=H 1.5 g of the compound obtained in Preparation 2.1 a) are added to a solution of the compound obtained in Preparation 1.15 and 1 ml of triethylamine in 20 ml of DCM, and this mixture is stirred for 1 hour at RT. The reaction mixture is washed twice with water, the organic phase is dried over Na$_2$SO$_4$ and the solvent is evaporated off under vacuum. The residue is chromatographed on alumina, eluting with DCM and then with a DCM/MeOH mixture (98.2; v/v). The two isomers are separated:
the less polar, isomer A: compound of Preparation 3.38
the more polar, isomer B: compound of Preparation 3.39, to give 0.26 g
$\alpha_D^{25} = -157°$ (c=0.15; chloroform).

Preparation 3.40
(2S,4R)-1-[5-Chloro-3-(1,3-benzodioxol-4-yl)-2-oxo-2,3-dihydro-1H-indol-3-yl]-4-hydroxy-N,N-dimethyl-2-pyrrolidinecarboxamide, Laevorotatory Isomer
(II): $R_1$=Cl; $R_2$=H; $R_3$+$R_4$=2,3-O—CH$_2$—O—; $R_5$=N(CH$_3$)$_2$; $R_6$=H A mixture of 1.7 g of the compound obtained in Preparation 1.16, 0.9 g of the compound obtained in Preparation 2.1 a) and 1 ml of DIPEA in 20 ml of DCM is stirred for 2 hours at RT. The reaction mixture is washed with water, the organic phase is dried over Na$_2$SO$_4$ and the solvent is evaporated off under vacuum. The residue is chromatographed on alumina, eluting with a DCM/MeOH mixture (97/3; v/v). The two diastereoisomers are separated out and the more polar compound is collected. 0.42 g of the expected product is obtained.
$\alpha_D^{25} = -108°$ (c=0.12; chloroform).

Preparations 3.41 and 3.42
(2S,4R)-1-[5,6-Dichloro-3-(2-methoxyphenyl)-2-oxo-2,3-dihydro-1H-indol-3-yl]-4-hydroxy-N,N-dimethyl-2-pyrrolidinecarboxamide, Isomer A and Isomer B
(II): $R_1$=Cl; $R_2$=6-Cl; $R_3$=OCH$_3$; $R_4$=H; $R_5$=N(CH$_3$)$_2$; $R_6$=H A mixture of 1.57 g of the compound obtained in Preparation 1.17, 1.45 g of the compound obtained in Preparation 2.1 a) and 0.8 ml of DIPEA in 15 ml of DCM is stirred for 1 hour 30 minutes at RT. The precipitate formed, corresponding to isomer A, which is the less polar compound on silica gel, DCM/MeOH (94/6; v/v), is spin-filtered off. The spin-filtration liquors are concentrated under vacuum, the residue is extracted with EtOAc, the organic phase is washed with 5% K$_2$CO$_3$ solution, with water, with saturated NaCl solution and dried over Na$_2$SO$_4$, and the solvent is evaporated off under vacuum. The residue is chromatographed on silica gel, eluting with the DCM/MeOH mixture (94/6; v/v). The two isomers are separated:
the less polar, isomer A: compound of Preparation 3.41, which is crystallized from an iso-ether/MeOH mixture to give 0.295 g; m.p.=261–262° C.
$\alpha_D^{25} = +113.8°$ (c=0.12; chloroform)
the more polar, isomer B: compound of Preparation 3.42, to give 0.74 g.

Preparations 3.43 and 3.44
Tert-Butyl 2-[[(3R,5S)-1-[5-chloro-3-(2-methoxyphenyl)-2-oxo-2,3-dihydro-1H-indol-3-yl]-5-[(dimethylamino)carbonyl]-3-pyrrolidinyl]oxy]acetate, Isomer A and Isomer B
(II): $R_1$=Cl; $R_2$=H; $R_3$=OCH$_3$; $R_4$=H; $R_5$=N(CH$_3$)$_2$; $R_6$=—CH$_2$COOC(CH$_3$)$_3$ 200 ml of THF, 1.87 g of triethylamine and then 4.5 g of the compound obtained in Preparation 1.1 are added to the solution of the compound obtained in Preparation 2.6 and the mixture is refluxed for 48 hours. The product is concentrated under vacuum and the residue is chromatographed on silica gel, eluting with a DCM/MeOH mixture (96/4; v/v). The isomers are separated:
the less polar, isomer A: compound of Preparation 3.43, to give 1 g
the more polar, isomer B: compound of Preparation 3.44, to give 3 g in the form of an oil.
$\alpha_D^{25} = -154°$ (c=0.37; chloroform).

Preparation 3.45
(3R,5S)-1-[5-Chloro-3-(2-methoxyphenyl)-2-oxo-2,3-dihydro-1H-indol-3-yl]-5-[(dimethylamino)-carbonyl]-3-pyrrolidinyl 3-(4-morpholinyl)propanoate, mixture of the two diastereoisomers
(II): $R_1$=Cl; $R_2$=H; $R_3$=OCH$_3$; $R_4$=H; $R_5$=—N(CH$_3$)$_2$;

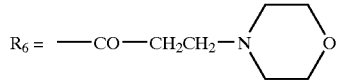

A solution of 3 g of the compound obtained in Preparation 1.1 in 100 ml of THF is added to the solution of the compound obtained in Preparation 2.7 in EtOAc, and the mixture is stirred for 4 days at RT. The reaction mixture is concentrated under vacuum, the residue is extracted with EtOAc, the organic phase is washed with water and dried over Na$_2$SO$_4$, and the solvent is evaporated off under vacuum. The residue is chromatographed on silica gel, eluting with a DCM/MeOH mixture (92/8; v/v). 4.2 g of the expected product are obtained in the form of a foam.

EXAMPLE 1

(2S,4R)-1-[5-Chloro-1-[(2,4-dimethoxyphenyl)-sulphonyl]-3-(2-methoxyphenyl)-2-oxo-2,3-dihydro-1H-indol-3-yl]-4-hydroxy-N,N-dimethyl-2-pyrrolidine-carboxamide, laevorotatory isomer, 0.25 iso-ether
(I): $R_1$=Cl; $R_2$=H; $R_3$=OCH$_3$; $R_4$=H; $R_5$=N(CH$_3$)$_2$; $R_6$=H; $R_7$=2-OCH$_3$; $R_8$=OCH$_3$ A mixture of 0.67 g of the compound obtained in Preparation 3.2 (isomer B) in 10 ml of DMF is cooled to 0° C., under an argon atmosphere, 0.069 g of 60% sodium hydride in oil is added and the mixture is stirred until the evolution of gas has ceased. 0.404 g of 2,4-dimethoxybenzenesulphonyl chloride is then added and the mixture is stirred for 3 hours at RT. The reaction mixture is poured into 5% K$_2$CO$_3$ solution and extracted with EtOAc, the organic phase is washed with water, with saturated NaCl solution and dried over Na$_2$SO$_4$, and the solvent is evaporated off under vacuum. The residue is chromatographed on alumina, eluting with a DCM/MeOH mixture (99/1; v/v). 0.565 g of the expected product is obtained after crystallization from a DCM/iso-ether mixture.
$\alpha_D^{25} = -200°$ C. (c=0.26; chloroform).
$^1$H NMR: DMSO-d$_6$+TFA, 360 K: δ (ppm): 1.6: mt: 2H; 2.1 to 3.1: m: 8H; 3.35: s: 3H; 3.7: s: 3H; 3.9: s: 3H; 4.4: mt: 1H; 4.6: mt: 1H; 6.6 to 8.1: m: 10H.

EXAMPLE 2

(2S,4R)-1-[5-Chloro-1-[(2,4-dimethoxyphenyl)sulphonyl]-3-(2-methoxyphenyl)-2-oxo-2,3-dihydro-1H-indol-3-yl]-4-methoxy-N,N-dimethyl-2-pyrrolidine-carboxamide, Laevorotatory Isomer (I): $R_1$=Cl; $R_2$=H; $R_3$=OCH$_3$; $R_4$=H; $R_5$=N(CH$_3$)$_2$; $R_6$=H; $R_7$=2-OCH$_3$; $R_8$=OCH$_3$ 0.04 g of 60% sodium hydride in oil is added, at RT and under an argon atmosphere, to a solution of 0.559 g of the compound obtained in Example 1 in 6 ml of DMF, and stirring is continued until the evolution of gas has ceased. 0.11 ml of methyl iodide is then added and the mixture is stirred for 24 hours at RT. A further 0.04 g of 60% sodium hydride in oil is added, followed by 0.33 ml of methyl iodide, with stirring for 3 days at RT. The reaction mixture is poured into water and extracted with EtOAc, the organic phase is washed with water, with saturated NaCl solution and dried over Na$_2$SO$_4$, and the solvent is evaporated off under vacuum. The residue is chromatographed on silica gel, eluting with a DCM/MeOH mixture (98/2; v/v). 0.082 g of the expected product is obtained after crystallization from a DCM/iso-ether mixture; m.p.=189–191° C.

EXAMPLE 3

(2S,4R)-1-[5-Chloro-3-(2-chlorophenyl)-1-[(2,4-dimethoxyphenyl)sulphonyl]-2-oxo-2,3-dihydro-1H-indol-3-yl]-4-hydroxy-N,N-dimethyl-2-pyrrolidinecarboxamide, Laevorotatory Isomer (I): $R_1$=Cl; $R_2$=H; $R_3$=Cl; $R_4$=H; $R_5$=N(CH$_3$)$_2$; $R_6$=H; $R_7$=2-OCH$_3$; $R_8$=OCH$_3$ A mixture of 0.567 g of the compound obtained in Preparation 3.4 (isomer B) in 5.5 ml of DMF is cooled to 0° C., under an argon atmosphere, 0.062 g of 60% sodium hydride in oil is added and the mixture is stirred for 10 minutes. 0.338 g of 2,4-dimethoxybenzenesulphonyl chloride is then added and the mixture is stirred for 3 hours at RT. Water is added to the reaction mixture, the resulting mixture is extracted three times with EtOAc, the combined organic phases are washed with saturated NaCl solution and dried over Na$_2$SO$_4$, and the solvent is evaporated off under vacuum. The residue is chromatographed on silica gel, eluting with a DCM/MeOH mixture (98/2; v/v). 0.647 g of the expected product is obtained after crystallization from iso-ether; m.p.=254–256° C.

$\alpha_D^{25}$=−250° (c=0.142; chloroform).

EXAMPLE 4

(2S,4R)-1-[5-Chloro-3-(2-chlorophenyl)-1-[(2,4-dimethoxyphenyl)sulphonyl]-6-methoxy-2-oxo-2,3-dihydro-1H-indol-3-yl]-4-methoxy-N,N-dimethyl-2-pyrrolidinecarboxamide, laevorotatory isomer (I): $R_1$=Cl; $R_2$=6-OCH$_3$; $R_3$=Cl; $R_4$=H; $R_5$=N(CH$_3$)$_2$; $R_6$=H; $R_7$=2-OCH$_3$; $R_8$=OCH$_3$ 0.072 g of 60% sodium hydride in oil is added at RT, under an argon atmosphere, to a suspension of 0.719 g of the compound obtained in Preparation 3.20 (isomer B) in 7 ml of DMF, and the mixture is stirred until the evolution of gas has ceased. 0.390 g of 2,4-dimethoxybenzenesulphonyl chloride is then added and the mixture is stirred for 3 hours at RT. The reaction mixture is poured into 5% K$_2$CO$_3$ solution and extracted with EtOAc and then with DCM, the organic phases are washed separately with water, dried over Na$_2$SO$_4$ and combined, and the solvents are partially concentrated under vacuum to the point of crystallization. The precipitate formed is spin-filtered off to give 0.735 g of the expected product; m.p.=283–288° C.

$\alpha_D^{25}$=266.3° (c=0.11; chloroform).

EXAMPLE 5

(2S,4R)-1-[5-Chloro-1-[(3,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidine-carboxamide, Laevorotatory Isomer (I): $R_1$=Cl; $R_2$=H; $R_3$=OCH$_3$; $R_4$=H; $R_5$=N(CH$_3$)$_2$; $R_6$=H; $R_7$=2-OCH$_3$; $R_8$=OCH$_3$ A solution of 0.043 g of the compound obtained in Preparation 3.2 (isomer B) in 1 ml of THF is cooled to −30° C., under a nitrogen atmosphere, a solution of 0.22 g of potassium tert-butoxide in 1 ml of THF is added and the mixture is stirred for 15 minutes while allowing the temperature to rise to 0° C. A solution of 0.035 g of 3,4-dimethoxybenzene-sulphonyl chloride in 1 ml of THF is then added with stirring, while allowing the temperature to return to RT, and the mixture is then heated at 30° C. for 2 hours 15 minutes. 0.1 g of PS-Trisamine is added and the mixture is stirred for 1 hour 15 minutes at RT. 1 ml of DCM and 1 ml of water are added with stirring, the aqueous phase is then removed by filtration through a Whatman FT 5.0µ PTFE filter and the organic phase is concentrated under vacuum. The residue is chromatographed on silica gel, eluting with DCM and then with a DCM/EtOAc mixture of from (90/10; v/v) to (70/30; v/v) and finally with a DCM/MeOH mixture of from (99/1; v/v) to (96/4; v/v). 0.026 g of the expected product is obtained.

MH$^+$=629.

EXAMPLE 6

Methyl (2S,4R)-1-[5-chloro-3-(2-methoxyphenyl)-1-[(3,4-dimethoxyphenyl)sulphonyl]-2-oxo-2,3-dihydro-1H-indol-3-yl]-4-hydroxy-2-pyrrolidinecarboxylate, laevorotatory isomer (I): $R_1$=Cl; $R_2$=H; $R_3$=OCH$_3$; $R_4$=H; $R_5$=OCH$_3$; $R_6$=H; $R_7$=3-OCH$_3$; $R_8$=OCH$_3$ A mixture of 0.477 g of the compound obtained in Preparation 3.30 (isomer B) in 4.7 ml of DMF is cooled to 0° C. under an argon atmosphere, 0.055 g of 60% sodium hydride in oil is added and the mixture is stirred for 10 minutes. 0.297 g of 3,4-dimethoxy-benzenesulphonyl chloride is then added, and the mixture is stirred for 3 hours 30 minutes at RT. Water is added to the reaction mixture, the resulting mixture is extracted three times with EtOAc, the combined organic phases are washed with water, with saturated NaCl solution and dried over Na$_2$SO$_4$, and the solvent is evaporated off under vacuum. The residue is chromatographed on silica gel, eluting with a DCM/MeOH mixture (97/3; v/v). 0.3 g of the expected product is obtained after crystallization from a DCM/iso-ether mixture.

$\alpha_D^{25}$=−139.1° (c=0.115; chloroform).

EXAMPLES 7 AND 8

(2S,4S)-1-[5-Chloro-1-[(2,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidine-carboxamide, Laevorotatory Isomer and Dextrorotatory Isomer (I): $R_1$=Cl; $R_2$=H; $R_3$=OCH$_3$; $R_4$=H; $R_5$=N(CH$_3$)$_2$; $R_6$=H; $R_7$=2-OCH$_3$; $R_8$=OCH$_3$ A mixture of 0.82 g of the compound obtained in Preparation 3.32 (mixture of diastereoisomers) in 5 ml of DMF is cooled to 4° C., under a nitrogen atmosphere, 0.076 g of 60% sodium hydride in oil is added and the mixture is stirred at 4° C. for 30 minutes. 0.451 g of 2,4-dimethoxybenzenesulphonyl chloride is then added and the mixture is stirred for 3 hours at RT. 50 ml of water are added to the reaction mixture, the resulting mixture is extracted with EtOAc, the organic phase is washed with 5% Na$_2$CO$_3$ solution, with saturated NaCl solution and dried over Na$_2$SO$_4$, and the solvent is evaporated off under vacuum. The residue is chromatographed on alumina, eluting with a DCM/MeOH mixture (99.2/0.8; v/v). The two diastereoisomers are separated:

the less polar: compound of Example 7, 0.122 g of which is collected after crystallization from hexane; m.p=151° C.

$\alpha_D^{25}$=−154° (c=0.1; chloroform)

the more polar, compound of Example 8, which is obtained after crystallization from a DCM/iso-ether mixture; m.p.=283° C.

$\alpha_D^{25}$=+140° (c=0.1; chloroform)

Working according to the procedures described in the Examples above, starting with the compounds of formula (II) described in Preparations 3 and 2,4-dimethoxybenzenesulphonyl chloride, the compounds according to the invention collated in Table I below are prepared:

TABLE I

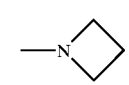

(I)

| Examples | R1 | R2 | R3 | R4 | R5 | R6 | Solvate, hydrate; m.p.° C.; crystallization solvent; $\alpha_D^{25}$ (chloroform) |
|---|---|---|---|---|---|---|---|
| 9 (a) | CH$_3$ | H | OCH$_3$ | H | —N(CH$_3$)$_2$ | H | 0.65 H$_2$O<br>162–164<br>iso-ether<br>−202.8° (c = 0.139) |
| 10 (b) | Cl | H | OCH$_3$ | H | —N⟨azetidinyl⟩ | H | 0.25 H$_2$O<br>161–162<br>iso-ether<br>−205.9° (c = 0.135) |
| 11 (c) | OCF$_3$ | H | OCH$_3$ | H | —N(CH$_3$)$_2$ | H | —<br>147<br>DCM/hexane<br>−223° (c = 0.13) |
| 12 (d) | Cl | 6-CH$_3$ | OCH$_3$ | H | —N(CH$_3$)$_2$ | H | —<br>—<br>iso-ether<br>−162.1° (c = 0.103) |
| 13 (e) | CH$_3$ | 6-CH$_3$ | Cl | H | —N(CH$_3$)$_2$ | H | 1 H$_2$O<br>232<br>DCM/iso-ether<br>−239° (c = 0.1) |
| 14 (f) | Cl | H | OCH$_3$ | 3-OCH$_3$ | —N(CH$_3$)$_2$ | —CH$_3$ | —<br>233–234<br>DCM/iso-ether<br>−198° (c = 0.11) |

TABLE I-continued (I)

[Structure of compound (I) with substituents R1, R2, R3, R4, R5, R6 on indoline-pyrrolidine scaffold with 2,4-dimethoxybenzenesulfonyl group]

| Examples | R1 | R2 | R3 | R4 | R5 | R6 | Solvate, hydrate; m.p.° C.; crystallization solvent; $\alpha_D^{25}$ (chloroform) |
|---|---|---|---|---|---|---|---|
| 15 (g) | Cl | 6-CF$_3$ | OCH$_3$ | H | —N(CH$_3$)$_2$ | —CH$_3$ | —<br>230–231<br>DCM/iso-ether<br>−170° (c = 0.11) |
| 16 (h) | CH$_3$ | 6-Cl | OCH$_3$ | H | —N(CH$_3$)$_2$ | —CH$_3$ | —<br>238–240<br>DCM/iso-ether<br>−163.2° (c = 0.12) |
| 17 (i) | Cl | H | OCH$_3$ | H | —N(CH$_3$)$_2$ | —CH$_2$CH$_3$ | —<br>169<br>iso-ether/hexane<br>−207° (c = 0.2) |
| 18 (j) | Cl | H | OCH$_3$ | 3-OCH$_3$ | —N(CH$_3$)$_2$ | H | —<br>148–150<br>DCM/iso-ether<br>−207.3° (c = 0.11) |
| 19 (k) | Cl | 6-Cl | Cl | H | —N(CH$_3$)$_2$ | H | —<br>181<br>iso-ether<br>−265.3° (c = 0.17) |
| 20 (l) | Cl | H | OCH$_3$ | H | OCH$_3$ | H | —<br>185–186<br>DCM/iso-ether<br>−180.9° (c = 0.15) |
| 21 (m) | Cl | 6-CH$_3$ | OCH$_3$ | H | OCH$_3$ | H | —<br>226<br>DCM/iso-ether<br>−131° (c = 0.17) |
| 22 (n) | Cl | H | OCH$_2$CH$_3$ | H | —N(CH$_3$)$_2$ | H | —<br>135–149<br>ether/iso-ether<br>−188.3° (c = 0.11) |
| 23 (o) | Cl | H | OCF$_3$ | H | —N(CH$_3$)$_2$ | H | —<br>—<br>—<br>−105° (c = 0.12) |
| 24 (p) | Cl | H | F | 3-F | —N(CH$_3$)$_2$ | H | —<br>—<br>—<br>−174° (c = 0.15) |
| 25 (q) | Cl | H | OCH$_3$ | 4-OCH$_3$ | —N(CH$_3$)$_2$ | H | —<br>183<br>iso-ether<br>−194° (c = 0.16) |
| 26 (r) | Cl | H | 2,3-O—CH$_2$—O— | | —N(CH$_3$)$_2$ | H | —<br>192<br>iso-ether<br>−200° (c = 0.16) |
| 27 (s) | Cl | 6-Cl | OCH$_3$ | H | —N(CH$_3$)$_2$ | H | —<br>160–161<br>iso-ether/DCM |

TABLE I-continued (I)

[Structure: indolin-2-one core with R₁, R₂ on benzene ring; R₃, R₄ on phenyl substituent; N-SO₂-(2,4-dimethoxyphenyl); spiro-linked pyrrolidine bearing OR₆ (R configuration) and C(=O)–R₅ (S configuration)]

| Examples | R1 | R2 | R3 | R4 | R5 | R6 | Solvate, hydrate; m.p.° C.; crystallization solvent; α$_D^{25}$ (chloroform) |
|---|---|---|---|---|---|---|---|
| | | | | | | | −138.8° (c = 0.11) |

(a) This compound is prepared according to the procedure described in Example 3, starting with the compound obtained in Preparation 3.6, isomer B. The product is chromatographed on silica gel, eluting with a DCM/MeOH mixture (97/3; v/v).
(b) This compound is prepared according to the procedure described in Example 3, starting with the compound obtained in Preparation 3.8, isomer B. The product is chromatographed on silica gel, eluting with a DCM/MeOH mixture (96/4; v/v).
(c) This compound is prepared according to the procedure described in Example 3, starting with the compound obtained in Preparation 3.10, isomer B. The product is chromatographed on silica gel, eluting with a DCM/MeOH mixture (96/4; v/v).
(d) This compound is prepared according to the procedure described in Example 3, starting with the compound obtained in Preparation 3.12, isomer B. The product is chromatographed on silica gel, eluting with a DCM/MeOH mixture (96/4; v/v).
(e) This compound is prepared according to the procedure described in Example 1, starting with the compound obtained in Preparation 3.14, isomer B. The product is chromatographed on silica gel, eluting with a DCM/MeOH mixture (98.5/1.5; v/v).
(f) This compound is prepared according to the procedure described in Example 1, starting with the compound obtained in Preparation 3.16, isomer B. The product is chromatographed on silica gel, eluting with a DCM/MeOH mixture (98.5/1.5; v/v).
(g) This compound is prepared according to the procedure described in Example 1, starting with the compound obtained in Preparation 3.18, isomer B. The product is chromatographed on silica gel, eluting with a DCM/MeOH mixture (98/2; v/v).
(h) This compound is prepared according to the procedure described in Example 1, starting with the compound obtained in Preparation 3.22, isomer B. The product is chromatographed on silica gel, eluting with a DCM/MeOH mixture (98.5/1.5; v/v).
(i) This compound is prepared according to the procedure described in Example 3, starting with the compound obtained in Preparation 3.24, isomer B. The product is chromatographed on silica gel, eluting with a DCM/EtOAc mixture (80/20; v/v).
(j) This compound is prepared according to the procedure described in Example 3, starting with the compound obtained in Preparation 3.26, isomer B. The product is chromatographed on silica gel, eluting with a DCM/MeOH mixture (91/9; v/v).
¹H NMR: DMSO-d₆: δ (ppm): 1.4 to 3.3: m: 10H; 3.4 to 3.95; 3s: 9H; 4.2 to 5.0: m: 3H; 6.6 to 8.0: m: 9H.
(k) This compound is prepared according to the procedure described in Example 3, starting with the compound obtained in Preparation 3.28, isomer B.
(l) This compound is prepared according to the procedure described in Example 3, starting with the compound obtained in Preparation 3.30, isomer B. The product is chromatographed on silica gel, eluting with a DCM/MeOH mixture (97/3; v/v).
(m) This compound is prepared according to the procedure described in Example 3, starting with the compound obtained in Preparation 3.31 (mixture of diastereoisomers). The product is chromatographed on silica gel, eluting with a DCM/EtOAc mixture (50/50; v/v) and the (−) isomer is separated out.
(n) This compound is prepared according to the procedure described in Example 3, starting with the compound obtained in Preparation 3.33. The product is chromatographed on silica gel, eluting with a DCM/MeOH mixture (95.5/4.5; v/v).
(o) This compound is prepared according to the procedure described in Example 3, starting with the compound obtained in Preparation 3.35, isomer B.
(p) This compound is prepared according to the procedure described in Example 3, starting with the compound obtained in Preparation 3.37, isomer B. The product is chromatographed on alumina, eluting with a DCM/EtOAc mixture (97/3; v/v).
(q) This compound is prepared according to the procedure described in Example 3, starting with the compound obtained in Preparation 3.39, isomer B. The product is chromatographed on silica gel, eluting with DCM.

TABLE I-continued (I)

[Structure of compound (I) as shown]

| Examples | R1 | R2 | R3 | R4 | R5 | R6 | Solvate, hydrate;<br>m.p.° C.;<br>crystallization solvent;<br>$\alpha_D^{25}$ (chloroform) |
|---|---|---|---|---|---|---|---|

(r) This compound is prepared according to the procedure described in Example 3, starting with the compound obtained in Preparation 3.40. The product is chromatographed on silica gel, eluting with DCM and then with a DCM/MeOH mixture (99/1; v/v).
(s) This compound is prepared according to the procedure described in Example 3, starting with the compound obtained in Preparation 3.42. The product is chromatographed on silica gel, eluting with a DCM/MeOH mixture (96/4; v/v).

EXAMPLE 28

Tert-Butyl 2-[[(3R,5S)-1-[5-chloro-1-[(2,4-dimethoxyphenyl)sulphonyl]-3-(2-methoxyphenyl)-2-oxo-2,3-dihydro-1H-indol-3-yl]-5-[(dimethylamino)carbonyl]-3-pyrrolidinyl]oxy]acetate, Laevorotatory Isomer.

(I): $R_1$=Cl; $R_2$=H; $R_3$=OCH$_3$; $R_4$=H; $R_5$=N(CH$_3$)$_2$; $R_6$=—CH$_2$COOC(CH$_3$)$_3$; $R_7$=2-OCH$_3$; $R_8$=OCH$_3$.

This compound is prepared according to the procedure described in Example 3, starting with 2.9 g of the compound obtained in Preparation 3.44 (isomer B), 0.233 g of 60% sodium hydride in oil, 15 ml of DMF and 1.25 g of 2,4-dimethoxybenzenesulphonyl chloride. The product is chromatographed on silica gel, eluting with a DCM/EtOAc mixture (80/20; v/v). 3 g of the expected product are obtained after crystallization from hexane.

$\alpha_D^{20}$=−159° (c=0.23; chloroform).

EXAMPLE 29

2-[[(3R,5S)-1-[5-Chloro-1-[(2,4-dimethoxyphenyl)sulphonyl]-3-(2-methoxyphenyl)-2-oxo-2,3-dihydro-1H-indol-3-yl]-5-[(dimethylamino)carbonyl]-3-pyrrolidinyl]oxy]acetic acid 0.55 trifluoroacetate, Laevorotatory Isomer.

(I), TFA: $R_1$=Cl; $R_2$=H; $R_3$=OCH$_3$; $R_4$=H; $R_5$=N(CH$_3$)$_2$; $R_6$=—CH$_2$COOH; $R_7$=2-OCH$_3$; $R_8$=OCH$_3$.

A mixture of 3 g of the compound obtained in Example 28 and 15 ml of TFA in 15 ml of DCM is stirred for 3 hours at RT. The reaction mixture is concentrated under vacuum, the residue is taken up in iso-ether and the precipitate formed is spin-filtered off. 2.2 g of the expected product are obtained.

$\alpha_D^{20}$=−179° (c=0.31; chloroform).

EXAMPLE 30

(2S,4R)-1-[5-Chloro-1-[(2,4-dimethoxyphenyl)sulphonyl]-3-(2-methoxyphenyl)-2-oxo-2,3-dihydro-1H-indol-3-yl]-4-[2-[[2-hydroxy-1-(hydroxymethyl)-1-methylethyl]amino]-2-oxoethoxy]-N,N-dimethyl-2-pyrrolidinecarboxamide, laevorotatory isomer.

(I): $R_1$=Cl; $R_2$=H; $R_3$ OCH$_3$; $R_4$=H; $R_5$=N(CH$_3$)$_2$; $R_6$=—CH$_2$CONHC(CH$_3$) (CH$_2$OH)$_2$; $R_7$=2-OCH$_3$; $R_8$=OCH$_3$.

A mixture of 0.5 g of the compound obtained in Example 29, 0.085 g of 2-amino-2-methyl-1,3-propanediol, 0.290 g of BOP and 0.187 g of triethylamine in 20 ml of DCM is stirred for 3 hours at RT. The reaction mixture is diluted by addition of DCM, the organic phase is washed with water, with saturated Na$_2$CO$_3$ solution and dried over Na$_2$SO$_4$, and the solvent is evaporated off under vacuum. The residue is chromatographed on silica gel, eluting with a DCM/MeOH mixture (94/6; v/v). 0.31 g of the expected product is obtained after crystallization from iso-ether; m.p.=154° C.

$\alpha_D^{20}$=−142 (c=0.19; chloroform).

EXAMPLE 31

(2S,4R)-1-[5-Chloro-1-[(2,4-dimethoxyphenyl)sulphonyl]-3-(2-methoxyphenyl)-2-oxo-2,3-dihydro-1H-indol-3-yl]-N,N-dimethyl-4-[2-oxo-2-(1-piperazinyl)ethoxy]-2-pyrrolidinecarboxamide bis(trifluoroacetate), laevorotatory isomer.

(I), 2TFA: $R_1$=Cl; $R_2$=H; $R_3$=OCH$_3$; $R_4$H; $R_5$=−N(CH$_3$)$_2$;

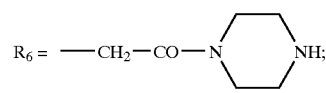

$R_7$=2-OCH$_3$; $R_8$=OCH$_3$.

A)
A mixture of 0.7 g of the compound obtained in Example 29, 0.2 g of 1-(tert-butoxycarbonyl)piperazine, 0.404 g of BOP and 0.263 g of triethylamine in 20 ml of DCM is stirred for 2 hours at RT. Water is added to the reaction mixture and the resulting mixture is extracted with DCM, the organic phase is washed with saturated $Na_2CO_3$ solution and dried over $Na_2SO_4$, and the solvent is evaporated off under vacuum. The residue is chromatographed on silica gel, eluting with a DCM/MeOH mixture (97/3; v/v). The product thus obtained is taken up in hexane and the precipitate formed is spin-filtered off to give 0.7 g.

B)

A mixture of 0.7 g of the compound obtained in step A and 10 ml of TFA in 10 ml of DCM is stirred for 3 hours. The reaction mixture is concentrated under vacuum, the residue is taken up in ether and the precipitate formed is spin-filtered off. 0.6 g of the expected product is obtained; m.p.=166° C.

$\alpha_D^{20}$=−133° (c=0.27; chloroform).

EXAMPLE 32

(2S,4R)-1-[(2,4-Dimethoxyphenyl)sulphonyl]-3-(2-methoxyphenyl)-2-oxo-2,3-dihydro-1H-indol-3-yl]-N,N-dimethyl-4-[2-oxo-2-(4-morpholinyl)ethoxy]-2-pyrrolidinecarboxamide, laevorotatory isomer.

(I): $R_1$=Cl; $R_2$=H; $R_3$=$OCH_3$; $R_4$=H; $R_5$=−$N(CH_3)_2$;

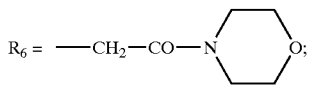

$R_7$=2-$OCH_3$; $R_8$=$OCH_3$.

A mixture of 0.6 g of the compound obtained in Example 29, 0.085 g of morpholine, 0.347 g of BOP and 0.227 g of triethylamine in 20 ml of DCM is stirred for 2 hours at RT. The reaction mixture is extracted with DCM, the organic phase is washed with water and dried over $Na_2SO_4$, and the solvent is evaporated off under vacuum. The residue is chromatographed on silica gel, eluting with a DCM/MeOH mixture (95/5; v/v). 0.53 g of the expected product is obtained after crystallization from iso-ether; m.p.=210° C.

$\alpha_D^{20}$=−153° (c=0.28; chloroform).

EXAMPLES 33 AND 34

(3R,5S)-1-[5-Chloro-1-[(2,4-dimethoxyphenyl) sulphonyl]-3-(2-methoxyphenyl)-2-oxo-2,3-dihydro-1H-indol-3-yl]-5-[(dimethylamino)carbonyl]-3-pyrrolidinyl 3-(4-morpholinyl)propanoate, laevorotatory isomer and dextrorotatory isomer.

(I): $R_1$=Cl; $R_2$=H; $R_3$=$OCH_3$; $R_4$=H; $R_5$=−$N(CH_3)_2$;

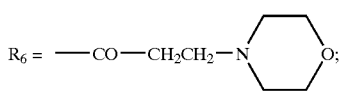

$R_7$=2-$OCH_3$; $R_8$=$OCH_3$.

These compounds are prepared according to the procedure described in Example 3, starting with 3.1 g of the compound obtained in Preparation 3.45, 20 ml of DMF, 0.238 g of 60% sodium hydride in oil and 1.27 g of 2,4-dimethoxybenzenesulphonyl chloride. The product is chromatographed on silica gel, eluting with a DCM/MeOH mixture (90/10; v/v). The two diastereoisomers are separated:

the less polar: compound of Example 33, 2.8 g of which are obtained after solidification in hexane.

$\alpha_D^{20}$=−154° (c=0.3; chloroform).

the more polar: compound of Example 34, 1.3 g of which are obtained after solidification in hexane.

$\alpha_D^{25}$=+127° (c=0.29; chloroform).

What is claimed is:

1. A compound of formula:

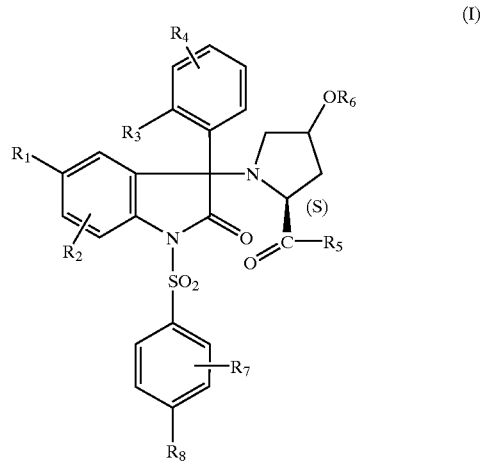

in which:

$R_1$ represents a halogen atom; a ($C_1$–$C_4$)alkyl; a ($C_1$–$C_4$)alkoxy; a trifluoromethyl radical; a trifluoromethoxy radical;

$R_2$ represents a hydrogen atom; a halogen atom; a ($C_1$–$C_4$)alkyl; a ($C_1$–$C_4$)alkoxy; a trifluoromethyl radical;

or $R_2$ is in position -6- of the indol-2-one ring and $R_1$ and $R_2$ together represent a divalent trimethylene radical;

$R_3$ represents a halogen atom; a hydroxyl; a ($C_1$–$C_2$)alkyl; a ($C_1$–$C_2$)alkoxy; a trifluoromethoxy radical;

$R_4$ represents a hydrogen atom; a halogen atom; a ($C_1$–$C_2$)alkyl; a ($C_1$–$C_2$)alkoxy;

$R_4$ is in position -3- of the phenyl and $R_3$ and $R_4$ together represent a methylenedioxy radical;

$R_5$ represents an ethylamino group; a dimethylamino group; an azetidin-1-yl radical; a ($C_1$–$C_2$)alkoxy;

$R_6$ represents a hydrogen atom; a ($C_1$–$C_4$)alkyl; a group —$(CH_2)_n$-CO—$R_9$; a group —CO—$(CH_2)_n$-$NR_{10}R_{11}$;

$R_7$ represents a ($C_1$–$C_4$)alkoxy;

$R_8$ represents a ($C_1$–$C_4$)alkoxy;

$R_9$ represents a hydroxyl; a ($C_1$–$C_4$)alkoxy; a group —$NR_{12}R_{13}$;

$R_{10}$ and $R_{11}$ each independently represent a ($C_1$–$C_4$)alkyl;

or $R_{10}$ and $R_{11}$, together with the nitrogen atom to which they are attached, constitute a heterocyclic radical chosen from: azetidin-1-yl, pyrrolidin-1-yl, piperid-1-yl, piperazin-1-yl, morpholin-4-yl or thiomorpholin-4-yl;

$R_{12}$ represents a hydrogen or a ($C_1$–$C_4$)alkyl;

$R_{13}$ represents a ($C_1$–$C_4$)alkyl; a —$C(CH_3)_2CH_2OH$ group; a —$C(CH_3)(CH_2OH)_2$ group; a —$C(CH_2OH)_3$ group;

or $R_{12}$ and $R_{13}$, together with the nitrogen atom to which they are attached, constitute a heterocyclic radical chosen from: azetidin-1-yl, pyrrolidin-1-yl, piperid-1-yl, piperazin-1-yl, morpholin-4-yl or thiomorpholin-4-yl;

n is 1 or 2; or a solvate, hydrate or acid-addition salt thereof.

2. A compound according to claim 1, in the form of optically pure isomers.

3. A compound according to claim 1, of formula:

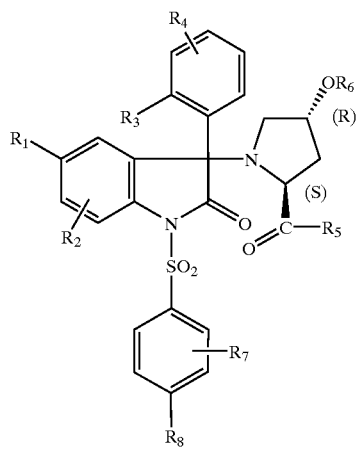

in which:
the carbon atom bearing substituent $OR_6$ has the (R) configuration and the carbon atom in position 3 of the indol-2-one has either the (R) configuration or the (S) configuration.

4. A compound according to claim 3, in the form of the levorotatory isomer.

5. A compound according to claim 4 in which:
$R_1$ represents a chlorine atom, a methyl radical or a trifluoromethoxy radical;
$R_2$ represents a hydrogen atom or is in position -6- of the indol-2-one and represents a chlorine atom, a methyl radical, a methoxy radical or a trifluoromethyl radical;
$R_3$ represents a chlorine atom, a fluorine atom, a methoxy radical or an ethoxy radical;
$R_4$ represents a hydrogen atom or is in position -3- or -4- of the phenyl and represents a fluorine atom or a methoxy radical;
or $R_4$ is in position -3- of the phenyl and, together with $R_3$, represent a methylenedioxy radical;
$R_5$ represents a dimethylamino radical or a methoxy radical;
$R_6$ represents a hydrogen atom; a methyl radical; an ethyl radical; a tert-butyloxycarbonylmethyl radical; a carboxymethyl radical; a [[2-hydroxy-1-(hydroxymethyl)-1-methylethyl]amino]carbonylmethyl radical; a (1-piperazinyl)carbonylmethyl radical; a (4-morpholinyl)carbonylmethyl radical; a 3-(4-morpholinyl)propanoyl radical;
$R_7$ is in position -2- of the phenyl and represents a methoxy radical;
$R_8$ represents a methoxy radical; or
an acid-addition salt, solvate or hydrate thereof.

6. A compound according to claim 5 selected from the group consisting of:
-(2S,4R)-1-[5-Chloro-1-[2,4-dimethoxyphenyl)sulphonyl]-3-(2-methoxyphenyl)-2-oxo-2,3-dihydro-1H-indol-3yl]-4-hydroxy-N,N-dimethyl-2-pyrrolidinecarboxamide, levorotatory isomer;
-(2S,4R)-1-[(2,4-dimethoxyphenyl)sulphonyl]-3-(2-methoxyphenyl)-2-oxo-2,3-dihydro-1H-indol-3-yl]-4-methoxy-N,N-dimethyl-2-pyrrolidinecarboxamide, levorotatory isomer;
-(2S,4R)-1-[5-Chloro-3-(2-chlorophenyl)-1-[(2,4-dimethoxyphenyl)sulphonyl]-2-oxo-2,3-dihydro-1H-indol-3yl]-4-hydroxy-N,N-dimethyl-2-pyrrolidinecarboxamide, levorotatory isomer;
(2S,4R)-1-[5-Chloro-3-(2-chlorophenyl)-1-[(2,4-dimethoxyphenyl)sulphonyl]-6-methoxy-2-oxo-2,3-dihydro-1H-indol-3-yl]-4-methoxy-N,N-dimethyl-2-pyrrolidine-carboxamide, levorotatory isomer;
(2S,4R)-1-[5-Chloro-1-[(3,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide, levorotatory isomer;
Methyl (2S,4R)-1-[5-chloro-3-(2-methoxyphenyl)-1-[(3,4-dimethoxyphenyl)sulphonyl]-2-oxo-2,3-dihydro-1H-indol-3-yl]-4-hydroxy-2-pyrrolidine-carboxylate, levorotatory isomer;
(2S,4R)-1-[5-Methyl-1-[(2,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide, levorotatory isomer;
(2S,4R)-1-[5-Chloro-1-[(2,4-dimethoxyphenyl)sulphonyl]-3-(2-methoxyphenyl)-2-oxo-2,3-dihydro-1H-indol-3-yl]-2-(azetidin-1-ylcarbonyl)-4-hydroxypyrrolidinecarboxamide, levorotatory isomer;
(2S,4R)-1-[5-Trifluoromethoxy-1-[(2,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide, levorotatory isomer;
(2S,4R)-1-[5-Chloro-1-[(2,4-dimethoxyphenyl)sulphonyl]3-(2methoxyphenyl)-6-methyl-2-oxo-2,3-dihydro-1H-indol-3-yl]-4-hydroxy-N,N-dimethyl-2-pyrrolidinecarboxamide, levorotatory isomer;
(2S,4R)-1-[3-(2-Chlorophenyl)-1-[(2,4-dimethoxyphenyl)sulphonyl]-5,6-dimethyl-2-oxo-2,3-dihydro-1H-indol-3-yl]-4-hydroxy-N,N-dimethyl-2-pyrrolidinecarboxamide, levorotatory isomer;
(2S,4R)-1-[5-Chloro-1-[(2,4-methoxyphenyl)sulphonyl]-3-(2,3-dimethoxyphenyl)-2-oxo-2,3-dihydro-1H-indol-3-yl]-4-methoxy-N,N-dimethyl-2-pyrrolidinecarboxamide, levorotatory isomer;
(2S,4R)-1-[5-Chloro-1-[(2,4-dimethoxyphenyl)sulphonyl]-3-(2-methoxyphenyl)-6-trifluoromethyl-2-oxo-2,3-dihydro-1H-indol-3-yl]-4-methoxy-N,N-dimethyl-2-pyrrolidinecarboxamide, levorotatory isomer;
(2S,4R)-1-[6-Chloro-1-[(2,4-dimethoxyphenyl)sulphonyl]-3-(2methoxyphenyl)-5-methyl-2-oxo-2,3-dihydro-1H-indol-3-yl]-4-methoxy-N,N-dimethyl-2-pyrrolidinecarboxamide, levorotatory isomer;
(2S,4R)-1-[5-Chloro-1-[(2,4-dimethoxyphenyl)sulphonyl]-3-(2-methoxyphenyl)-2-oxo-2,3-dihydro-1H-indol-3-yl]-4-ethoxy-N,N-dimethyl-2-pyrrolidinecarboxamide levorotatory isomer;
(2S,4R)-1-[(5-Chloro-1-[(2,4-dimethoxyphenyl)sulphonyl]-3-(2,3-dimethoxyphenyl)-2-oxo-2,3-dihydro-1H-indol-3-yl]-4-hydroxy-N,N-dimethyl-2-pyrrolidinecarboxamide, levorotatory isomer;
(2S,4R)-1-[5,6-Dichloro-3-(2-chlorophenyl)-1-[(2,4-dimethoxyphenyl)sulphonyl]-2-oxo-2,3-dihydro-1H-indol-3-yl]-4-hydroxy-N,N-dimethyl-2-pyrrolidinecarboxamide, levorotatory isomer;
Methyl (2S,4R)-1-(5-chloro-1-[(2,4-dimethoxyphenyl)sulphonyl]-3-(2-methoxyphenyl)-2-oxo-2,3-dihydro- 1H-indol-3-yl]-4-methoxy-2-pyrrolidinecarboxylate, levorotatory isomer;

Methyl (2S,4R)-1-[5-chloro- 1-[(2,4-dimethoxyphenyl) sulphonyl]-3-(2-methoxyphenyl)-6-methyl-2-oxo-2,3-dihydro-1H-indol-3-yl]-4-methoxy-2-pyrrolidine-carboxylate, levorotatory isomer;

(2S,4R)-1-[5-Chloro-1-[(2,4-dimethoxyphenyl) sulphonyl]-3-(2-ethoxyphenyl)-2-oxo-2,3-dihydro-1H-indol-3-yl]-4-hydroxy-N,N-dimethyl-2-pyrrolidinecarboxamide, levorotatory isomer;

(2S,4R)-1-[5-Chloro-1-[(2,4-dimethoxyphenyl) sulphonyl]-3-(2,3-difluorophenyl)-2-oxo-2,3-dihydro-1H-indol-3-yl]-4-hydroxy-N,N-dimethyl-2-pyrrolidinecarboxamide, levorotatory isomer;

(2S,4R)-1-[5-Chloro-1-[(2,4-dimethoxyphenyl) sulphonyl]-3-(2,4-dimethoxyphenyl)-2-oxo-2,3-dihydro-1H-indol-3-yl]-4-hydroxy-N,N-dimethyl-2-pyrrolidinecarboxamide, levorotatory isomer;

(2S,4R)-1-[5-Chloro-1-[(2,4-dimethoxyphenyl) sulphonyl]-3-(1,3-benzodioxol-4-yl)-2-oxo-2,3-dihydro-1H-indol-3-yl]-4-hydroxy-N,N-dimethyl-2-pyrrolidinecarboxamide, levorotatory isomer;

(2S,4R)-1-[5,6-Dichloro-1-[(2,4-dimethoxyphenyl) sulphonyl]-3-(2-methoxyphenyl)-2-oxo-2,3-dihydro-1H-indol-3-yl]-4-hydroxy-N,N-dimethyl-2-pyrrolidinecarboxamide, levorotatory isomer;

tert-Butyl 2-[[(3R,5S)-1-[5-chloro-1-[(2,4-dimethoxyphenyl)sulphonyl]-3-(2-methoxyphenyl)-2-oxo-2,3-dihydro-1H-indol-3-yl]-5-[(dimethylamino)carbonyl]-3-pyrrolidinyl]oxy]acetate, levorotatory isomer;

2-[[(3R,5S)-1-[5-Chloro-1-[(2,4-dimethoxyphenyl) sulphonyl]-3(2-methoxyphenyl)-2-oxo-2,3-dihydro-1H-indol-3-yl]-5-[dimethylamino)carbonyl]-3-pyrrolidinyl]oxy]acetic acid, levorotatory isomer;

(2S,4R)-1-[5-Chloro-1-[(2,4-dimethoxyphenyl) sulphonyl]-3-(2-methoxyphenyl)-2-oxo-2,3-dihydro-1H-indol-3-yl]-4-[2-[[2-hydroxy-1-(hydroxymethyl)-1-methylethyl]amino]-2-oxoethoxy]-N,N-dimethyl-2-pyrrolidinecarboxamide, levorotatory isomer;

(2S,4R)-1-[5-Chloro-1-[(2,4-dimethoxyphenyl) sulphonyl]-3-(2-methoxyphenyl-2-oxo-2,3-dihydro-1H-indol-3-yl]-N,N-dimethyl-4-[2-oxo-2-(1-piperazinyl)ethoxy]-2-pyrrolidinecarboxamide, levorotatory isomer;

(2S,4R)-1-[[(2,4-Dimethoxyphenyl)sulphonyl]-3-(2-methoxyphenyl)-2-oxo-2,3-dihydro-1H-indol-3-yl]-N,N-dimethyl-4-[2-oxo-2-(4-morpholinyl)ethoxy]-2-pyrrolidinecarboxamide, levorotatory isomer; and (3R,5S)-1-[5-Chloro-1-[(2,4-dimethoxyphenyl) sulphonyl]-3-(2-methoxyphenyl)-2-oxo-2,3-dihydro-1H-indol-3-yl]-5-[dimethylamino)carbonyl]-3-pyrrolidinyl 3-(4-morpholinyl)propanoate, levorotatory isomer; or the acid-addition salts, solvates or hydrates thereof.

7. A pharmaceutical composition comprising a compound according to claim 1 and a pharmaceutically acceptable excipient.

8. A compound according to claim 1 wherein:

$R_3$ is halogen, hydroxyl or $(C_1-C_2)$ alkoxy, and $R_6$ is hydrogen or $(C_1-C_4)$ alkyl.

9. The levorotatory isomer of (2S,4R)-1-[5-chloro-1-[(2,4-dimethoxyphenyl)sulphonyl]-3-(2-methoxyphenyl)-2-oxo-2,3-dihydro-1H-indol-3-yl]-4-hydroxy-N,N-dimethyl-2-pyrrolidinecarboxamide.

10. A pharmaceutical composition comprising a compound according to claim 3 and a pharmaceutically acceptable excipient.

11. A pharmaceutical composition comprising a compound according to claim 5 and a pharmaceutically acceptable excipient.

12. A pharmaceutical composition comprising a compound according to claim 6 and a pharmaceutically acceptable excipient.

13. A pharmaceutical composition comprising a compound according to claim 9 and a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 6,730,695 B2 | Page 1 of 7 |
| APPLICATION NO. | : 10/182048 | |
| DATED | : May 4, 2004 | |
| INVENTOR(S) | : Richard Roux et al. | |

It is certified that error appears in the above-identified patent and that said Letters Patent is hereby corrected as shown below:

Column 58,
Lines 26-67, reads:
"in which:
- $R_1$ represents a halogen atom; a $(C_1-C_4)$alkyl; a $(C_1-C_4)$alkoxy; a trifluoromethyl radical; a trifluoromethoxy radical;
- $R_2$ represents a hydrogen atom; a halogen atom; a $(C_1-C_4)$alkyl; a $(C_1-C_4)$alkoxy; a trifluoromethyl radical;
- or $R_2$ is in position -6- of the indol-2-one ring and $R_1$ and $R_2$ together represent a divalent trimethylene radical;
- $R_3$ represents a halogen atom; a hydroxyl; a $(C_1-C_2)$alkyl; a $(C_1-C_2)$alkoxy; a trifluoromethoxy radical;
- $R_4$ represents a hydrogen atom; a halogen atom; a $(C_1-C_2)$alkyl; a $(C_1-C_2)$alkoxy;
- or $R_4$ is in position -3- of the phenyl and $R_3$ and $R_4$ together represent a methylenedioxy radical;
- $R_5$ represents an ethylamino group; a dimethylamino group; an azetidin-1-yl radical; a $(C_1-C_2)$alkoxy;
- $R_6$ represents a hydrogen atom; a $(C_1-C_4)$alkyl; a group $-(CH_2)n-CO-R_9$; a group $-CO-(CH_2)n-NR_{10}R_{11}$;
- $R_7$ represents a $(C_1-C_4)$alkoxy;
- $R_8$ represents a $(C_1-C_4)$alkoxy;
- $R_9$ represents a hydroxyl; a $(C_1-C_4)$alkoxy; a group $-NR_{12}R_{13}$;
- $R_{10}$ and $R_{11}$ each independently represent a $(C_1-C_4)$alkyl;
- or $R_{10}$ and $R_{11}$, together with the nitrogen atom to which they are attached, constitute a heterocyclic radical chosen from: azetidin-1-yl, pyrrolidin-1-yl, piperid-1-yl, piperazin-1-yl, morpholin-4-yl or thiomorpholin-4-yl;
- $R_{12}$ represents a hydrogen or a $(C_1-C_4)$alkyl;
- $R_{13}$ represents a $(C_1-C_4)$alkyl; a $-C(CH_3)_2CH_2OH$ group; a $-C(CH_3)(CH_2OH)_2$ group; a $-C(CH_2OH)_3$ group;
-or $R_{12}$ and $R_{13}$, together with the nitrogen atom to which they are attached, constitute a heterocyclic radical chosen from: azetidin-1-yl, pyrrolidin-1-yl, piperid-1-yl, piperazin-1-yl, morpholin-4-yl or thiomorpholin-4-yl;
- n is 1 or 2; or a solvate, hydrate or acid-addition salt thereof.."
and should read,
-- in which:
- $R_1$ represents a halogen atom; a $(C_1-C_4)$alkyl; a $(C_1-C_4)$alkoxy; a trifluoromethyl radical; a trifluoromethoxy radical;
- $R_2$ represents a hydrogen atom; a halogen atom; a $(C_1-C_4)$alkyl; a $(C_1-C_4)$alkoxy; a trifluoromethyl radical;
- $R_3$ represents a halogen atom; a hydroxyl; a $(C_1-C_2)$alkyl; a $(C_1-C_2)$alkoxy; a trifluoromethoxy radical;
- $R_4$ represents a hydrogen atom; a halogen atom; a $(C_1-C_2)$alkyl; a $(C_1-C_2)$alkoxy;
- $R_5$ represents an ethylamino group; a dimethylamino group;

UNITED STATES PATENT AND TRADEMARK OFFICE
CERTIFICATE OF CORRECTION

PATENT NO. : 6,730,695 B2
APPLICATION NO. : 10/182048
DATED : May 4, 2004
INVENTOR(S) : Richard Roux et al.

It is certified that error appears in the above-identified patent and that said Letters Patent is hereby corrected as shown below:

Column 58 (cont'd),
- $R_6$ represents a hydrogen atom; a $(C_1-C_4)$alkyl;
- $R_7$ represents a $(C_1-C_4)$alkoxy; and
- $R_8$ represents a $(C_1-C_4)$alkoxy;
or a solvate, hydrate or acid-addition salt thereof. --.

Column 59,
Lines 30-56, reads "A compound according to claim 4 in which:
- $R_1$ represents a chlorine atom, a methyl radical or a trifluoromethoxy radical;
- $R_2$ represents a hydrogen atom or is in position -6- of the indol-2-one and represents a chlorine atom, a methyl radical, a methoxy radical or a trifluoromethyl radical;
- $R_3$ represents a chlorine atom, a fluorine atom, a methoxy radical or an ethoxy radical;
- $R_4$ represents is a hydrogen atom or is in position -3- or -4- of the phenyl and represents a fluorine atom or a methoxy radical;
- or $R_4$ is in position -3- of the phenyl and, together with $R_3$, represent a methylenedioxy radical;
- $R_5$ represents a dimethylamino radical or a methoxy radical;
- $R_6$ represents is a hydrogen atom; a methyl radical; an ethyl radical; a *tert*-butyloxycarbonylmethyl radical; a carboxymethyl radical; a [[2-hydroxy-1-(hydroxymethyl)-1-methylethyl]amino]carbonylmethyl radical; a (1-piperazinyl) carbonylmethyl radical; a (4-morpholinyl)carbonylmethyl radical; a 3-(4-morpholinyl) propanoyl radical;
- $R_7$ is in position -2- of the phenyl and represents a methoxy radical;
- $R_8$ represents a methoxy radical; or
an acid-addition salt, solvate or hydrate thereof."
and should read
-- A compound according to Claim 4 in which:
- $R_1$ represents a chlorine atom, a methyl radical or a trifluoromethoxy radical;
- $R_2$ represents a hydrogen atom or is in position -6- of the indol-2-one and represents a chlorine atom, a methyl radical, a methoxy radical or a trifluoromethyl radical;
- $R_3$ represents is a chlorine atom, a fluorine atom, a methoxy radical or an ethoxy radical;
- $R_4$ represents a hydrogen atom or is in position -3- or -4- of the phenyl and represents a fluorine atom or a methoxy radical;
- $R_5$ represents a dimethylamino radical;
- $R_6$ represents a hydrogen atom; a methyl radical; an ethyl radical;
- $R_7$ is in position -2- of the phenyl and represents a methoxy radical;
- $R_8$ represents a methoxy radical; or an acid-addition salt, solvate or hydrate thereof. --.

UNITED STATES PATENT AND TRADEMARK OFFICE
CERTIFICATE OF CORRECTION

PATENT NO. : 6,730,695 B2
APPLICATION NO. : 10/182048
DATED : May 4, 2004
INVENTOR(S) : Richard Roux et al.

It is certified that error appears in the above-identified patent and that said Letters Patent is hereby corrected as shown below:

Column 59,
Line 58, reads
"A compound according to claim 5 selected from the group consisting of:
- (2S, 4R)-1-[5-Chloro-1-[(2,4-dimethoxyphenyl)sulphonyl]-3-(2-methoxyphenyl)-2-oxo-2,3-dihydro-1*H*-indol-3-yl]-4-hydroxy-N,N-dimethyl-2-pyrrolidinecarboxamide, levorotatory isomer;
- (2S,4R)-1-[(2,4-dimethoxyphenyl)sulphonyl]-3-(2-methoxyphenyl)-2-oxo-2,3-dihydro-1*H*-indol-3-yl]-4-methoxy-N,N-dimethyl-2-pyrrolidinecarboxamide, levorotatory isomer; - (2S, 4R)-1-[5-Chloro-3-(2-chlorophenyl)-1-[(2,4-dimethoxyphenyl)sulphonyl]-2-oxo-2,3-dihydro-1*H*-indol-3-yl]-4-hydroxy-N,N-dimethyl-2-pyrrolidinecarboxamide, levorotatory isomer;
(2S, 4R)-1-[5-Chloro-3-(2-chlorophenyl)-1-[(2,4-dimethoxyphenyl)sulphonyl]-6-methoxy-2-oxo-2,3-dihydro-1*H*-indol-3-yl]-4-methoxy-N,N-dimethyl-2-pyrrolidine-carboxamide, levorotatory isomer;
(2S, 4R)-1-[5 Choro-1-[(3,4-dimethoxyphenyl)sulphonyl]-3-(2-methoxyphenyl)-2-oxo-2,3-dihydro-1*H*-indol-3-yl]-4-hydroxy-N,N-dimethyl-2-pyrrolidinecarboxamide, levorotatory isomer,
Methyl (2S, 4R-1-[5-chloro-3-(2-methoxyphenyl)-1-[(3,4-dimethoxyphenyl) sulphonyl]-2-oxo-2,3-dihydro-1*H*-indol-3-yl]-4-hydroxy-2-pyrrolidine-carboxylate, levorotatory isomer;
(2S, 4R)-1-[5- Methyl-1-[(2,4-dimethoxyphenyl)sulphonyl]-3-(2-methoxyphenyl)-2-oxo-2,3-dihydro-1*H*-indol-3-yl]-4-hydroxy-N,N-dimethyl-2-pyrrolidinecarboxamide, levorotatory isomer;
(2S, 4R)-1-[5-Chloro-1-[(2,4-dimethoxyphenyl)sulphonyl]-3-(2-methoxyphenyl)-2-oxo-2,3-dihydro-1*H*-indol-3-yl]-2-(azetidin-1-ylcarbonyl)-4-hydroxypyrrolidinecarboxamide, levorotatory isomer;
(2S, 4R)-1-[5-Trifluoromethoxy-1-[(2,4-dimethoxyphenyl)sulphonyl]-3-(2-methoxyphenyl)-2-oxo-2,3-dihydro-1*H*-indol-3-yl]-4-hydroxy-N,N-dimethyl-2-pyrrolidinecarboxamide, levorotatory isomer;
(2S, 4R)- 1-[5-Chloro-1-[(2,4-dimethoxyphenyl)sulphonyl]3-(2-methoxyphenyl)-6-methyl-2-oxo-2,3-dihydro-1*H*-indol-3-yl]-4-hydroxy-N,N-dimethyl-2-pyirolidinecarboxamide, levorotatory isomer;
(2S, 4R)-1-[3-(2-Chlorophenyl)-1-[(2,4-dimethoxyphenyl)sulphonyl)-5,6-dimethyl-2-oxo-2,3-dihydro-1*H*-indol-3-yl]-4-hydroxy-N,N-dimethyl-2-pryrrolidinecarboxamide, levorotatory isomer;
(2S, 4R)-1-[5-Chloro-1-[(2,4-dimethoxyphenyl)sulphonyl]-3-(2,3-dimethoxyphenyl)-2-oxo-2,3-dihydro-1*H*-indol-3-yl]-4-methoxy-N,N-dimethyl-2-pyrrolidinecarboxamide, levorotatory isomer;
(2S, 4R)-1-[5-Chloro-1-[(2,4-dimethoxyphenyl)sulphonyl]-3-(2-methoxyphenyl)-6-trifluoromethyl-2-oxo-2,3-dihydro-1*H*-indol-3-yl]-4-methoxy-N,N-dimethyl-2-pyrrolidinecarboxamide, levorotatory isomer;

UNITED STATES PATENT AND TRADEMARK OFFICE
CERTIFICATE OF CORRECTION

PATENT NO. : 6,730,695 B2
APPLICATION NO. : 10/182048
DATED : May 4, 2004
INVENTOR(S) : Richard Roux et al.

It is certified that error appears in the above-identified patent and that said Letters Patent is hereby corrected as shown below:

Column 59 (cont'd),
(2S, 4R)- 1-[6-Chloro-1-[(2,4-dimethoxyphenyl)sulphonyl]-3-(2-methoxyphenyl)-5-methyl-2-oxo-2,3-dihydro 1$H$-indol-3-yl]-4-methoxy-N,N-dimethyl-2-pyrrolidinecarboxamide, levorotatory isomer;
(2S, 4R)- 1-[5-Chloro-1-[(2,4-dimethoxyphenyl)sulphonyl]-3-(2-methoxyphenyl)-2-oxo-2,3-dihydro-1$H$ indol-3-yl]-4-ethoxy-N,N-dimethyl-2-pyrrolidinecarboxamide, levorotatory isomer;
(2S, 4R)-1-[5-Choro-1-[(2,4-dimethoxyphenyl)sulphonyl]-3-(2,3-dimethoxyphenyl)-2-oxo-2,3-dihydro-1$H$ indol-3-yl]-4-hydroxy-N,N-dimethyl-2-pyrrolidinecarboxamide, levorotatory isomer;
(2S, 4R)-1-[5,6-Dichloro-3-(2-chlorophenyl)-1-[(2,4-dimethoxyphenyl)sulphonyl]-2-oxo-2,3-dihydro-1$H$ indol-3-yl]-4-hydroxy-N,N-dimethyl-2-pyrrolidinecarboxamide, levorotatory isomer;
Methyl (2S, 4R)-1-[5-chloro-1-[(2,4-dimethoxyphenyl)sulphonyl]-3-(2-methoxyphenyl)-2-oxo-2,3-dihydro-1$H$-indol-3-yl]-4-methoxy-2-pyrrolidinecarboxylate, levorotatory isomer;
Methyl (2S, 4R)-1-[5-chloro-1-[(2,4-dimethoxyphenyl)sulphonyl]-3-(2-methoxyphenyl)-6-methyl-2-oxo-2,3-dihydro-1$H$-indol-3-yl]-4-methoxy-2-pyrrolidinecarboxylate, levorotatory isomer;
(2S, 4R)-1-[5 Chloro-1-[(2,4-dimethoxyphenyl)sulphonyl]-3-(2-ethoxyphenyl)-2-oxo-2,3-dihydro-1$H$-indol-3-yl]-4-hydroxy-N,N-dimethyl-2-pyrrolidinecarboxamide, levorotatory isomer;
(2S, 4R)-1-[5 Chloro-1-[(2,4-dimethoxyphenyl)sulphonyl]-3-(2,3-difluorophenyl)-2-oxo-2,3-dihydro-1$H$-indol-3-yl]-4-hydroxy-N,N-dimethyl-2-pyrrolidinecarboxamide, levorotatory isomer;
(2S, 4R)-1-[5-Chloro-1-[(2,4-dimethoxyphenyl)sulphonyl]-3-(2,4-dimethoxyphenyl)-2-oxo-2,3-dihydro-1$H$-indol-3-yl]-4-hydroxy-N,N-dimethyl-2-pyrrolidinecarboxamide, levorotatory isomer;
(2S, 4R)- 1-[5-Chloro-1-[(2,4-dimethoxyphenyl)sulphonyl]-3-(1,3-benzodioxol-4-yl)-2-oxo-2,3-dihydro-1$H$-indol-3-yl]-4-hydroxy-N,N-dimethyl-2-pyrrolidinecarboxamide, levorotatory isomer;
(2S, 4R)-1-[5,6-Dichloro-1-[(2,4-dimethoxyphenyl)sulphonyl]-3-(2-methoxyphenyl)-2-oxo-2,3-dihydro-1$H$-indol-3-yl]-4-hydroxy-N,N-dimethyl-2-pyrrolidinecarboxamide, levorotatory isomer,
*tert*-Butyl 2-[[(3R, 5S)-1-[5-chloro-1-[(2,4-dimethoxyphenyl)sulphonyl]-3-(2-methoxyphenyl)-2-oxo-2,3-dihydro-1$H$-indol-3-yl]-5-[(dimethylamino)carbonyl]-3-pyrrolidinyl]oxy]acetate, levorotatory isomer;

UNITED STATES PATENT AND TRADEMARK OFFICE
CERTIFICATE OF CORRECTION

PATENT NO. : 6,730,695 B2
APPLICATION NO. : 10/182048
DATED : May 4, 2004
INVENTOR(S) : Richard Roux et al.

It is certified that error appears in the above-identified patent and that said Letters Patent is hereby corrected as shown below:

Column 59 (cont'd),
2-[[(3R, 5S)-1-[5-Chloro-1-[(2,4-dimethoxyphenyl)sulphonyl]-3(2-methoxyphenyl)-2-oxo-2,3-dihydro-1*H*-indol-3-yl]-5-[(dimethylamino)carbonyl]-3-pyrrolidinyl]oxy] acetic acid, levorotatory isomer,
(2S, 4R)-1-[5-Chloro-1-[(2,4-dimethoxyphenyl)sulphonyl]-3-(2-methoxyphenyl)-2-oxo-2,3-dihydro-1*H*-indol-3-yl]-4-[2-[[2-hydroxy-1-(hydroxymethyl)-1-methylethyl] amino]-2-oxoethoxy]-N,N-dimethyl-2-pyrrolidinecarboxamide, levorotatory isomer;
(2S, 4R)-1-[5-Chloro-1-[(2,4-dimethoxyphenyl)sulphonyl]-3-(2-methoxyphenyl-2-oxo-2,3-dihydro-1*H*-indol-3-yl]-N,N-dimethyl-4-[2-oxo-2-(1-piperazinyl)ethoxy]-2-pyrrolidinecarboxamide, levorotatory isomer;
(2S, 4R)-1-[[(2,4-Dimethoxyphenyl)sulphonyl]-3-(2-methoxyphenyl)-2-oxo-2,3-dihydro-1*H*-indol-3-yl]-N,N -dimethyl-4-[2-oxo-2-(4-morpholinyl)ethoxy]-2-pyrrolidinecarboxamide, levorotatory isomer, and
(3R, 5S)-1-[5-Choro-1-[(2,4-dimethoxyphenyl)sulphonyl]-3-(2-methoxyphenyl)-2-oxo-2,3-dihydro-1*H*-indol-3-yl]-5-[(dimethylamino)carbonyl]-3-pyrrolidinyl3-(4-morpholinyl)propanoate, levorotatory isomer; or the acid-addition salts, solvates or hydrates thereof."
and should read
-- A compound according to Claim 5 selected from the group consisting of:
- (2S, 4R)-1-[5-Chloro-1-[(2,4-dimethoxyphenyl)sulphonyl]-3-(2-methoxyphenyl)-2-oxo-2,3-dihydro-1*H*-indol-3-yl]-4-hydroxy-N,N-dimethyl-2-pyrrolidinecarboxamide, levorotatory isomer;
- (2S,4R)-1-[5-Chloro-1-[(2,4-dimethoxyphenyl)sulphonyl]-3-(2-methoxyphenyl)-2-oxo-2,3-dihydro-1*H*-indol-3-yl]-4-methoxy-N,N-dimethyl-2-pyrrolidinecarboxamide, levorotatory isomer;
- (2S, 4R)-1-[5-Chloro-3-(2-chlorophenyl)-1-[(2,4-dimethoxyphenyl)sulphonyl]-2-oxo-2,3-dihydro-1*H*-indol-3-yl]-4-hydroxy-N,N-dimethyl-2-pyrrolidinecarboxamide, levorotatory isomer;
- (2S, 4R)-1-[5-Chloro-3-(2-chlorophenyl)-1-[(2,4-dimethoxyphenyl)sulphonyl]-6-methoxy-2-oxo-2,3-dihydro-1*H*-indol-3-yl]-4-methoxy-N,N-dimethyl-2-pyrrolidinecarboxamide, levorotatory isomer;
- (2S, 4R)-1-[5-Chloro-1-[(3,4-dimethoxyphenyl)sulphonyl)-3-(2-methoxyphenyl)-2-oxo-2,3-dihydro-1*H* indol-3-yl]-4-hydroxy-N,N-dimethyl-2-pyrrolidinecarboxamide, levorotatory isomer;
- (2S, 4R)-1-[5-Methyl-1-[(2,4-dimethoxyphenyl)sulphonyl)-3-(2-methoxyphenyl)-2-oxo-2,3-dihydro-1*H* indol-3-yl]-4-hydroxy-N,N-dimethyl-2-pyrrolidinecarboxamide, levorotatory isomer;

UNITED STATES PATENT AND TRADEMARK OFFICE
CERTIFICATE OF CORRECTION

PATENT NO. : 6,730,695 B2
APPLICATION NO. : 10/182048
DATED : May 4, 2004
INVENTOR(S) : Richard Roux et al.

It is certified that error appears in the above-identified patent and that said Letters Patent is hereby corrected as shown below:

Column 59 (cont'd),
- (2S, 4R)-1-[5-Trifluoromethoxy-1-[(2,4-dimethoxyphenyl)sulphonyl]-3-(2-methoxyphenyl)-2-oxo-2,3-dihydro-1*H*-indol-3-yl]-4-hydroxy-N,N-dimethyl-2 pyrrolidinecarboxamide, levorotatory isomer;
- (2S, 4R)-1-[5-Chloro-1-[(2,4-dimethoxyphenyl)sulphonyl]-3-(2-methoxyphenyl)-6-methyl-2-oxo-2,3-dihyro-1*H*-indol-3-yl]-4-hydroxy-N,N-dimethyl-2 pyrrolidinecarboxamide, levorotatory isomer;
- (2S, 4R)-1-[3-(2-Chlorophenyl)-1-[(2,4-dimethoxyphenyl)sulphonyl]-5,6-dimethyl-2-oxo-2,3-dihydro-1*H*-indol-3-yl]-4-hydroxy-N,N-dimethyl-2-pyrrolidinecarboxamide, levorotatory isomer;
- (2S, 4R)-1-[5-Chloro-1-[(2,4-dimethoxyphenyl)sulphonyl]-3-(2,3-dimethoxyphenyl)-2-oxo-2,3-dihydro-1*H*-indol-3-yl]-4-methoxy-N,N-dimethyl-2-pyrrolidinecarboxamide, levorotatory isomer;
- (2S, 4R)-1-[5 Chloro-1-[(2,4-dimethoxyphenyl)sulphonyl]-3-(2-methoxyphenyl)-6-trifluoromethy 2-oxo-2,3-dihydro-1*H*-indol-3-yl]-4-methoxy-N,N-dimethyl-2-pyrrolidinecarboxamide, levorotatory isomer;
- (2S, 4R)-1-[6-Chloro-1-[(2,4-dimethoxyphenyl)sulphonyl]-3-(2-methoxyphenyl)-5-methyl-2-oxo-2,3-dihydro-1*H*-indol-3-yl]-4-methoxy-N,N-dimethyl-2-pyrrolidinecarboxamide, levorotatory isomer;
- (2S, 4R)-1-[5-Chloro-1-[(2,4-dimethoxyphenyl)sulphonyl]-3-(2-methoxyphenyl)-2-oxo-2,3-dihydro-1H-indol-3-yl]-4-ethoxy-N,N-dimethyl-2-pyrrolidinecarboxamide, levorotatory isomer;
- (2S, 4R)-1-[5-Chloro-1-[(2,4-dimethoxyphenyl)sulphonyl]-3-(2,3-dimethoxyphenyl)-2-oxo-2,3-dihydro-1*H*-indol-3-yl]-4-hydroxy-N,N-dimethyl-2-pyrrolidinecarboxamide, levorotatory isomer;
- (2S, 4R)-1-[5,6-Dichloro-3-(2-chlorophenyl)-1-[(2,4-dimethoxyphenyl)sulphonyl]-2-oxo-2,3-dihydro-1*H*-indol-3-yl]-4-hydroxy-N,N-dimethyl-2-pyrrolidinecarboxamide, levorotatory isomer;
- (2S, 4R)-1-(5-Chloro-1-[(2,4-dimethoxyphenyl)sulphonyl]-3-(2-ethoxyphenyl)-2-oxo-2,3-dihydro-1*H*-indol-3-yl]-4-hydroxy-N,N-dimethyl-2-pyrrolidinecarboxamide, levorotatory isomer;
- (2S, 4R)-1-[5-Chloro-1-[(2,4-dimethoxyphenyl)sulphonyl]-3-(2,3-difluorophenyl)-2-oxo-2,3-dihydro-1*H*-indol-3-yl]-4-hydroxy-N,N-dimethyl-2-pyrrolidinecarboxamide, levorotatory isomer;
- (2S, 4R)-1-[5-Chloro-1-[(2,4-dimethoxyphenyl)sulphonyl]-3-(2,4-dimethoxyphenyl)-2-oxo-2,3-dihydro-1*H*-indol-3-yl]-4-hydroxy-N,N-dimethyl-2-pyrrolidinecarboxamide, levorotatory isomer;

UNITED STATES PATENT AND TRADEMARK OFFICE
CERTIFICATE OF CORRECTION

PATENT NO. : 6,730,695 B2
APPLICATION NO. : 10/182048
DATED : May 4, 2004
INVENTOR(S) : Richard Roux et al.

It is certified that error appears in the above-identified patent and that said Letters Patent is hereby corrected as shown below:

Column 59 (cont'd),
- (2S, 4R)-1-[5,6-Dichloro-1-[(2,4-dimethoxyphenyl)sulphonyl]-3-(2-methoxyphenyl)-2-oxo-2,3-dihydro-1$H$-indol-3-yl]-4-hydroxy-N,N-dimethyl-2-pyrrolidinecarboxamide, levorotatory isomer; and the acid-addition salts, solvates and hydrates thereof. --.

Signed and Sealed this

Eleventh Day of July, 2006

JON W. DUDAS
*Director of the United States Patent and Trademark Office*